US012559784B2

(12) United States Patent
Lebrun et al.

(10) Patent No.: US 12,559,784 B2
(45) Date of Patent: Feb. 24, 2026

(54) IN CHEMICO TEST FOR TOXICITY

(71) Applicant: Lebrun Labs LLC, Anaheim, CA (US)

(72) Inventors: Stewart Lebrun, Anaheim, CA (US);
Linda Nguyen, Orange, CA (US)

(73) Assignee: Lebrun Labs LLC, Anaheim, CA (US)

( * ) Notice: Subject to any disclaimer, the term of this patent is extended or adjusted under 35 U.S.C. 154(b) by 0 days.

(21) Appl. No.: 18/846,159

(22) PCT Filed: Feb. 14, 2024

(86) PCT No.: PCT/US2024/015781
§ 371 (c)(1),
(2) Date: Sep. 11, 2024

(87) PCT Pub. No.: WO2024/177860
PCT Pub. Date: Aug. 29, 2024

(65) Prior Publication Data
US 2025/0101489 A1     Mar. 27, 2025

Related U.S. Application Data

(60) Provisional application No. 63/448,157, filed on Feb. 24, 2023.

(51) Int. Cl.
*C12Q 1/42*      (2006.01)
*C12Q 1/44*      (2006.01)
*G01N 33/50*     (2006.01)

(52) U.S. Cl.
CPC ................ *C12Q 1/44* (2013.01); *C12Q 1/42* (2013.01)

(58) Field of Classification Search
CPC ........ C12Q 1/44; C12Q 1/42; G01N 33/5014; C12N 9/00
See application file for complete search history.

(56) References Cited

U.S. PATENT DOCUMENTS

| | | | |
|---|---|---|---|
| 6,998,249 B1 | 2/2006 | McKim et al. | |
| 2022/0000838 A1* | 1/2022 | Lebrun et al. ....... | A61K 31/375 31/375 |

FOREIGN PATENT DOCUMENTS

| | | |
|---|---|---|
| EP | 1258533 A1 | 11/2002 |
| RU | 2004102013 A | 7/2005 |
| RU | 2557535 C1 | 7/2015 |

OTHER PUBLICATIONS

Gerberick G. F. et al., "Investigation of Peptide Reactivity of Pro-hapten Skin Sensitizers Using a Peroxidase-Peroxide Oxidation System", Toxicological Sciences, 2009, vol. 112, No. 1, pp. 164-174. (Year: 2009).*

International Search Report and Written Opinion dated Jun. 5, 2024, issued in PCT International Appln. No. PCT/US2024/015781.

* cited by examiner

*Primary Examiner* — Satyendra K Singh
(74) *Attorney, Agent, or Firm* — Amster, Rothstein & Ebenstein LLP

(57)        ABSTRACT

The disclosure relates to formulations and methods for the in chemico testing of toxins based on a discovery that measuring a reduction in enzyme activity can be used to predict in vivo toxicity, including for example, a skin corrosion, skin irritation, eye corrosion, eye irritation, lung toxicity, liver toxicity, nervous system toxicity, developmental toxicity, acute toxicity etc. Disclosed methods are rapid, easy to perform and shelf-stable approaches for identification of toxic chemicals and materials.

19 Claims, 44 Drawing Sheets

Test Tube Results

GHS = Globally Harmonized System of Classification and Labeling of chemicals; NC = Not Classified How to Use the High-Throughput Skin Corrosion Test Kit 1. Add 20µL of test substance to 180µL of each test matrix (A1, B1, A2, B2), incubate for 4 hr ± 10 min 2. Add 20µL of test substance/test matrix to 200µL of detection reagent, incubate for 1 hr ± 10 min 3. Measure OD$_{405}$ of each test well 4. Subtract blank, divide into control, if < 40% = Corrosive 3A. Alkaline Phosphatase Results (With Ocular Discs)

| | | PBS | Naïve | C1 | C2 | C3 | C4 | C5 | C6 | C7 | C8 | C9 |
|---|---|---|---|---|---|---|---|---|---|---|---|---|
| 200 µL PNPP | 1 | 3.315 | 3.502 | 3.502 | 3.502 | 3.488 | 3.483 | 3.502 | 3.493 | 0.170 | 0.152 | 0.106 |
| | 2 | 3.349 | 3.502 | 3.469 | 3.502 | 3.502 | 3.502 | 3.502 | 3.400 | 0.166 | 0.159 | 0.102 |
| | 3 | 3.314 | 3.502 | 3.449 | 3.502 | 3.502 | 3.424 | 3.491 | 3.451 | 0.172 | 0.140 | 0.103 |
| | | | | | | | | | | | | |
| 200 µL PBS | 1 | 0.052 | 0.049 | 0.057 | 0.057 | 0.049 | 0.056 | 0.047 | 0.046 | 0.074 | 0.101 | 0.041 |
| | 2 | 0.058 | 0.051 | 0.047 | 0.046 | 0.045 | 0.045 | 0.043 | 0.044 | 0.056 | 0.052 | 0.040 |
| | 3 | 0.048 | 0.048 | 0.048 | 0.045 | 0.044 | 0.045 | 0.043 | 0.043 | 0.050 | 0.050 | 0.040 |

FIG. 3A

3B. Alkaline Phosphatase Results (No Ocular Discs)

| | | PBS | Naïve | C1 | C2 | C3 | C4 | C5 | C6 | C7 | C8 | C9 |
|---|---|---|---|---|---|---|---|---|---|---|---|---|
| 200 µL PNPP | 1 | 3.220 | 3.502 | 3.456 | 3.502 | 3.426 | 3.487 | 3.401 | 3.412 | 0.174 | 0.138 | 0.104 |
| | 2 | 3.235 | 3.502 | 3.502 | 3.502 | 3.439 | 3.502 | 3.395 | 3.445 | 0.185 | 0.176 | 0.129 |
| | 3 | 3.236 | 3.502 | 3.432 | 3.502 | 3.502 | 3.502 | 3.423 | 3.429 | 0.175 | 0.133 | 0.101 |
| | | | | | | | | | | | | |
| 200 µL PBS | 1 | 0.046 | 0.046 | 0.046 | 0.046 | 0.050 | 0.046 | 0.042 | 0.044 | 0.118 | 0.055 | 0.049 |
| | 2 | 0.045 | 0.048 | 0.044 | 0.042 | 0.048 | 0.045 | 0.044 | 0.045 | 0.120 | 0.051 | 0.041 |
| | 3 | 0.046 | 0.046 | 0.045 | 0.047 | 0.045 | 0.046 | 0.044 | 0.044 | 0.115 | 0.060 | 0.041 |

PNPP = p-Nitrophenyl phosphate disodium salt; PBS = Phosphate buffered saline; C = Chemical; C1 = (2-Bromoethyl)benzene; C2 = Triethylene glycol; C3 = 2-Methyl-4-phenyl-2-butanol; C4 = Cyclamen aldehyde; C5 = Heptanal; C6 = di-n-Propyl disulfide; C7 = Ethanolamine; C8 = Dimethyldipropylenetriamine; C9 = Acetic acid; The blank reaction reagent does not contain alkaline phosphatase.

FIG. 3B

Results from Repeated Study

| | | PBS | C1 | C2 | C3 | C4 | C5 | C6 | C7 | C8 | C9 | Naïve |
|---|---|---|---|---|---|---|---|---|---|---|---|---|
| 200 µL PNPP | 1 | 3.330 | 3.502 | 3.502 | 3.502 | 3.370 | 3.424 | 3.471 | 0.132 | 0.123 | 0.138 | 3.400 |
| | 2 | 3.379 | 3.502 | 3.502 | 3.502 | 3.383 | 3.361 | 3.502 | 0.128 | 0.124 | 0.138 | 3.429 |
| | 3 | 3.362 | 3.502 | 3.502 | 3.502 | 3.390 | 3.353 | 3.502 | 0.127 | 0.124 | 0.137 | 3.388 |
| | | | | | | | | | | | | |
| 200 µL PBS | 1 | 0.043 | 0.042 | 0.043 | 0.044 | 0.043 | 0.042 | 0.043 | 0.041 | 0.041 | 0.048 | 0.042 |
| | 2 | 0.042 | 0.041 | 0.042 | 0.043 | 0.041 | 0.038 | 0.044 | 0.039 | 0.040 | 0.039 | 0.040 |
| | 3 | 0.042 | 0.044 | 0.040 | 0.042 | 0.041 | 0.041 | 0.041 | 0.040 | 0.041 | 0.043 | 0.041 |
| | | | | | | | | | | | | |

FIG. 4

5A. Results from 10-minute PNPP Incubation

| | | PBS | C1 | C2 | C3 | C4 | C5 | C6 | C7 | C8 | C9 | Naïve |
|---|---|---|---|---|---|---|---|---|---|---|---|---|
| 200 µL PNPP | 1 | 3.502 | 3.502 | 3.466 | 3.502 | 3.409 | 3.297 | 3.384 | 3.449 | 0.273 | 3.281 | 3.502 |
| | 2 | 3.502 | 3.502 | 3.502 | 3.502 | 3.411 | 3.418 | 3.453 | 3.502 | 0.203 | 3.432 | 3.502 |
| | 3 | 3.502 | 3.344 | 3.489 | 3.502 | 3.502 | 3.479 | 3.483 | 3.500 | 0.215 | 3.407 | 3.502 |
| | | | | | | | | | | | | |
| 200 µL PBS | 1 | 0.042 | 0.042 | 0.041 | 0.042 | 0.038 | 0.060 | 0.039 | 0.041 | 0.041 | 0.041 | 0.040 |
| | 2 | 0.042 | 0.042 | 0.040 | 0.041 | 0.037 | 0.045 | 0.038 | 0.042 | 0.042 | 0.040 | 0.039 |
| | 3 | 0.041 | 0.041 | 0.041 | 0.042 | 0.038 | 0.050 | 0.043 | 0.042 | 0.040 | 0.040 | 0.040 |
| | | | | | | | | | | | | |

FIG. 5A

5B. Results from 1-hour PNPP Incubation

| | | PBS | C1 | C2 | C3 | C4 | C5 | C6 | C7 | C8 | C9 | Naïve |
|---|---|---|---|---|---|---|---|---|---|---|---|---|
| 200 µL PNPP | 1 | 3.302 | 3.423 | 3.502 | 3.502 | 3.438 | 3.442 | 3.406 | 0.352 | 0.115 | 3.349 | 3.330 |
| | 2 | 3.297 | 3.502 | 3.495 | 3.502 | 3.413 | 3.427 | 3.425 | 0.283 | 0.115 | 3.299 | 3.310 |
| | 3 | 3.268 | 3.483 | 3.502 | 3.502 | 3.434 | 3.420 | 3.383 | 0.333 | 0.112 | 3.348 | 3.423 |
| | | | | | | | | | | | | |
| 200 µL PBS | 1 | 0.043 | 0.043 | 0.040 | 0.041 | 0.049 | 0.042 | 0.042 | 0.040 | 0.040 | 0.040 | 0.042 |
| | 2 | 0.042 | 0.037 | 0.040 | 0.042 | 0.039 | 0.042 | 0.043 | 0.040 | 0.044 | 0.041 | 0.039 |
| | 3 | 0.045 | 0.041 | 0.040 | 0.041 | 0.039 | 0.040 | 0.044 | 0.042 | 0.043 | 0.040 | 0.039 |
| | | | | | | | | | | | | |

FIG. 5B

5C. Results from 4-hour PNPP Incubation

| | | PBS | C1 | C2 | C3 | C4 | C5 | C6 | C7 | C8 | C9 | Naïve |
|---|---|---|---|---|---|---|---|---|---|---|---|---|
| 200 µL PNPP | 1 | 3.252 | 3.502 | 3.502 | 3.502 | 3.439 | 3.502 | 3.502 | 0.122 | 0.111 | 0.282 | 3.342 |
| | 2 | 3.208 | 3.502 | 3.502 | 3.502 | 3.372 | 3.495 | 3.502 | 0.116 | 0.111 | 0.272 | 3.400 |
| | 3 | 3.165 | 3.502 | 3.502 | 3.502 | 3.369 | 3.400 | 3.495 | 0.114 | 0.110 | 0.284 | 3.223 |
| 200 µL PBS | 1 | 0.045 | 0.049 | 0.043 | 0.048 | 0.041 | 0.042 | 0.041 | 0.042 | 0.040 | 0.044 | 0.040 |
| | 2 | 0.050 | 0.042 | 0.040 | 0.041 | 0.040 | 0.041 | 0.040 | 0.040 | 0.040 | 0.043 | 0.040 |
| | 3 | 0.060 | 0.042 | 0.042 | 0.040 | 0.041 | 0.041 | 0.041 | 0.042 | 0.041 | 0.042 | 0.042 |

FIG. 5C

5D. Results from 18-hour PNPP Incubation

| | | PBS | C1 | C2 | C3 | C4 | C5 | C6 | C7 | C8 | C9 | Naïve |
|---|---|---|---|---|---|---|---|---|---|---|---|---|
| 200 µL PNPP | 1 | 3.256 | 3.424 | 3.417 | 3.502 | 3.309 | 3.415 | 3.502 | 0.112 | 0.109 | 0.107 | 3.402 |
| | 2 | 3.242 | 3.502 | 3.502 | 3.433 | 3.461 | 3.502 | 3.465 | 0.105 | 0.109 | 0.107 | 3.457 |
| | 3 | 3.226 | 3.502 | 3.390 | 3.502 | 3.375 | 3.502 | 3.427 | 0.110 | 0.111 | 0.116 | 3.383 |
| 200 µL PBS | 1 | 0.042 | 0.041 | 0.040 | 0.042 | 0.041 | 0.041 | 0.041 | 0.041 | 0.040 | 0.042 | 0.040 |
| | 2 | 0.042 | 0.040 | 0.040 | 0.042 | 0.039 | 0.041 | 0.040 | 0.041 | 0.040 | 0.042 | 0.040 |
| | 3 | 0.041 | 0.041 | 0.040 | 0.043 | 0.040 | 0.041 | 0.041 | 0.041 | 0.041 | 0.046 | 0.040 |

PNPP = p-Nitrophenyl phosphate disodium salt; PBS = Phosphate buffered saline; C = Chemical;
C1 = 1-Bromo-4-chlorobutane; C2 = 1,5-Hexadiene; C3 = Isopropanol; C4 = Isopropyl myristate;
C5 = di-n-Propyl disulfide; C6 = Cyclamen aldehyde; C7 = Dimethyldipropylenetriamine;
C8 = Potassium hydroxide (10%); C9 = 2-Methylbutyric acid

FIG. 5D

6A. Results for Controls

| | 1 | 2 | 3 | 4 | 5 | 6 | 7 | 8 | 9 | 10 | 11 | 12 |
|---|---|---|---|---|---|---|---|---|---|---|---|---|
| (1) old AP — A | 3.385 | 3.502 | 3.502 | 3.502 | 3.502 | 3.398 | 0.088 | 0.089 | 0.088 | 0.116 | 0.115 | 0.113 |
| (2) old AP (1:10) — B | 3.383 | 3.502 | 3.502 | 3.502 | 3.492 | 3.461 | 0.087 | 0.088 | 0.091 | 0.113 | 0.118 | 0.112 |
| (3) old AP (1:100) — C | 3.502 | 3.502 | 3.502 | 3.502 | 3.502 | 3.479 | 0.088 | 0.090 | 0.089 | 0.116 | 0.113 | 0.111 |
| (4) New AP — D | 3.396 | 3.502 | 3.502 | 3.502 | 3.502 | 3.502 | 0.770 | 0.693 | 0.656 | 0.657 | 0.709 | 0.713 |
| (5) PBS only — E | 0.113 | 0.112 | 0.110 | 0.133 | 0.132 | 0.131 | 0.148 | 0.087 | 0.092 | 0.114 | 0.114 | 0.114 |
| F | (1) NC2 0.299 | 0.296 | 0.296 | PC2 0.327 | (2) NC2 0.301 | PC2 0.324 | (3) NC2 0.300 | PC2 0.322 | (4) NC2 0.402 | PC2 0.596 | (5) NC2 0.294 | PC2 0.319 |
| G *DEMO - STOCK INK | 2.556 | 2.589 | 2.652 | 0.323 | 0.290 | 0.322 | 0.302 | 0.330 | 0.448 | 0.622 | 0.292 | 0.311 |
| H | 3.092 | 3.017 | 2.996 | 0.322 | 0.302 | 0.321 | 0.299 | 0.328 | 0.441 | 0.617 | 0.303 | 0.317 |

FIG. 6A

6B. Results for Original AP (1:1)

| | 1 | 2 | 3 | 4 | 5 | 6 | 7 | 8 | 9 | 10 | 11 | 12 |
|---|---|---|---|---|---|---|---|---|---|---|---|---|
| A | 5 3.283 | 3.347 | 3.502 | 6 3.496 | 3.502 | 3.502 | 7 3.502 | 3.502 | 3.427 | 8 3.229 | 3.364 | 3.206 |
| B | 9 3.305 | 3.480 | 3.502 | 10 3.502 | 3.502 | 3.487 | 11 3.449 | 3.502 | 3.420 | 12 3.347 | 3.440 | 3.187 |
| C | 13 3.330 | 3.502 | 3.502 | 14 3.502 | 3.502 | 3.502 | 15 3.469 | 3.502 | 3.455 | 16 3.315 | 3.386 | 3.142 |
| D | 17 3.352 | 3.502 | 3.483 | 18 3.502 | 3.502 | 3.502 | 19 3.446 | 3.502 | 3.421 | 20 3.363 | 3.390 | 3.175 |
| E | 21 3.369 | 3.488 | 3.502 | 22 3.502 | 3.502 | 3.502 | 23 3.435 | 3.502 | 3.446 | 24 3.321 | 3.439 | 3.221 |
| F | 25 0.250 | 0.228 | 0.235 | 26 0.116 | 0.087 | 0.104 | 27 3.489 | 3.502 | 3.471 | 28 3.281 | 3.409 | 3.182 |
| G | 29 3.345 | 3.453 | 3.502 | 30 3.502 | 3.502 | 3.502 | 31 3.460 | 3.502 | 3.470 | 32 3.360 | 3.411 | 3.201 |
| H | 33 3.343 | 3.243 | 3.361 | 34 3.360 | 3.302 | 3.260 | | | | | | |

FIG. 6B

6C. Results for Original AP (1:10)

| | 1 | 2 | 3 | 4 | 5 | 6 | 7 | 8 | 9 | 10 | 11 | 12 |
|---|---|---|---|---|---|---|---|---|---|---|---|---|
| A | [5] 3.292 | 3.357 | 3.481 | [6] 3.502 | 3.502 | 3.374 | [7] 3.502 | 3.502 | 3.412 | [8] 3.329 | 3.431 | 3.231 |
| B | [9] 3.275 | 3.456 | 3.502 | [10] 3.502 | 3.502 | 3.428 | [11] 3.502 | 3.502 | 3.390 | [12] 3.391 | 3.502 | 3.215 |
| C | [13] 3.305 | 3.474 | 3.502 | [14] 3.500 | 3.502 | 3.472 | [15] 3.502 | 3.502 | 3.435 | [16] 3.462 | 3.432 | 3.171 |
| D | [17] 3.309 | 3.481 | 3.499 | [18] 3.502 | 3.502 | 3.460 | [19] 3.502 | 3.502 | 3.402 | [20] 3.432 | 3.366 | 3.166 |
| E | [21] 3.345 | 3.428 | 3.481 | [22] 3.502 | 3.450 | 3.484 | [23] 3.502 | 3.502 | 3.382 | [24] 3.416 | 3.439 | 3.180 |
| F | [25] 2.542 | 3.342 | 3.502 | [26] 0.103 | 0.103 | 0.103 | [27] 0.423 | 0.417 | 0.425 | [28] 3.460 | 3.481 | 3.189 |
| G | [29] 3.336 | 3.405 | 3.502 | [30] 3.502 | 3.502 | 3.485 | [31] 3.485 | 3.502 | 3.338 | [32] 3.471 | 3.445 | 3.190 |
| H | [33] 0.200 | 0.186 | 0.181 | [34] 3.384 | 3.309 | 3.329 | | | | | | |

FIG. 6C

6D. Results for Original AP (1:100)

| | 1 | 2 | 3 | 4 | 5 | 6 | 7 | 8 | 9 | 10 | 11 | 12 |
|---|---|---|---|---|---|---|---|---|---|---|---|---|
| A | 5 3.460 | 3.502 | 3.502 | 6 3.502 | 3.502 | 3.433 | 7 3.502 | 3.502 | 3.413 | 8 2.050 | 2.319 | 3.202 |
| B | 9 3.432 | 3.467 | 3.502 | 10 3.502 | 3.502 | 3.502 | 11 3.502 | 3.502 | 3.484 | 12 3.406 | 3.502 | 3.192 |
| C | 13 3.502 | 3.502 | 3.502 | 14 3.502 | 3.502 | 3.502 | 15 3.502 | 3.502 | 3.456 | 16 3.400 | 3.480 | 3.318 |
| D | 17 3.481 | 3.502 | 3.502 | 18 3.502 | 3.502 | 3.502 | 19 3.502 | 3.502 | 3.396 | 20 3.502 | 3.502 | 3.175 |
| E | 21 3.502 | 3.502 | 3.502 | 22 3.502 | 3.502 | 3.502 | 23 3.502 | 3.502 | 3.478 | 24 3.474 | 3.475 | 3.239 |
| F | 25 0.108 | 0.107 | 0.114 | 26 0.112 | 0.103 | 0.120 | 27 0.091 | 0.095 | 0.094 | 28 3.462 | 3.491 | 3.333 |
| G | 29 3.466 | 3.502 | 3.502 | 30 0.204 | 0.216 | 0.239 | 31 0.991 | 0.974 | 1.167 | 32 3.244 | 3.057 | 3.152 |
| H | 33 0.102 | 0.102 | 0.103 | 34 3.431 | 3.502 | 3.461 | | | | | | |

FIG. 6D

6E. Results for New AP (1:1)

| | 1 | 2 | 3 | 4 | 5 | 6 | 7 | 8 | 9 | 10 | 11 | 12 |
|---|---|---|---|---|---|---|---|---|---|---|---|---|
| A | 3.437 (5) | 3.456 | 3.502 | 3.496 (6) | 3.502 | 3.484 | 3.472 (7) | 3.483 | 3.336 | 3.215 (8) | 3.302 | 3.132 |
| B | 3.426 (9) | 3.487 | 3.502 | 3.502 (10) | 3.502 | 3.502 | 3.502 (11) | 3.502 | 3.462 | 3.493 (12) | 3.409 | 3.134 |
| C | 3.453 (13) | 3.502 | 3.502 | 3.502 (14) | 3.502 | 3.502 | 3.502 (15) | 3.502 | 3.480 | 3.368 (16) | 3.462 | 3.020 |
| D | 3.502 (17) | 3.432 | 3.495 | 3.502 (18) | 3.502 | 3.502 | 3.502 (19) | 3.502 | 3.470 | 3.377 (20) | 3.415 | 3.048 |
| E | 3.500 (21) | 3.502 | 3.502 | 3.502 (22) | 3.502 | 3.502 | 3.502 (23) | 3.502 | 3.502 | 3.417 (24) | 3.368 | 3.065 |
| F | 3.502 (25) | 3.480 | 3.502 | 0.149 (26) | 0.144 | 0.152 | 3.502 (27) | 3.502 | 3.488 | 3.406 (28) | 3.360 | 3.008 |
| G | 3.502 (29) | 3.467 | 3.502 | 3.502 (30) | 3.502 | 3.502 | 3.502 (31) | 3.502 | 3.427 | 3.493 (32) | 3.386 | 3.042 |
| H | 3.429 (33) | 3.357 | 3.440 | 3.370 (34) | 3.384 | 3.305 | | | | | | |

FIG. 6E

6F. Results for Phosphate Buffered Saline (PBS) Blanks

| | 1 | 2 | 3 | 4 | 5 | 6 | 7 | 8 | 9 | 10 | 11 | 12 |
|---|---|---|---|---|---|---|---|---|---|---|---|---|
| A | 5 0.114 | 0.118 | 0.118 | 6 0.117 | 0.110 | 0.112 | 7 0.107 | 0.112 | 0.119 | 8 0.116 | 0.174 | 0.177 |
| B | 9 0.115 | 0.122 | 0.118 | 10 0.120 | 0.117 | 0.122 | 11 0.114 | 0.118 | 0.114 | 12 0.113 | 0.110 | 0.117 |
| C | 13 0.547 | 0.548 | 0.459 | 14 0.118 | 0.111 | 0.137 | 15 0.118 | 0.117 | 0.119 | 16 0.120 | 0.117 | 0.113 |
| D | 17 0.113 | 0.115 | 0.117 | 18 0.131 | 0.122 | 0.124 | 19 0.237 | 0.258 | 0.258 | 20 0.132 | 0.118 | 0.127 |
| E | 21 0.116 | 0.115 | 0.111 | 22 0.122 | 0.119 | 0.121 | 23 0.114 | 0.113 | 0.119 | 24 0.155 | 0.143 | 0.146 |
| F | 25 0.117 | 0.118 | 0.120 | 26 0.110 | 0.109 | 0.113 | 27 0.102 | 0.095 | 0.111 | 28 0.119 | 0.114 | 0.126 |
| G | 29 0.119 | 0.118 | 0.116 | 30 0.118 | 0.114 | 0.117 | 31 0.436 | 0.171 | 0.137 | 32 0.141 | 0.126 | 0.120 |
| H | 33 0.105 | 0.103 | 0.106 | 34 0.116 | 0.122 | 0.122 | | | | | | |

Old AP = Original stock; AP = Alkaline Phosphatase; PBS = Phosphate buffered saline

FIG. 6F

7A. Results from 3-hr Exposure; PNPP: 30-minutes

| | | water 1 | methanol 2 | mineral oil 3 | 1-bromo-butane NC 4 | 1,5-hexadiene NC 5 | di-n-propyl disulfide Cat.2 6 | nonyl aldehyde Cat.2 7 | octanoic acid Cat.1 8 | dimethyl-isopropyl-amine Cat.1 9 | 5-isopropyl-2-methyl phenol Cat.1 10 | n-heptyl-amine Cat.1 11 | N, N-diethyl-benzylamine Cat.1 12 |
|---|---|---|---|---|---|---|---|---|---|---|---|---|---|
| A | PBS | 3.303 | 3.502 | 3.502 | 3.502 | 3.502 | 3.410 | 3.502 | 2.199 | 3.463 | 0.379 | 3.337 | 3.101 |
| B | Ethanol | 3.340 | 3.470 | 3.502 | 2.403 | 1.702 | 3.015 | 1.589 | 1.597 | 0.918 | 1.384 | 0.534 | 0.531 |
| C | Acetone | 3.308 | 3.502 | 3.493 | / | / | / | / | 2.817 | 1.665 | 2.772 | 0.206 | / |
| D | | | | | | | | | | | | | |
| (A)E | PBS | 3.294 | 3.502 | 2.329 | 3.440 | 3.502 | 3.410 | 3.479 | 0.424 | 1.982 | 0.155 | 3.232 | 3.207 |
| (B)F | Ethanol | 3.301 | 0.373 | 0.609 | 0.482 | / | 1.324 | 0.857 | 0.808 | 0.176 | 0.742 | 0.126 | 0.442 |
| (C)G | Acetone | 3.265 | 0.296 | 1.066 | / | / | / | 3.007 | 0.183 | / | 0.346 | 0.105 | / |

7B. Results from 3-hr Exposure; PNPP: 1-hr

|  | water 1 | methanol 2 | mineral oil 3 | 1-bromo-4-chlorobutane NC 4 | 1,5-hexadiene NC 5 | di-n-propyl disulfide Cat.2 6 | nonyl aldehyde Cat.2 7 | octanoic acid Cat.1 8 | dimethyl-isopropyl-amine Cat.1 9 | 5-isopropyl-2-methyl phenol Cat.1 10 | n-heptyl-amine Cat.1 11 | N,N-diethyl-benzylamine Cat.1 12 |
|---|---|---|---|---|---|---|---|---|---|---|---|---|
| A PBS | 3.301 | 3.502 | 3.502 | 3.502 | 3.502 | 3.465 | 3.478 | 3.409 | 3.446 | 0.749 | 3.386 | 3.100 |
| B Ethanol | 3.357 | 3.502 | 3.502 | 3.349 | 2.947 | 3.394 | 3.078 | 3.226 | 3.396 | 2.581 | 1.304 | 1.289 |
| C Acetone | 3.326 | 3.502 | 3.470 | / | / | / | / | 3.491 | 3.250 | 3.394 | 0.419 | / |
| D | | | | | | | | | | | | |
| (A)E PBS | 3.334 | 3.502 | 3.349 | 3.502 | 3.502 | 3.463 | 3.487 | 0.633 | 3.292 | 0.251 | 3.449 | 3.253 |
| (B)F Ethanol | 3.321 | 0.567 | 1.057 | 0.700 | / | 1.106 | 1.688 | 1.616 | 0.315 | 1.185 | 0.191 | 0.695 |
| (C)G Acetone | 3.319 | 0.349 | 1.860 | / | / | / | 3.471 | 0.209 | / | 0.887 | 0.143 | / |

(Rows A–C: 10 µL; Rows E–G: 50 µL)

FIG. 7B

8A. Results from 22-hr Exposure; PNPP: 10-minutes

|  | water 1 | methanol 2 | mineral oil 3 | 1-bromo-4-chlorobutane (NC) 4 | 1,5-hexadiene (NC) 5 | di-n-propyl disulfide (2) 6 | nonyl aldehyde (2) 7 | octanoic acid (1) 8 | dimethyl-isopropyl-amine (1) 9 | 5-isopropyl 2-methyl phenol (1) 10 | n-heptyl-amine (1) 11 | N,N-diethyl-benzylamide (1) 12 |
|---|---|---|---|---|---|---|---|---|---|---|---|---|
| A PBS | 3.502 | 3.400 | 2.171 | 2.547 | 2.166 | 2.163 | 1.462 | 0.534 | 2.024 | 0.144 | 0.612 | 1.073 |
| B Ethanol | 2.665 | 1.843 | / | 1.405 | 1.012 | 1.765 | 0.435 | 0.952 | 0.503 | 0.126 | 0.166 | 0.111 |
| C Acetone | / | / | / | / | / | / | / | 0.589 | / | / | / | / |
| D | | | | | | | | | | | | |
| (A)E PBS | 2.426 | 2.709 | 0.134 | 1.357 | 2.663 | 2.414 | 1.304 | 0.216 | 0.451 | 0.217 | / | 0.789 |
| (B)F Ethanol | 2.656 | / | / | / | / | / | 0.302 | 0.268 | / | 0.100 | / | / |
| (C)G Acetone | 3.365 | / | 0.292 | / | / | / | / | 0.168 | / | 0.301 | / | / |

(Columns A–D: 10 µL; Columns E–G: 50 µL)

FIG. 8A

8B. Results from 22-hr Exposure; PNPP: 30-minutes

| | | water 1 | methanol 2 | mineral oil 3 | 1-bromo-4-chlorobutane (NC) 4 | 1,5-hexadiene (NC) 5 | di-n-propyl disulfide (2) 6 | nonyl aldehyde (2) 7 | octanoic acid (1) 8 | dimethyl-isopropyl-amine (1) 9 | 5-isopropyl 2-methyl phenol (1) 10 | n-heptyl-amine (1) 11 | N, N-diethyl-benzylamide (1) 12 |
|---|---|---|---|---|---|---|---|---|---|---|---|---|---|
| A | PBS | 3.450* | 3.502* | 3.472* | 3.502 | 3.502 | 3.465 | 3.405 | 1.393* | 3.377 | 0.278 | 2.160 | 3.421 |
| B | Ethanol | 3.450 | 3.349 | / | 2.627* | 2.163* | 2.345* | 1.012* | 2.053 | 1.475* | 0.206* | 0.205* | 0.150* |
| C | Acetone | / | / | / | / | / | / | / | 1.170 | / | / | / | / |
| D | | | | | | | | | | | | | |
| (A) E | PBS | 3.434 | 3.502 | 0.218 | 2.922 | 3.502 | 3.489 | 3.341 | 0.286 | 1.321 | 0.384 | / | 3.212 |
| (B) F | Ethanol | 3.502 | / | / | / | / | / | 0.830 | 0.421 | / | 0.137 | / | / |
| (C) G | Acetone | 3.450 | / | 0.698 | / | / | / | / | 0.167 | / | 0.775 | / | / |

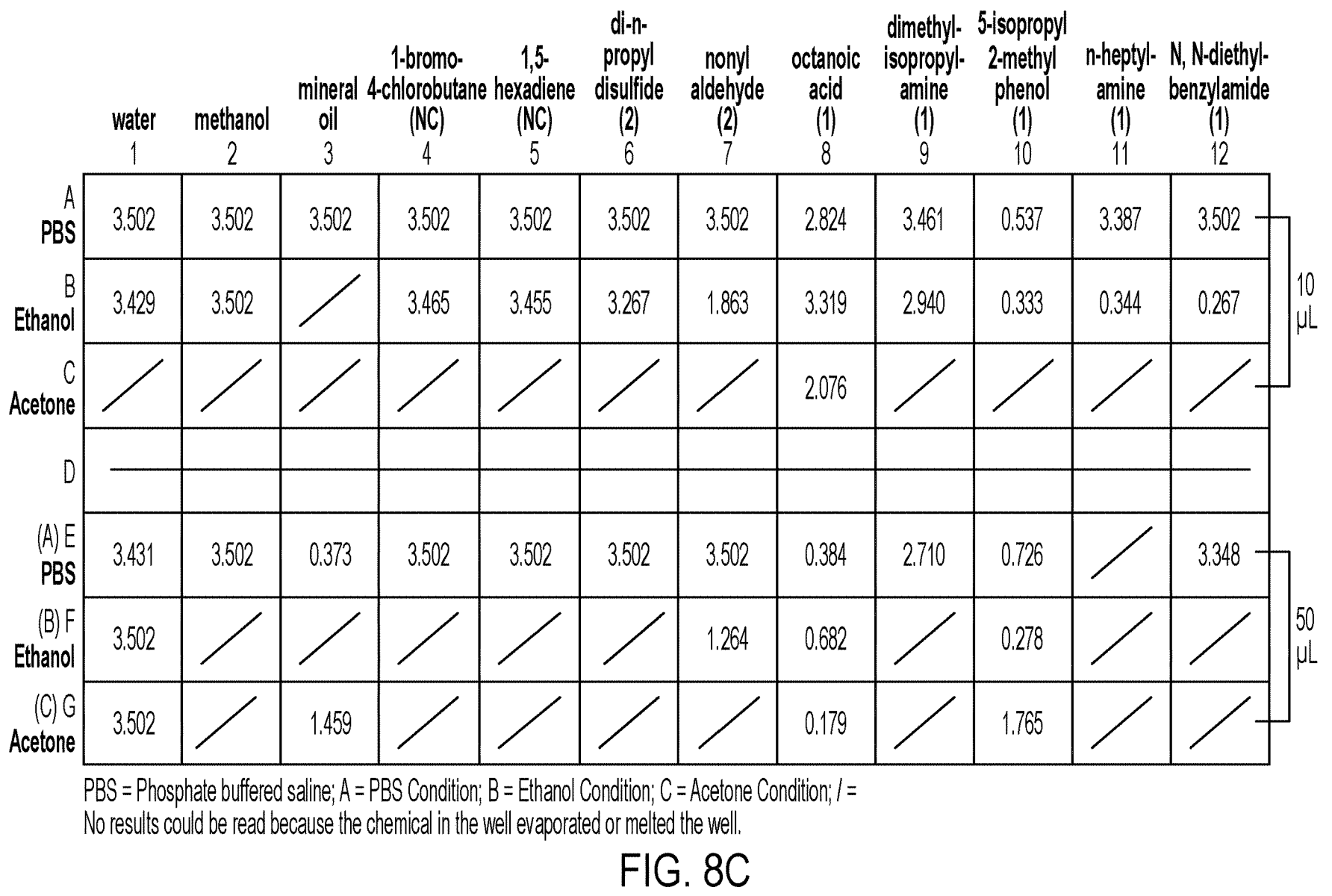

|  | water (1) | methanol (2) | mineral oil (3) | 1-bromo-4-chlorobutane (NC) (4) | 1,5-hexadiene (NC) (5) | di-n-propyl disulfide (2) (6) | nonyl aldehyde (2) (7) | octanoic acid (1) (8) | dimethyl-isopropyl-amine (1) (9) | 5-isopropyl-2-methyl phenol (1) (10) | n-heptyl-amine (1) (11) | N,N-diethyl-benzylamide (1) (12) |
|---|---|---|---|---|---|---|---|---|---|---|---|---|
| A PBS | 3.502 | 3.502 | 3.502 | 3.502 | 3.502 | 3.502 | 3.502 | 2.824 | 3.461 | 0.537 | 3.387 | 3.502 |
| B Ethanol | 3.429 | 3.502 | / | 3.465 | 3.455 | 3.267 | 1.863 | 3.319 | 2.940 | 0.333 | 0.344 | 0.267 |
| C Acetone | / | / | / | / | / | / | / | 2.076 | / | / | / | / |
| D | — |  |  |  |  |  |  |  |  |  |  | | |
| (A) E PBS | 3.431 | 3.502 | 0.373 | 3.502 | 3.502 | 3.502 | 3.502 | 0.384 | 2.710 | 0.726 | / | 3.348 |
| (B) F Ethanol | 3.502 | / | / | / | / | / | 1.264 | 0.682 | / | 0.278 | / | / |
| (C) G Acetone | 3.502 | / | 1.459 | / | / | / | / | 0.179 | / | 1.765 | / | / |

10 µL (columns A–C); 50 µL (columns E–G)

PBS = Phosphate buffered saline; A = PBS Condition; B = Ethanol Condition; C = Acetone Condition; / = No results could be read because the chemical in the well evaporated or melted the well.

FIG. 8C

9A. Results for 4-hr Exposure; PNPP· 30-minutes

| | | 1 | 2 | 3 | 4 | 5 | 6 | 7 | 8 | 9 | 10 | 11 | 12 |
|---|---|---|---|---|---|---|---|---|---|---|---|---|---|
| PBS 1:100 | A | 3.318 | 3.472 | 3.502 | 3.502 | 3.502 | 3.380 | 3.502 | 1.101 | 3.216 | 0.673 | 2.532 | 3.082 |
| OBS 1:1000 | B | 0.488 | 0.311 | 0.233 | 0.353 | 1.095 | 0.266 | 0.601 | 0.157 | 0.466 | 0.151 | 0.889 | 0.448 |
| EtOH 1:100 | C | 3.327 | 3.420 | 3.457 | 2.058 | 3.120 | 3.318 | 1.641 | 1.501 | 0.281 | 1.153 | 0.231 | 0.383 |
| EtOH 1:1000 | D RT | 0.358 | 0.327 | 0.605 | 0.227 | 0.109 | 0.434 | 0.133 | 0.115 | 0.096 | 0.107 | 0.225 | 0.144 |
| PBS 1:100 | E 37°C | 3.314 | 3.408 | 3.323 | 3.502 | 3.502 | 3.246 | 3.502 | 0.167 | 0.228 | 0.327 | 0.849 | 2.032 |
| PBS 1:1000 | F | 0.303 | 0.170 | 0.187 | 0.784 | 0.937 | 0.214 | 0.464 | 0.125 | 0.118 | 0.125 | 0.191 | 0.363 |
| EtOH 1:100 | G | 3.312 | 2.152 | 0.424 | 0.196 | 0.173 | 0.419 | 0.955 | 0.634 | 0.110 | 0.187 | 0.283 | 0.155 |
| EtOH 1:1000 | H | 0.351 | 0.307 | 0.271 | 0.108 | 0.097 | 0.370 | 0.153 | 0.119 | 0.103 | 0.119 | 0.145 | 0.107 |

FIG. 9A

9B. Results for 4-hr Exposure; PNPP· 1-hr

|  | | 1 | 2 | 3 | 4 | 5 | 6 | 7 | 8 | 9 | 10 | 11 | 12 |
|---|---|---|---|---|---|---|---|---|---|---|---|---|---|
| PBS 1:100 | A | 3.361 | 3.502 | 3.502 | 3.502 | 3.495 | 3.458 | 3.450 | 1.776 | 3.353 | 1.220 | 2.089 | 3.216 |
| PBS 1:1000 | B | 0.684 | 0.359 | 0.290 | 0.483 | 1.570 | 0.364 | 0.922 | 0.189 | 0.776 | 0.202 | 0.259 | 0.820 |
| EtOH 1:100 | C | 3.352 | 3.500 | 3.502 | 3.063 | 3.489 | 3.411 | 3.112 | 2.943 | 0.485 | 2.850 | 0.279 | 0.475 |
| EtOH 1:1000 | D RT | 0.513 | 0.428 | 0.799 | 0.316 | 0.127 | 0.342 | 0.167 | 0.134 | 0.099 | 0.120 | 0.202 | 0.587 |
| PBS 1:100 | 37°C E | 3.371 | 3.502 | 3.431 | 3.502 | 3.481 | 3.428 | 3.485 | 0.199 | 0.362 | 0.598 | 0.833 | 2.566 |
| PBS 1:1000 | F | 0.399 | 0.189 | 0.205 | 1.100 | 1.526 | 0.276 | 0.647 | 0.132 | 0.134 | 0.155 | 0.197 | 0.416 |
| EtOH 1:100 | G | 3.357 | 2.730 | 0.461 | 0.270 | 0.275 | 0.517 | 1.002 | 1.411 | 0.149 | 0.338 | 0.263 | 0.298 |
| EtOH 1:1000 | H | 0.497 | 0.270 | 0.263 | 0.119 | 0.101 | 0.268 | 0.099 | 0.136 | 0.098 | 0.085 | 0.157 | 0.271 |

FIG. 9B

10A. Results for 22-hr Exposure; PNPP- 30-minutes

| | | 1 | 2 | 3 | 4 | 5 | 6 | 7 | 8 | 9 | 10 | 11 | 12 |
|---|---|---|---|---|---|---|---|---|---|---|---|---|---|
| PBS 1:100 | A | 3.312 | 3.502 | 3.502 | 3.492 | 3.472 | 3.475 | 3.461 | 0.144 | 2.504 | 0.183 | 0.768 | 3.154 |
| PBS 1:1000 | B | 0.145 | 0.222 | 0.131 | 0.306 | 1.057 | 0.151 | 0.657 | 0.126 | 0.363 | 0.222 | 0.202 | 0.634 |
| EtOH 1:100 | C | 3.295 | 1.748 | 0.817 | 1.379 | 0.359 | 1.086 | 1.059 | 0.751 | 0.218 | 0.590 | 0.159 | 0.133 |
| EtOH 1:1000 | D (RT) | 0.387 | 0.331 | 0.320 | 0.123 | 0.101 | 0.263 | 0.135 | 0.117 | 0.102 | 0.113 | 0.152 | 0.103 |
| PBS 1:100 | E (37°C) | 2.752 | 0.886 | 2.745 | 3.337 | 3.502 | 3.429 | 3.447 | 0.125 | 0.113 | 0.131 | 0.124 | 0.180 |
| PBS 1:1000 | F | 0.128 | 0.155 | 0.130 | 0.858 | 0.984 | 0.171 | 0.329 | 0.125 | 0.115 | 0.128 | 0.137 | 0.134 |
| EtOH 1:100 | G | 1.392 | 0.792 | 0.323 | 0.126 | 0.110 | 0.402 | 0.389 | 0.413 | 0.100 | 0.169 | 0.132 | 0.114 |
| EtOH 1:1000 | H | 0.272 | 0.367 | 0.267 | 0.120 | 0.101 | 0.547 | 0.149 | 0.123 | 0.097 | 0.122 | 0.171 | 0.117 |

FIG. 10A

10B. Results for 22-hr Exposure; PNPP: 1-hr

| | | 1 | 2 | 3 | 4 | 5 | 6 | 7 | 8 | 9 | 10 | 11 | 12 |
|---|---|---|---|---|---|---|---|---|---|---|---|---|---|
| PBS 1:100 | A | 3.334 | 3.502 | 3.502 | 3.502 | 3.440 | 3.491 | 3.424 | 0.158 | 3.333 | 0.185 | 1.103 | 3.184 |
| PBS 1:1000 | B | 0.147 | 0.241 | 0.132 | 0.412 | 1.524 | 0.158 | 0.978 | 0.130 | 0.525 | 0.279 | 0.232 | 1.035 |
| EtOH 1:100 | C | 3.319 | 2.243 | 1.111 | 2.069 | 0.547 | 1.508 | 1.725 | 1.215 | 0.337 | 0.965 | 0.153 | 0.169 |
| EtOH 1:1000 | D | 0.518 | 0.305 | 0.302 | 0.118 | 0.107 | 0.217 | 0.141 | 0.121 | 0.100 | 0.128 | 0.125 | 0.103 |
| PBS 1:100 | E | 3.282 | 1.260 | 3.530 | 3.502 | 3.402 | 3.424 | 3.452 | 0.132 | 0.116 | 0.159 | 0.131 | 0.225 |
| PBS 1:1000 | F | 0.131 | 0.141 | 0.132 | 1.219 | 1.450 | 0.177 | 0.461 | 0.127 | 0.116 | 0.138 | 0.137 | 0.143 |
| EtOH 1:100 | G | 2.099 | 0.857 | 0.325 | 0.143 | 0.130 | 0.356 | 0.577 | 0.742 | 0.105 | 0.251 | 0.125 | 0.127 |
| EtOH 1:1000 | H | 0.358 | 0.367 | 0.261 | 0.120 | 0.101 | 0.439 | 0.148 | 0.118 | 0.097 | 0.124 | 0.169 | 0.108 |

RT / 37°C

PBS = Phosphate buffered saline; RT = Room temperature; EtOH = Ethanol; PNPP = p-Nitrophenyl phosphate disodium salt; 1 = Water;
2 = 4-(Methylthio)benzaldehyde; 3 = l-Bromo-4-chlorobutane; 4 = 1,5-Hexadiene; 5 = alpha-Terpineol; 6 = di-n-Propyl disulfide; 7 = Nonyl
aldehyde; 8 = Octanoic acid; 9 = Dimethylisopropylamine; 10 = 5-Isopropyl-2-methylphenol; 11 = n-Heptylamine; 12 = N,N-Dimethylbenzylamine

FIG. 10B

11A. Results for Controls

| | 1 | 2 | 3 | 4 | 5 | 6 | 7 | 8 | 9 | 10 | 11 | 12 |
|---|---|---|---|---|---|---|---|---|---|---|---|---|
| R1+ A | 1 / 3.487 | 1 / 3.502 | 1 / 3.452 | 2 / 3.502 | 2 / 3.502 | 2 / 3.467 | 3 / 0.090 | 3 / 0.091 | 3 / 0.093 | 4 / 0.112 | 4 / 0.114 | 4 / 0.118 |
| R1- B | 1 / 0.124 | 1 / 0.123 | 1 / 0.129 | 2 / 0.138 | 2 / 0.138 | 2 / 0.138 | 3 / 0.090 | 3 / 0.090 | 3 / 0.091 | 4 / 0.114 | 4 / 0.118 | 4 / 0.118 |
| R2+ C | 1 / 3.471 | 1 / 3.476 | 1 / 3.412 | 2 / 3.502 | 2 / 3.502 | 2 / 3.434 | 3 / 2.778 | 3 / 2.829 | 3 / 2.829 | 4 / 3.014 | 4 / 3.162 | 4 / 2.875 |
| R2- D | 1 / 0.100 | 1 / 0.095 | 1 / 0.095 | 2 / 0.117 | 2 / 0.117 | 2 / 0.118 | 3 / 0.092 | 3 / 0.092 | 3 / 0.093 | 4 / 0.112 | 4 / 0.113 | 4 / 0.112 |
| E | PBS -Azide | | M. Ink water | M. Ink - A4 | | | | | | | | |
| F | 3.502 | | 2.700 | 2.816 | | | | | | | | |
| G | 3.400 | | 2.710 | 2.865 | | | | | | | | |
| H | 3.224 | | 2.610 | 2.812 | | | | | | | | |

FIG. 11A

11B. Results for R1+ (Alkaline Phosphatase + Buffered Saline)

| | 1 | 2 | 3 | 4 | 5 | 6 | 7 | 8 | 9 | 10 | 11 | 12 |
|---|---|---|---|---|---|---|---|---|---|---|---|---|
| A | 5<br>3.410 | 5<br>3.502 | 5<br>3.502 | 6<br>3.461 | 6<br>3.481 | 6<br>3.462 | 7<br>3.502 | 7<br>3.451 | 7<br>3.420 | 8<br>3.390 | 8<br>3.431 | 8<br>3.265 |
| B | 9<br>3.372 | 9<br>3.488 | 9<br>3.475 | 10<br>3.417 | 10<br>3.502 | 10<br>3.492 | 11<br>3.470 | 11<br>3.502 | 11<br>3.429 | 12<br>3.495 | 12<br>3.502 | 12<br>3.167 |
| C | 13<br>3.417 | 13<br>3.470 | 13<br>3.502 | 14<br>3.465 | 14<br>3.502 | 14<br>3.485 | 15<br>3.492 | 15<br>3.470 | 15<br>3.409 | 16<br>3.374 | 16<br>3.498 | 16<br>3.036 |
| D | 17<br>3.313 | 17<br>3.502 | 17<br>3.498 | 18<br>3.428 | 18<br>3.502 | 18<br>3.395 | 19<br>3.502 | 19<br>3.502 | 19<br>3.481 | 20<br>3.434 | 20<br>3.502 | 20<br>3.079 |
| E | 21<br>3.383 | 21<br>3.502 | 21<br>3.502 | 22<br>3.469 | 22<br>3.502 | 22<br>3.502 | 23<br>3.502 | 23<br>3.502 | 23<br>3.390 | 24<br>3.426 | 24<br>3.500 | 24<br>3.106 |
| F | 25<br>0.161 | 25<br>0.158 | 25<br>0.154 | 26<br>0.105 | 26<br>0.104 | 26<br>0.105 | 27<br>0.191 | 27<br>0.220 | 27<br>0.200 | 28<br>1.427 | 28<br>1.415 | 28<br>1.416 |
| G | 29<br>3.354 | 29<br>3.466 | 29<br>3.502 | 30<br>0.158 | 30<br>0.152 | 30<br>0.160 | 31<br>1.990 | 31<br>1.990 | 31<br>1.926 | 32<br>3.447 | 32<br>3.492 | 32<br>3.159 |
| H | 33<br>0.182 | 33<br>0.184 | 33<br>0.180 | 34<br>3.360 | 34<br>3.238 | 34<br>3.273 | | | | | | |

FIG. 11B

11C. Results for R1- (Buffered Saline)

| | 1 | 2 | 3 | 4 | 5 | 6 | 7 | 8 | 9 | 10 | 11 | 12 |
|---|---|---|---|---|---|---|---|---|---|---|---|---|
| A | 5 0.140 | 5 0.119 | 5 0.120 | 6 0.116 | 6 0.109 | 6 0.112 | 7 0.108 | 7 0.107 | 7 0.109 | 8 0.151 | 8 0.129 | 8 0.154 |
| B | 9 0.123 | 9 0.117 | 9 0.110 | 10 0.123 | 10 0.117 | 10 0.122 | 11 0.121 | 11 0.121 | 11 0.122 | 12 0.119 | 12 0.120 | 12 0.122 |
| C | 13 0.126 | 13 0.127 | 13 0.127 | 14 0.116 | 14 0.122 | 14 0.120 | 15 0.129 | 15 0.135 | 15 0.132 | 16 0.126 | 16 0.126 | 16 0.127 |
| D | 17 0.476 | 17 0.339 | 17 0.523 | 18 0.201 | 18 0.202 | 18 0.206 | 19 0.255 | 19 0.252 | 19 0.272 | 20 0.177 | 20 0.181 | 20 0.184 |
| E | 21 0.181 | 21 0.208 | 21 0.173 | 22 0.125 | 22 0.146 | 22 0.148 | 23 0.135 | 23 0.137 | 23 0.140 | 24 0.773 | 24 0.778 | 24 0.787 |
| F | 25 0.110 | 25 0.105 | 25 0.106 | 26 0.099 | 26 0.100 | 26 0.101 | 27 0.089 | 27 0.095 | 27 0.095 | 28 0.119 | 28 0.116 | 28 0.113 |
| G | 29 0.109 | 29 0.116 | 29 0.104 | 30 0.123 | 30 0.113 | 30 0.138 | 31 0.124 | 31 0.117 | 31 0.144 | 32 0.208 | 32 0.199 | 32 0.213 |
| H | 33 0.121 | 33 0.111 | 33 0.111 | 34 0.135 | 34 0.117 | 34 0.129 | | | | | | |

FIG. 11C

11D. Results for R2+ (Alkaline Phosphatase +Ethanol)

| | 1 | 2 | 3 | 4 | 5 | 6 | 7 | 8 | 9 | 10 | 11 | 12 |
|---|---|---|---|---|---|---|---|---|---|---|---|---|
| A | 5 3.415 | 5 3.502 | 5 3.502 | 6 3.502 | 6 3.476 | 6 3.481 | 7 3.502 | 7 3.476 | 7 3.425 | 8 3.389 | 8 3.427 | 8 3.328 |
| B | 9 3.307 | 9 3.502 | 9 3.496 | 10 3.502 | 10 3.502 | 10 3.461 | 11 3.431 | 11 3.502 | 11 3.342 | 12 3.339 | 12 3.463 | 12 3.219 |
| C | 13 3.419 | 13 3.502 | 13 3.467 | 14 3.502 | 14 3.502 | 14 3.397 | 15 3.466 | 15 3.453 | 15 3.371 | 16 3.357 | 16 3.380 | 16 3.223 |
| D | 17 3.402 | 17 3.502 | 17 3.502 | 18 3.502 | 18 3.441 | 18 3.362 | 19 3.467 | 19 3.502 | 19 3.411 | 20 3.375 | 20 3.462 | 20 3.240 |
| E | 21 3.340 | 21 3.502 | 21 3.502 | 22 3.492 | 22 3.502 | 22 3.398 | 23 3.502 | 23 3.481 | 23 3.411 | 24 3.329 | 24 3.421 | 24 3.319 |
| F | 25 0.423 | 25 0.433 | 25 0.429 | 26 0.094 | 26 0.093 | 26 0.094 | 27 3.466 | 27 3.502 | 27 3.381 | 28 3.283 | 28 3.408 | 28 3.220 |
| G | 29 2.926 | 29 2.922 | 29 2.852 | 30 3.502 | 30 3.502 | 30 3.425 | 31 3.444 | 31 3.465 | 31 3.398 | 32 0.509 | 32 0.510 | 32 0.511 |
| H | 33 0.181 | 33 0.179 | 33 0.174 | 34 3.429 | 34 3.249 | 34 3.164 | | | | | | |

FIG. 11D

11E. Results for R2- (Ethanol)

| | 1 | 2 | 3 | 4 | 5 | 6 | 7 | 8 | 9 | 10 | 11 | 12 |
|---|---|---|---|---|---|---|---|---|---|---|---|---|
| A | 5 0.117 | 5 0.109 | 5 0.102 | 6 0.110 | 6 0.096 | 6 0.096 | 7 0.092 | 7 0.092 | 7 0.095 | 8 0.135 | 8 0.129 | 8 0.132 |
| B | 9 0.165 | 9 0.155 | 9 0.168 | 10 0.567 | 10 0.557 | 10 0.582 | 11 0.101 | 11 0.101 | 11 0.102 | 12 0.096 | 12 0.098 | 12 0.097 |
| C | 13 0.142 | 13 0.147 | 13 0.125 | 14 0.098 | 14 0.101 | 14 0.104 | 15 0.118 | 15 0.115 | 15 0.132 | 16 0.096 | 16 0.096 | 16 0.094 |
| D | 17 0.599 | 17 0.570 | 17 0.863 | 18 0.098 | 18 0.099 | 18 0.099 | 19 0.203 | 19 0.346 | 19 0.290 | 20 0.532 | 20 0.519 | 20 0.526 |
| E | 21 0.141 | 21 0.135 | 21 0.129 | 22 0.141 | 22 0.140 | 22 0.135 | 23 0.184 | 23 0.190 | 23 0.187 | 24 0.503 | 24 0.532 | 24 0.546 |
| F | 25 0.101 | 25 0.096 | 25 0.094 | 26 0.096 | 26 0.094 | 26 0.095 | 27 0.091 | 27 0.095 | 27 0.095 | 28 0.104 | 28 0.103 | 28 0.104 |
| G | 29 0.101 | 29 0.096 | 29 0.096 | 30 0.114 | 30 0.104 | 30 0.112 | 31 0.220 | 31 0.138 | 31 0.168 | 32 0.173 | 32 0.173 | 32 0.174 |
| H | 33 0.101 | 33 0.097 | 33 0.094 | 34 0.096 | 34 0.095 | 34 0.085 | | | | | | |

R1+= Phosphate buffered saline + Alkaline phosphatase; R1- = Phosphate buffered saline; R2+= Ethanol + Alkaline phosphatase; R2- = Ethanol

FIG. 11E

12A. Results for aliquoted PNPP in 96-well plate; 30 minutes

| | | | 0.5 mL microcentrifuge tubes | | | | | | 4 mL glass vials | | | |
|---|---|---|---|---|---|---|---|---|---|---|---|---|
| | 1 | 2 | 3 | 4 | 5 | 6 | 7 | 8 | 9 | 10 | 11 | 12 |
| Same stock from 2.1.25 — "A" A | 1 / 3.418 | 1 / 3.338 | 1 / 3.404 | 3 / 0.544 | 3 / 0.484 | 3 / 0.419 | 20 / 2.714 | 20 / 2.449 | 20 / 2.486 | 29 / 1.083 | 29 / 0.997 | 29 / 0.803 |
| B | 32 / 0.597 | 32 / 0.476 | 32 / 0.412 | 34 / 0.747 | 34 / 0.682 | 34 / 0.589 | | | | | | |
| New stock — "B" C | 1 / 3.337 | 1 / 3.502 | 1 / 3.077 | 3 / 0.444 | 3 / 0.388 | 3 / 0.497 | 20 / 3.127 | 20 / 3.416 | 20 / 3.448 | 29 / 0.442 | 29 / 0.419 | 29 / 0.425 |
| D | 32 / 0.109 | 32 / 0.110 | 32 / 0.130 | 34 / 0.797 | 34 / 0.822 | 34 / 0.889 | | | | | | |
| Same stock from 2.1.23 — "A" E | 1 / 3.331 | 1 / 3.316 | 1 / 3.328 | 3 / 0.238 | 3 / 0.267 | 3 / 0.228 | 20 / 0.414 | 20 / 0.474 | 20 / 0.559 | 29 / 0.110 | 29 / 0.104 | 29 / 0.107 |
| F | 32 / 0.132 | 32 / 0.137 | 32 / 0.189 | 34 / 0.131 | 34 / 0.118 | 34 / 0.122 | | | | | | |
| New stock — "B" G | 1 / 3.215 | 1 / 3.272 | 1 / 3.445 | 3 / 1.163 | 3 / 1.229 | 3 / 0.989 | 20 / 2.966 | 20 / 2.799 | 20 / 2.998 | 29 / 0.121 | 29 / 0.121 | 29 / 0.115 |
| H | 32 / 0.116 | 32 / 0.129 | 32 / 0.150 | 34 / 0.165 | 34 / 0.189 | 34 / 0.172 | | | | | | |

FIG. 12A

12B. Results for aliquoted PNPP in 96-well plate; 1-hour

| | | 1 | 2 | 3 | 4 | 5 | 6 | 7 | 8 | 9 | 10 | 11 | 12 |
|---|---|---|---|---|---|---|---|---|---|---|---|---|---|
| Same stock from 2.1.23 — "A" | A | 1 / 3.364 | 1 / 3.432 | 1 / 3.451 | 3 / 0.873 | 3 / 0.769 | 3 / 0.799 | 20 / 2.360 | 20 / 2.539 | 20 / 2.690 | 29 / 1.612 | 29 / 1.507 | 29 / 1.253 |
| | B | 32 / 0.889 | 32 / 0.815 | 32 / 0.825 | 34 / 1.162 | 34 / 1.633 | 34 / 1.090 | | | | | | |
| New stock — "B" | C | 1 / 3.290 | 1 / 3.502 | 1 / 3.502 | 3 / 0.625 | 3 / 0.667 | 3 / 0.623 | 20 / 2.956 | 20 / 2.796 | 20 / 2.902 | 29 / 0.696 | 29 / 0.681 | 29 / 0.619 |
| | D | 32 / 0.114 | 32 / 0.105 | 32 / 0.104 | 34 / 1.280 | 34 / 1.222 | 34 / 1.353 | | | | | | |
| "A" | E | 1 / 3.390 | 1 / 3.171 | 1 / 3.097 | 3 / 0.396 | 3 / 0.429 | 3 / 0.398 | 20 / 0.804 | 20 / 0.852 | 20 / 0.901 | 29 / 0.109 | 29 / 0.109 | 29 / 0.114 |
| | F | 32 / 0.114 | 32 / 0.108 | 32 / 0.111 | 34 / 0.149 | 34 / 0.131 | 34 / 0.138 | | | | | | |
| "B" | G | 1 / 3.021 | 1 / 3.498 | 1 / 3.380 | 3 / 1.963 | 3 / 2.061 | 3 / 1.730 | 20 / 3.483 | 20 / 3.319 | 20 / 3.461 | 29 / 0.142 | 29 / 0.143 | 29 / 0.133 |
| | H | 32 / 0.116 | 32 / 0.116 | 32 / 0.113 | 34 / 0.208 | 34 / 0.252 | 34 / 0.227 | | | | | | |

Rows A–D: 0.5 mL microcentrifuge tubes; Rows E–H: 4 mL glass vials

FIG. 12B

12C. Results for aliquoted PNPP in Glass Vial; 30-minutes

|   | | 1 | 2 | 3 | 4 | 5 | 6 | 7 | 8 | 9 | 10 | 11 | 12 |
|---|---|---|---|---|---|---|---|---|---|---|---|---|---|
| "A" | A | 1 3.197 | 1 3.171 | 1 3.203 | 3 0.816 | 3 0.829 | 3 0.856 | 20 2.622 | 20 2.727 | 20 2.633 | 29 1.799 | 29 1.832 | 29 1.798 |
|  | B | 32 0.899 | 32 0.912 | 32 0.912 | 34 2.478 | 34 2.478 | 34 2.526 | | | | | | |
| "B" | C | 1 3.417 | 1 3.499 | 1 3.475 | 3 1.380 | 3 1.392 | 3 1.427 | 20 3.427 | 20 3.421 | 20 3.387 | 29 1.668 | 29 1.831 | 29 1.847 |
|  | D | 32 0.275 | 32 0.271 | 32 0.277 | 34 3.019 | 34 2.975 | 34 3.027 | | | | | | |

FIG. 12C

12D. Results for aliquoted PNPP in Glass Vial; 1-hour

|   | | 1 | 2 | 3 | 4 | 5 | 6 | 7 | 8 | 9 | 10 | 11 | 12 |
|---|---|---|---|---|---|---|---|---|---|---|---|---|---|
| "A" | A | 1 3.450 | 1 3.502 | 1 3.502 | 3 1.451 | 3 1.464 | 3 1.515 | 20 3.409 | 20 3.432 | 20 3.367 | 29 2.781 | 29 2.834 | 29 2.762 |
|  | B | 32 1.383 | 32 1.407 | 32 1.401 | 34 3.368 | 34 3.352 | 34 3.384 | | | | | | |
| "B" | C | 1 3.496 | 1 3.502 | 1 3.502 | 3 2.469 | 3 2.481 | 3 2.536 | 20 3.502 | 20 3.437 | 20 3.440 | 29 2.650 | 29 2.836 | 29 2.735 |
|  | D | 32 0.311 | 32 0.304 | 32 0.309 | 34 3.437 | 34 3.502 | 34 3.439 | | | | | | |

A = Stock made from previous experiment on 2.1.23; B = New stock made fresh on 2.2.23; PNPP = p-Nitrophenyl phosphate disodium salt

FIG. 12D

13A. Results for Controls

| | 1 | 2 | 3 | 4 | 5 | 6 | 7 | 8 | 9 | 10 | 11 | 12 |
|---|---|---|---|---|---|---|---|---|---|---|---|---|
| A (A1) | 1 - NC1 3.502 | 1 3.502 | 1 3.502 | 2 - NC2 3.502 | 2 3.502 | 2 3.425 | 3 - PC1 0.096 | 3 0.096 | 3 0.096 | 4 - PC2 0.130 | 4 0.125 | 4 0.125 |
| B (B1) | 1 - NC1 0.130 | 1 0.129 | 1 0.131 | 2 - NC2 0.144 | 2 0.144 | 2 0.148 | 3 - PC1 0.096 | 3 0.094 | 3 0.095 | 4 - PC2 0.126 | 4 0.127 | 4 0.125 |
| C (A2) | 1 - NC1 3.451 | 1 3.502 | 1 2.954 | 2 - NC2 3.502 | 2 3.444 | 2 3.326 | 3 - PC1 0.996 | 3 0.724 | 3 0.829 | 4 - PC2 0.466 | 4 0.581 | 4 0.470 |
| D (B2) | 1 - NC1 0.103 | 1 0.100 | 1 0.098 | 2 - NC2 0.119 | 2 0.119 | 2 0.120 | 3 - PC1 0.097 | 3 0.097 | 3 0.100 | 4 - PC2 0.112 | 4 0.120 | 4 0.119 |
| E | | | | | | | | | | | | |
| F | S1 2.567 | S2 2.764 | | | | | | | | | | |
| G | S1 2.614 | S2 2.784 | | | | | | | | | | |
| H | S1 2.552 | S2 2.730 | | | | | | | | | | |

FIG. 13A

13B. Results for Active Buffered Saline Reaction Reagent

| | 1 | 2 | 3 | 4 | 5 | 6 | 7 | 8 | 9 | 10 | 11 | 12 |
|---|---|---|---|---|---|---|---|---|---|---|---|---|
| A | 5 - NC 3.387 | 5 3.502 | 5 3.502 | 6 - NC 3.502 | 6 3.489 | 6 3.498 | 7 - NC 3.484 | 7 3.480 | 7 3.305 | 8 - NC 3.354 | 8 3.441 | 8 3.238 |
| B | 9 - NC 3.373 | 9 3.496 | 9 3.484 | 10 - NC 3.502 | 10 3.444 | 10 3.445 | 11 - NC 3.502 | 11 3.502 | 11 3.403 | 12 - NC 3.412 | 12 3.502 | 12 3.154 |
| C | 13 - NC 3.401 | 13 3.485 | 13 3.502 | 14 - NC 3.502 | 14 3.502 | 14 3.499 | 15 - 2 3.467 | 15 3.474 | 15 3.395 | 16 - 2 3.428 | 16 3.298 | 16 3.056 |
| D | 17 - 2 3.405 | 17 3.502 | 17 3.502 | 18 - 2 3.502 | 18 3.502 | 18 3.502 | 19 - 2 3.502 | 19 3.476 | 19 3.453 | 20 - 2 3.409 | 20 3.131 | 20 3.049 |
| E | 21 - 2 3.406 | 21 3.502 | 21 3.502 | 22 - 2 3.502 | 22 3.502 | 22 3.502 | 23 - 2 3.502 | 23 3.466 | 23 3.380 | 24 - 2 3.393 | 24 3.445 | 24 3.050 |
| F | 25 - 1A 0.118 | 25 0.121 | 25 0.124 | 26 - 1B 0.118 | 26 0.111 | 26 0.112 | 27 - 1BC 0.101 | 27 0.117 | 27 0.135 | 28 - 1BC 0.741 | 28 0.791 | 28 0.860 |
| G | 29 - 1BC 3.423 | 29 3.465 | 29 3.485 | 30 - 1BC 0.437 | 30 0.528 | 30 0.607 | 31 - 1BC 0.211 | 31 0.242 | 31 0.272 | 32 - 1BC 2.141 | 32 2.668 | 32 2.862 |
| H | 33 - 1BC 0.130 | 33 0.132 | 33 0.133 | 34 - 1C 3.265 | 34 3.225 | 34 3.230 | | | | | | |

FIG. 13B

13C. Results for Blank Buffered Saline Reaction Reagent

| | 1 | 2 | 3 | 4 | 5 | 6 | 7 | 8 | 9 | 10 | 11 | 12 |
|---|---|---|---|---|---|---|---|---|---|---|---|---|
| A | 5-NC 0.166 | 5 0.184 | 5 0.191 | 6-NC 0.161 | 6 0.152 | 6 0.150 | 7-NC 0.123 | 7 0.122 | 7 0.120 | 8-NC 0.175 | 8 0.170 | 8 0.169 |
| B | 9-NC 0.131 | 9 0.134 | 9 0.127 | 10-NC 0.151 | 10 0.144 | 10 0.149 | 11-NC 0.130 | 11 0.122 | 11 0.140 | 12-NC 0.123 | 12 0.121 | 12 0.126 |
| C | 13-NC 0.133 | 13 0.121 | 13 0.138 | 14-NC 0.130 | 14 0.133 | 14 0.133 | 15-2 0.139 | 15 0.137 | 15 0.148 | 16-2 0.123 | 16 0.124 | 16 0.125 |
| D | 17-2 0.180 | 17 0.122 | 17 0.121 | 18-2 0.131 | 18 0.131 | 18 0.140 | 19-2 0.127 | 19 0.122 | 19 0.233 | 20-2 0.153 | 20 0.161 | 20 0.136 |
| E | 21-2 0.132 | 21 0.119 | 21 0.120 | 22-2 0.121 | 22 0.119 | 22 0.119 | 23-2 0.131 | 23 0.126 | 23 0.118 | 24-2 0.146 | 24 0.131 | 24 0.124 |
| F | 25-1A 0.124 | 25 0.116 | 25 0.120 | 26-1B 0.110 | 26 0.109 | 26 0.110 | 27-1BC 0.103 | 27 0.102 | 27 0.109 | 28-1BC 0.129 | 28 0.130 | 28 0.133 |
| G | 29-1BC 0.115 | 29 0.110 | 29 0.110 | 30-1BC 0.127 | 30 0.133 | 30 0.119 | 31-1BC 0.122 | 31 0.135 | 31 0.123 | 32-1BC 0.124 | 32 0.129 | 32 0.127 |
| H | 33-1BC 0.115 | 33 0.116 | 33 0.114 | 34-1C 0.123 | 34 0.120 | 34 0.126 | | | | | | |

FIG. 13C

13D. Results for Active Ethanol Reaction Reagent

| | 1 | 2 | 3 | 4 | 5 | 6 | 7 | 8 | 9 | 10 | 11 | 12 |
|---|---|---|---|---|---|---|---|---|---|---|---|---|
| A | 5-NC / 2.948 | 5 / 2.731 | 5 / 2.869 | 6-NC / 2.692 | 6 / 2.767 | 6 / 2.693 | 7-NC / 2.294 | 7 / 2.902 | 7 / 2.389 | 8-NC / 3.379 | 8 / 3.355 | 8 / 3.266 |
| B | 9-NC / 3.413 | 9 / 3.244 | 9 / 3.360 | 10-NC / 3.345 | 10 / 3.272 | 10 / 3.333 | 11-NC / 3.342 | 11 / 3.280 | 11 / 3.287 | 12-NC / 2.513 | 12 / 2.154 | 12 / 3.089 |
| C | 13-NC / 3.420 | 13 / 3.252 | 13 / 3.484 | 14-NC / 2.343 | 14 / 2.467 | 14 / 2.685 | 15-2 / 2.649 | 15 / 2.398 | 15 / 2.368 | 16-2 / 2.590 | 16 / 2.870 | 16 / 2.598 |
| D | 17-2 / 2.736 | 17 / 2.750 | 17 / 2.845 | 18-2 / 2.405 | 18 / 2.471 | 18 / 2.704 | 19-2 / 2.757 | 19 / 2.754 | 19 / 2.868 | 20-2 / 2.730 | 20 / 2.395 | 20 / 2.098 |
| E | 21-2 / 1.876 | 21 / 1.851 | 21 / 1.956 | 22-2 / 2.223 | 22 / 2.751 | 22 / 2.793 | 23-2 / 2.205 | 23 / 2.441 | 23 / 2.472 | 24-2 / 2.496 | 24 / 2.067 | 24 / 2.117 |
| F | 25-1A / 0.119 | 25 / 0.118 | 25 / 0.114 | 26-1B / 0.107 | 26 / 0.109 | 26 / 0.108 | 27-1BC / 2.305 | 27 / 2.035 | 27 / 3.339 | 28-1BC / 2.120 | 28 / 2.776 | 28 / 2.129 |
| G | 29-1BC / 0.226 | 29 / 0.212 | 29 / 0.295 | 30-1BC / 2.829 | 30 / 2.567 | 30 / 2.448 | 31-1BC / 2.462 | 31 / 2.558 | 31 / 2.772 | 32-1BC / 0.170 | 32 / 0.161 | 32 / 0.193 |
| H | 33-1BC / 0.121 | 33 / 0.118 | 33 / 0.127 | 34-1C / 0.588 | 34 / 0.583 | 34 / 0.539 | | | | | | |

FIG. 13D

13E. Results for Blank Ethanol Reaction Reagent

| | 1 | 2 | 3 | 4 | 5 | 6 | 7 | 8 | 9 | 10 | 11 | 12 |
|---|---|---|---|---|---|---|---|---|---|---|---|---|
| A | 5 - NC 0.350 | 5 0.310 | 5 0.325 | 6 - NC 0.108 | 6 0.111 | 6 0.108 | 7 - NC 0.102 | 7 0.105 | 7 0.107 | 8 - NC 0.206 | 8 0.291 | 8 0.240 |
| B | 9 - NC 0.131 | 9 0.126 | 9 0.111 | 10 - NC 0.397 | 10 0.488 | 10 0.509 | 11 - NC 0.116 | 11 0.120 | 11 0.120 | 12 - NC 0.124 | 12 0.123 | 12 0.119 |
| C | 13 - NC 0.193 | 13 0.153 | 13 0.137 | 14 - NC 0.114 | 14 0.111 | 14 0.110 | 15 - 2 0.194 | 15 0.296 | 15 0.174 | 16 - 2 0.232 | 16 0.239 | 16 0.254 |
| D | 17 - 2 0.138 | 17 0.153 | 17 0.144 | 18 - 2 0.143 | 18 0.144 | 18 0.143 | 19 - 2 0.204 | 19 0.198 | 19 0.117 | 20 - 2 0.146 | 20 0.149 | 20 0.154 |
| E | 21 - 2 0.104 | 21 0.105 | 21 0.106 | 22 - 2 0.106 | 22 0.106 | 22 0.108 | 23 - 2 0.107 | 23 0.106 | 23 0.109 | 24 - 2 0.153 | 24 0.176 | 24 0.160 |
| F | 25 - 1A 0.109 | 25 0.108 | 25 0.109 | 26 - 1B 0.108 | 26 0.107 | 26 0.108 | 27 - 1BC 0.111 | 27 0.111 | 27 0.111 | 28 - 1BC 0.154 | 28 0.135 | 28 0.137 |
| G | 29 - 1BC 0.108 | 29 0.107 | 29 0.105 | 30 - 1BC 0.111 | 30 0.109 | 30 0.115 | 31 - 1BC 0.113 | 31 0.108 | 31 0.121 | 32 - 1BC 0.131 | 32 0.124 | 32 0.160 |
| H | 33 - 1BC 0.108 | 33 0.107 | 33 0.106 | 34 - 1C 0.115 | 34 0.110 | 34 0.113 | | | | | | |

S1 = Water/Ink Stock; S2 = Acetic acid/Ink Stock; NC = Not Classified

FIG. 13E

Summary of Results

| Chem No. | A1 AVG ± SE | B1 AVG ± SE | NET1 OD | NET1/NC1 | 1/NET1 | A2 AVG ± SE |
|---|---|---|---|---|---|---|
| 1 | 3.502 ± 0.000 | 0.130 ± 0.001 | 3.372 | 1.000 | 1 | 3.302 ± 0.175 |
| 2 | 3.476 ± 0.026 | 0.145 ± 0.001 | 3.331 | 0.988 | 1 | 3.424 ± 0.052 |
| 3 | 0.096 ± 0.000 | 0.095 ± 0.001 | 0.001 | 0.000 | 1000 | 0.850 ± 0.079 |
| 4 | 0.127 ± 0.002 | 0.126 ± 0.001 | 0.001 | 0.000 | 1000 | 0.506 ± 0.038 |
| 5 | 3.464 ± 0.038 | 0.180 ± 0.007 | 3.283 | 0.974 | 1 | 2.849 ± 0.063 |
| 6 | 3.496 ± 0.004 | 0.154 ± 0.003 | 3.342 | 0.991 | 1 | 2.717 ± 0.025 |
| 7 | 3.423 ± 0.059 | 0.122 ± 0.001 | 3.301 | 0.979 | 1 | 2.528 ± 0.189 |
| 8 | 3.344 ± 0.059 | 0.171 ± 0.002 | 3.173 | 0.941 | 1 | 3.333 ± 0.034 |
| 9 | 3.451 ± 0.039 | 0.131 ± 0.002 | 3.320 | 0.985 | 1 | 3.339 ± 0.050 |
| 10 | 3.464 ± 0.019 | 0.148 ± 0.002 | 3.316 | 0.983 | 1 | 3.317 ± 0.023 |
| 11 | 3.469 ± 0.033 | 0.131 ± 0.005 | 3.338 | 0.990 | 1 | 3.303 ± 0.020 |
| 12 | 3.356 ± 0.104 | 0.123 ± 0.001 | 3.233 | 0.959 | 1 | 2.585 ± 0.272 |
| 13 | 3.463 ± 0.031 | 0.131 ± 0.005 | 3.332 | 0.988 | 1 | 3.385 ± 0.069 |
| 14 | 3.501 ± 0.001 | 0.132 ± 0.001 | 3.369 | 0.999 | 1 | 2.498 ± 0.100 |
| 15 | 3.445 ± 0.025 | 0.141 ± 0.003 | 3.304 | 0.980 | 1 | 2.472 ± 0.089 |
| 16 | 3.261 ± 0.109 | 0.124 ± 0.001 | 3.137 | 0.930 | 1 | 2.686 ± 0.092 |
| 17 | 3.470 ± 0.032 | 0.141 ± 0.020 | 3.329 | 0.987 | 1 | 2.777 ± 0.034 |

Chem. No. = Chemical Number; OD = Optical Density; NCor = Noncorrosive; Cor = Corrosive; TP = True Positive; FN = False Negative; TN = True Negative; TP = True Positive; * = Minimum value is 0.001; SE = Standard Error

FIG. 14

Summary of Results

| B2 AVG ± SE | NET2 OD | NET2/NC2 | 1/NET2 | IC Corrosion Score | Prediction | Concordance with in vivo |
|---|---|---|---|---|---|---|
| 0.100 ± 0.001 | 3.202 | 1.000 | 1 | 1 | NCor | NA |
| 0.119 ± 0.000 | 3.305 | 1.032 | 1 | 1 | NCor | NA |
| 0.098 ± 0.001 | 0.752 | 0.235 | 4 | 1000 | Cor | NA |
| 0.117 ± 0.003 | 0.389 | 0.121 | 8 | 1000 | Cor | NA |
| 0.328 ± 0.012 | 2.521 | 0.787 | 1 | 1 | NCor | TN |
| 0.109 ± 0.001 | 2.609 | 0.815 | 1 | 1 | NCor | TN |
| 0.105 ± 0.001 | 2.424 | 0.757 | 1 | 1 | NCor | TN |
| 0.246 ± 0.025 | 3.088 | 0.964 | 1 | 1 | NCor | TN |
| 0.123 ± 0.006 | 3.216 | 1.004 | 1 | 1 | NCor | TN |
| 0.465 ± 0.034 | 2.852 | 0.891 | 1 | 1 | NCor | TN |
| 0.119 ± 0.001 | 3.184 | 0.994 | 1 | 1 | NCor | TN |
| 0.122 ± 0.002 | 2.463 | 0.769 | 1 | 1 | NCor | TN |
| 0.161 ± 0.017 | 3.224 | 1.007 | 1 | 1 | NCor | TN |
| 0.112 ± 0.001 | 2.387 | 0.745 | 1 | 1 | NCor | TN |
| 0.221 ± 0.038 | 2.250 | 0.703 | 1 | 1 | NCor | TN |
| 0.242 ± 0.006 | 2.444 | 0.763 | 1 | 1 | NCor | TN |
| 0.145 ± 0.004 | 2.632 | 0.822 | 1 | 1 | NCor | TN |

Chem. No. = Chemical Number; OD = Optical Density; NCor = Noncorrosive; Cor = Corrosive; TP = True Positive; FN = False Negative; TN = True Negative; TP = True Positive; * = Minimum value is 0.001; SE = Standard Error

FIG. 14
CONTINUED

Summary of Results

| | | | | | | |
|---|---|---|---|---|---|---|
| 18 | 3.502 ± 0.000 | 0.134 ± 0.003 | 3.368 | 0.999 | 1 | 2.527 ± 0.091 |
| 19 | 3.477 ± 0.014 | 0.161 ± 0.036 | 3.316 | 0.983 | 1 | 2.793 ± 0.038 |
| 20 | 3.196 ± 0.109 | 0.150 ± 0.007 | 3.046 | 0.903 | 1 | 2.408 ± 0.183 |
| 21 | 3.470 ± 0.032 | 0.124 ± 0.004 | 3.346 | 0.992 | 1 | 1.894 ± 0.032 |
| 22 | 3.502 ± 0.000 | 0.120 ± 0.001 | 3.382 | 1.003 | 1 | 2.589 ± 0.183 |
| 23 | 3.449 ± 0.036 | 0.125 ± 0.004 | 3.324 | 0.986 | 1 | 2.373 ± 0.084 |
| 24 | 3.296 ± 0.124 | 0.134 ± 0.006 | 3.162 | 0.938 | 1 | 2.227 ± 0.135 |
| 25 | 0.121 ± 0.002 | 0.120 ± 0.002 | 0.001 | 0.001 | 1000 | 0.117 ± 0.002 |
| 26 | 0.114 ± 0.002 | 0.110 ± 0.000 | 0.004 | *0.001 | 1000 | 0.108 ± 0.001 |
| 27 | 0.118 ± 0.010 | 0.105 ± 0.002 | 0.013 | 0.004 | 250 | 2.560 ± 0.397 |
| 28 | 0.797 ± 0.034 | 0.131 ± 0.001 | 0.667 | 0.198 | 5 | 2.342 ± 0.217 |
| 29 | 3.458 ± 0.018 | 0.112 ± 0.002 | 3.346 | 0.992 | 1 | 0.244 ± 0.026 |
| 30 | 0.524 ± 0.049 | 0.126 ± 0.004 | 0.398 | 0.118 | 8 | 2.615 ± 0.113 |
| 31 | 0.242 ± 0.018 | 0.127 ± 0.004 | 0.115 | 0.034 | 29 | 2.597 ± 0.092 |
| 32 | 2.557 ± 0.215 | 0.127 ± 0.001 | 2.430 | 0.721 | 1 | 0.175 ± 0.010 |
| 33 | 0.132 ± 0.001 | 0.115 ± 0.001 | 0.017 | 0.005 | 200 | 0.122 ± 0.003 |
| 34 | 3.240 ± 0.013 | 0.123 ± 0.002 | 3.117 | 0.924 | 1 | 0.570 ± 0.016 |

Chem. No. = Chemical Number; OD = Optical Density; NCor = Noncorrosive; Cor = Corrosive; TP = True Positive; FN = False Negative; TN = True Negative; TP = True Positive; * = Minimum value is 0.001; SE = Standard Error

FIG. 14
CONTINUED

Summary of Results

| | | | | | | |
|---|---|---|---|---|---|---|
| 0.143 ± 0.000 | 2.383 | 0.744 | 1 | 1 | NCor | TN |
| 0.173 ± 0.028 | 2.620 | 0.818 | 1 | 1 | NCor | TN |
| 0.150 ± 0.002 | 2.258 | 0.705 | 1 | 1 | NCor | TN |
| 0.105 ± 0.001 | 1.789 | 0.559 | 2 | 2 | NCor | TN |
| 0.107 ± 0.001 | 2.482 | 0.775 | 1 | 1 | NCor | TN |
| 0.107 ± 0.001 | 2.265 | 0.707 | 1 | 1 | NCor | TN |
| 0.163 ± 0.007 | 2.064 | 0.644 | 2 | 2 | NCor | TN |
| 0.109 ± 0.000 | 0.008 | 0.003 | 333 | 1000 | Cor | TP |
| 0.108 ± 0.000 | 0.001 | 0.001 | 1000 | 1000 | Cor | TP |
| 0.111 ± 0.000 | 2.449 | 0.765 | 1 | 250 | Cor | TP |
| 0.142 ± 0.006 | 2.200 | 0.687 | 1 | 5 | Cor | TP |
| 0.107 ± 0.001 | 0.138 | 0.043 | 23 | 23 | Cor | TP |
| 0.112 ± 0.002 | 2.503 | 0.782 | 1 | 8 | Cor | TP |
| 0.114 ± 0.004 | 2.483 | 0.776 | 1 | 29 | Cor | TP |
| 0.138 ± 0.011 | 0.036 | 0.011 | 88 | 88 | Cor | TP |
| 0.107 ± 0.001 | 0.015 | 0.005 | 213 | 213 | Cor | TP |
| 0.113 ± 0.001 | 0.457 | 0.143 | 7 | 7 | Cor | TP |

Chem. No. = Chemical Number; OD = Optical Density; NCor = Noncorrosive; Cor = Corrosive; TP = True Positive; FN = False Negative; TN = True Negative; TP = True Positive; * = Minimum value is 0.001; SE = Standard Error

FIG. 14
CONTINUED

List and classifications of Chemicals Tested

| [1,2] Not Classified as an Irritant or Corrosive (NC) |
|---|
| (1) 1-Bromo-4-chlorobutane [6940-78-9]; (2) 1,5-Hexadiene [592-42-7]; (3) Isopropanol [67-63-0]; (4) 4-(Methylthio)benzaldehyde [3446-89-7]; (5) Isopropyl myristate [110-27-0]; (6) Benzyl salicylate [118-58-1]; (7) Phenylethyl alcohol [60-12-8]; (8) Hydroxycitronellal [107-75-5]; (9) Benzyl acetate [140-11-4]; (10) Dipropylene glycol [25265-71-8]; (11) Methyl laurate [111-82-0]; (12) Triethylene glycol [112-27-6]; (13) 10-Undecenoic acid [112-38-9]; (14) n-Butyl propionate [590-01-2]; (15) Benzyl acetone [2550-26-7] |

| [1,2,4,5,6,8,11] Not Classified as a Corrosive (Category 2) |
|---|
| (16) di-n-Propyl disulphide [629-19-6]; (17) 1-Bromopentane [110-53-2]; (18) Cyclamen aldehyde [103-95-7]; (19) cis-Jasmone [488-10-8]; (20) p-Metha-1,8-dien-7-ol [536-59-4]; (21) Heptanal [111-71-7]; (22) trans-3,7-Dimethyl-2,6-octadien-1-ol [106-24-1]; (23) alpha-Terpineol [98-55-5]; (24) 1-Decanol [112-30-1]; (25) Nonyl aldehyde [124-19-6]; (26) 2,4-Dimethylaniline [95-68-1]; (27) Geranyl linalool [1113-21-9]; (28) 1-Bromohexane [111-25-1]; (29) 1,3-Dibromopropane [109-64-9]; (30) 3-Diethylaminopropionitrile [5351-04-2] |

| [1,2,3,7,9,10] Classified as a Corrosive (Category 1BC) |
|---|
| (31) N,N-Dimethylbenzylamine [103-83-3]; (32) Potassium hydroxide (10%) [1310-58-3]; (33) 2-Methylbutryic acid [116-53-0]; (34) Octanoic acid [124-07-02]; (35) Dimethylisopropylamine [996-35-0]; (36) 2-tert-Butylphenol [88-18-6]; (37) 5-Isopropyl-2-methylphenol [499-75-2]; (38) n-Heptylamine [111-68-2]; (39) Methoxy-3-propylamine [5332-73-0]; (40) Hexanoic acid [142-62-1]; (41) Sulfuric acid (10%) [7664-93-9]; (42) Allyl bromide [106-95-6]; (43) Butyric acid [107-92-6]; (44) 55/45 Mixture of Octanoic/Decanoic acids [68937-75-7]; (45) 60/40 Mixture of Octanoic/Decanoic acids [68937-75-7]; (46) 65/35 Mixture of Octanoic/Decanoic acids [68937-75-7]; (47) Heptanoic acid [111-14-8]; (48) Dicyclohexylamine [101-83-7]; (49) Ethanolamine [141-43-5] |

| [2,6,7,8] Classified as an Extreme Corrosive (Category 1A) |
|---|
| (50) Dimethyldipropylenetriamine [10563-29-8]; (51) Acrylic acid [79-10-7]; (52) Diethylaminopropylamine [104-78-9]; (53) Sulfuric acid [7664-93-9]; (54) Dimethyl-n-butylamine [927-62-8]; (55) 2-Bromobutane [78-76-2]; (56) 1,2-Diaminopropane [78-90-0]; (57) Formic acid [64-18-6]; (58) Tallow amine [61790-33-8]; (59) Dichloroacetyl chloride [79-36-7]; (60) Bromoacetic acid [79-08-3] |

1 = Han et al., 2021; 2 = Alépée et al., 2019; 3 = Desprez et al., 2015; 4 = Japan MHLW; 5 = OECD TG 439, 2021; 6 = ECHA C&L Inventory; 7 = ICCVAM & NICEATM, 2014; 8 = PubChem; 9 = ICCVAM & NICEATM, 2012; 10 = NICEATM, 2023; 11 = ECETOC, 1995.

FIG. 16

High Throughput Kit Directional Insert

In Chemico Skin Corrosion Test - High Throughput Protocol

Kit Contents

| Materials Supplied with the kit | Equipment and Materials Required but not Supplied |
|---|---|
| • A1: Active test matrix 1 (10 mL)<br>• B1: Blank (Inactive) test matrix 1 (10 mL)<br>• A2: Active test matrix 2 (10 mL)<br>• B2: Blank (Inactive) test matrix 2 (10 mL)<br>• NC (Negative Control): Distilled Water (2 mL)<br>• DR (Detection Reagent) (100 mL) | • Plate reader with 405nm filter<br>• PC (Positive Control): Glacial Acetic Acid, CASRN 64-19-7<br>• 0.5-mL tubes<br>  ○ Thermo Scientific$^{TM}$ Snap Cap Low Retention Microcentrifuge Tubes, Catalog No. 3446PK, or equivalent<br>• Flat bottom 96-well ELISA plate<br>  ○ Corning$^{TM}$ Costar$^{TM}$ 96-well microplate, Catalog No. 09-761-145, or equivalent ELISA plate |

Protocol

1. For each test substance, the negative control (NC), and the positive control (PC), uniquely label four 0.5-mL reaction tubes to distinguish the four test matrix reagents (A1, B1, A2, B2). Add 180 μL of the appropriate test matrix reagent to each of the corresponding labeled reaction tubes. Add test substance(s) and controls to the reaction tubes as follows:
   a. Add 20 μL of distilled water to each NC tube.
   b. Add 20 μl of Glacial Acetic Acid (CASRN 64-19-7, not supplied) to each PC tube.
   c. Add 20 μL (or 20 mg) if solid) of test substance to each corresponding labeled tube. Repeat for each additional test substance.
2. Mix the contents of each reaction tube via pipette by aspirating and dispensing 5 times. Close caps.
3. Incubate capped tubes at room temperature for 4 hours +/- 10 min.
4. While the reaction tubes are incubating, prepare a 96-well ELISA plate by aliquoting 200 μL Detection Reagent solution into each well.
5. After the 4-hour incubation, re-mix the contents of each reaction tube via pipette by aspirating and dispensing 5 times. Add 20 μL aliquots of each reaction (in triplicate wells) to the ELISA plate.
6. Incubate the ELISA plate at room temperature for 1 hour +/- 10 min.
7. Measure the optical density (OD) at 405 nm using a plate reader.
8. Calculate the Test Matrix Percentages for Test Matrix 1 and Test Matrix 2:
   a. Calculate each NC NET OD value (for both Test Matrix 1 and Test Matrix 2) by subtracting the average (of the triplicate aliquots) of the Blank (B) from the average (of the triplicate aliquots) Active (A) OD results.
      i. NC NET OD 1 = A1 - B1 (for Negative Control)
      ii. NC NET OD 2 = A2 - B2 (for Negative Control)
   b. Calculate each Test Substance NET OD value (for both Test Matrix 1 and Test Matrix 2) by subtracting the average (of the triplicate aliquots) of the Blank (B) from the average (of the triplicate aliquots) Active (A) OD results.
      i. Test Substance NET OD 1 = A1 - B1 (for tested material)
      ii. Test Substance NET OD 2 = A2 - B2 (for tested material)

FIG. 17 c. Calculate the Test Matrix Percentages by dividing each NET OD into the respective average (of the triplicate aliquots) NC (Negative Control) OD value.
    i. (Test Substance NET OD 1 / NC NET OD 1) x 100 = Test Matrix 1 percentage (for tested material)
    ii. (Test Substance NET OD 2 / NC NET OD 2) x 100 = Test Matrix 2 percentage (for tested material)

9. Compare the Test Matrix 1 and Test Matrix 2 percentages to the Prediction Model: If both are ≥ 40%, the test substance is predicted to be noncorrosive. If either or both Test Matrix Percentages (Test Matrix 1 percentages and/or Test Matrix 2 percentages) are < 40%, the test substance is predicted to be corrosive.

Prediction Model

| Prediction | Normalized Result |
|---|---|
| Noncorrosive | ≥ 40% |
| Corrosive | < 40% |

10. Quality Control:
    a. Calculate each PC NET OD value (for both Test Matrix 1 and Test Matrix 2) by subtracting the average (of the triplicate aliquots) of the Blank (B) from the average (of the triplicate aliquots) Active (A) OD results.
       i. PC NET OD 1 = A1 - B1 (for Positive Control)
       ii. PC NET OD 2 = A2 - B2 (for Positive Control)
    b. Calculate the Test Matrix Percentages by dividing each NET OD into the respective average (of the triplicate aliquots) NC (Negative Control) OD value.
       i. (PC NET OD 1 / NC NET OD 1) x 100 = Test Matrix 1 percentage
       ii. (PC NET OD 2 / NC NET OD 2) x 100 = Test Matrix 2 percentage
    c. If the Positive Control score is ≥ 25%, the test has failed quality assurance.

Lebrun Labs LLC | 3301 E. Miraloma Ave., Suite 194, Anaheim, CA 92806

FIG. 17
CONTINUED

Predictivity Results

| Accuracy | 98.3% (59/60) |
|---|---|
| Sensitivity | 100% (30/30) |
| Specificity | 96.7% (29/30) |
| FPR | 3.3% (1/30) |
| FNR | 0.0% (0/30) |
| WLR | 100.0% (180/180) |

FPR = False positive rate; FNR = False negative rate;
WLR = Within lab repeatability

FIG. 19

IN CHEMICO TEST FOR TOXICITY

CROSS-REFERENCE TO RELATED APPLICATIONS

This application is a U.S. national stage entry under 35 U.S.C. § 371 of PCT International Patent Application No. PCT/US2024/015781, filed Feb. 14, 2024, which claims benefit of U.S. Provisional Application No. 63/448,157, filed Feb. 24, 2023, the contents of each of which are hereby incorporated by reference.

BACKGROUND

Chemical toxicity testing often involves live animals. However, live animals have limitations with respect to study costs, procurement and duration of studies, subjective evaluation, variability of animal responses and concerns about ethics, animal suffering and new laws banning animal testing for many applications.

For example, many different animal species have been used for the determination of toxicity for different target organs. Eye toxicity studies have been conducted on rabbits (Draize et al., 1944), skin toxicity studies have also been conducted on rabbits (Draize et al., 1944), skin sensitization studies have been conducted on guinea pigs (Robinson et al., 1990), pulmonary inhalation toxicity studies have been conducted on rats, guinea pigs, dogs, monkeys, and hamsters (Phalen, 1976; Robinson et al., 1990), acute toxicity studies have been conducted on rats (Bartsch et al., 1976), hepatotoxicity studies have been conducted on different rat species (Kikkawa et al., 2006), renal toxicity studies have been conducted on rabbits and rats (Mengs and Stotzem, 1993; Pettersson et al., 2002), cardiotoxicity studies have been conducted on rabbits, dogs, and monkeys (Lamberti et al., 2014), and neurotoxicity studies have been conducted on rats (Costa, 1998).

Modern toxicity classification systems are based on benchmark animal toxicity data to develop toxicity categories. Modern classification schemes include the European Union (EU), Globally Harmonized System of classification and labeling of chemicals (GHS), and the Environmental Protection Agency (EPA) systems.

GHS system for eye: For eye toxicity, the GHS categories include NC (not classified as an irritant), Category 2A (reversal by 7 days), Category 2B (reversal by 14 days), and Category 1 (no reversal by 21 days) (EC, 2008b; UN, 2021).

GHS system for skin: For skin toxicity, the GHS categories include Category 3 (mild irritation; mean score of ≥1.5 and <2.3 for erythema/eschar or for oedema in at least 2 of 3 animals at 24, 48, and 72 hours), Category 2 (irritation; mean score of ≥2.3 and ≤4.0 for erythema/eschar or for oedema in at least 2 of 3 tested animals at 24, 48, and 72 hours or inflammation that persists to the end of 14 days), and Category 1 (corrosive; necrosis in at least one tested animal after exposure for ≤4 hours) (UN, 2021). Category 1 can be broken down into three sub-categories: Category 1A (corrosive responses in at least one animal during exposure period of ≤3 min), Category 1B (corrosive responses in at least one animal during exposure period of ≤1 hour), Category 1C (corrosive responses in at least once animal during exposure period of ≤4 hours) (UN, 2021). For skin sensitization, the GHS categories include Category 1, which is divided into Category 1A (substances showing a high frequency of occurrence in humans or animals) or Category 1B (substances showing a low to moderate frequency of occurrence in humans or animals) (UN, 2021).

GHS system for lungs: For acute toxicity (inhalation), the GHS categories include Category 1 (gases [ppmV]: acute toxicity estimate [ATE]≤100; vapors [mg/l]: ATE≤50; dusts and mists (mg/l): ATE≤0.05), Category 2 (gases [ppmV]: 100<ATE≤500; vapors [mg/l]: 0.5<ATE≤2.0; dusts and mists (mg/l): 0.05<ATE≤0.5), Category 3 (gases [ppmV]: 500<ATE≤2,500; vapors [mg/l]: 2.0<ATE≤10.0; dusts and mists (mg/l): 0.5<ATE≤0.1), Category 4 (gases [ppmV]: 2,500<ATE≤20,000; vapors [mg/l]: 10<ATE≤20.0; dusts and mists (mg/l): 1.0<ATE≤5.0), and Category 5 (gases [ppmV]: ATE>20,000; vapors [mg/l]: ATE>20.0; dusts and mists (mg/l): ATE>5.0) (UN, 2021). For respiratory sensitizers, the GHS classes include Category 1, which is divided into Category 1A (substances showing a high frequency of occurrence in humans or animals) or Category 1B (substances showing a low to moderate frequency in humans or animals). (UN, 2021).

GHS system for acute toxicity: For acute toxicity (oral; mg/kg bodyweight), the GHS categories include Category 1 (ATE≤5), Category 2 (5<ATE≤50), Category 3 (50<ATE K 300), Category 4 (300<ATE K 2,000), and Category 5 (2,000<ATE K 5,000) (UN, 2021). For acute toxicity (dermal; mg/kg bodyweight), the GHS Categories include Category 1 (ATE≤50), Category 2 (50<ATE≤200), Category 3 (200<ATE K 1,000), Category 4 (1,000<ATE K 2,000), and Category 5 (2,000<ATE≤5,000) (UN, 2021).

Toxicity classification is used to satisfy U.S. Food and Drug Administration and international safety labeling requirements and plays an important role in commercial product liability and consumer product satisfaction. Guidance documents produced by the Organization for Economic Trade and Development (OECD) are available to coordinate international trade. The OECD describes the standard toxicity tests, which are required for safety data sheet documentation accompanying hazardous chemicals and products. OECD accepted toxicity tests are separated by target tissue and type of test; in vivo (live animal), ex vivo (animal tissue, for example eyes, skin or lung from the meat industry), in vitro (cells in culture, includes monolayer and 3 dimensional cultures of primary or immortalized cells) and in chemico (cell free, test matrix is chemicals and purified and semi purified macromolecules).

In-vivo test methods include the Draize eye and skin irritation test (Draize et al., 1944; OECD, 2015a, 2021a), Human Patch Test (4-h HPT) (York et al., 1996), Local Lymph Node Assay (LLNA) (Gerberick et al., 2007; OECD, 2010), Guinea Pig Maximization Test (GPMT) and Buehler test (Phalen, 1976; Robinson et al., 1990; OECD, 2022a)

Ex-vivo test methods include Bovine Corneal Opacity and Permeability (BCOP) (OECD, 2020a), Isolated Chicken Eye (ICE) (OECD, 2018), Hen's Egg Test-Chorioallantoic Membrane (HET-CAM) (ICCVAM, 2010), Ex Vivo Human Skin (Eberlin et al., 2021), Porcine Corneal Ocular Reversibility (Piehl et al., 2011), and Ex Vivo Eye Irritation Test (Spoler et al., 2015).

In-vitro test methods include the Transcutaneous Electrical Resistance Test (TER) (OECD, 2015b), Human Skin Model Test (OECD, 2004), 3T3 Neutral Red Uptake (NRU) (OECD, 2019a), Reconstructed Human Epidermis (RhE; EpiSkin™, EpiDerm™ Skin Irritation Test [SIT], SkinEthic™ RHE, LabCyte EPI-MODEL24 SIT, epiCS®, Skin+®, KeraSkin™ SIT) (OECD, 2021b), Fluorescein Leakage (FL) (OECD, 2017), Short Time Exposure (STE) (OECD, 2020b), Reconstructed Human Cornea-like Epithelium (RhCE; EpiOcular™ Eye Irritation Test [EIT], SkinEthic™ Human Corneal Epithelium [HCE] EIT, LabCyte CORNEA-MODEL24EIT, MCTT HCE™ EIT] (OECD, 2019b), ARE-Nrf2 Luciferase Test (OECD, 2022c), and Human Cell Line Activation Test (h-CLAT) (OECD, 2022d)

In-chemico test methods include the Direct Peptide Reactivity Assay (DPRA) (OECD, 2022b), Ocular Irritection® (OECD, 2019c), OptiSafe™ (Choksi et al., 2020; Lebrun et al., 2021a, 2021b, 2022, 2023a, 2023b), and Corrositex® (OECD, 2015c; Ulmer and Wang, 2017).

In-Vivo Toxicity Tests

The Draize in vivo eye test is used to predict eye irritation and corrosion potential through exposure of a test substance on the eyes of live White New Zealand rabbits (Draize et al., 1944; OECD 2021a). The test substance is applied to the conjunctival sac of one eye while the other is an untreated control. Then evaluations of the rabbit's conjunctiva, cornea, and iris are made a 1, 24, 48, and 72 hours after exposure and sometimes at 7 and 21 days, if necessary (OECD, 2021a).

The Draize in vivo skin test is used to predict skin irritation and corrosion potential through exposure of a test substance on the skin of live White New Zealand rabbits (Draize et al., 1944; OECD, 2015). The test substance is applied to the shaved skin of the rabbits (typically 3-6) and covered with a gauze patch for 4 hours and then evaluated at 60 minutes, 24, 48, and 72 hours after removing the patch for the potential of a chemical to damage skin by measuring the clinical grading of erythema and eschar formation and oedema formation based on a scale of severity (OECD, 2015). Dermal irritant chemicals cause a reversible redness and swelling after the application of a test substance for up to 4 hours (OECD, 2015). Dermal corrosive chemicals result in necrosis through the epidermis into the dermis in at least one animal after exposure up to 4 h.

The Human Patch Test (4-h HPT) is a human clinical test. To test for skin irritation, the test substance is applied through a patch on the volunteer's upper arm. Irritation potential is assessed and a positive test is defined as localized erythema reaction, scoring according to convention at 24, 48, and 72 hours after removing the patch; "+" (weak: erythema, maybe papules), "++" (strong: vesicles, infiltration) or "+++" (extreme: bullous) excluding "?+" (doubtful: faint erythema only) (York et al., 1996). For ethical reasons the 4-h HPT testing is not used to identify dermal corrosives.

The Local Lymph Node Assay (LLNA) evaluates the skin sensitization potential of a test substance as an alternative to the guinea pig assays (Guinea Pig Maximization Test or Buehler Test). The test substance is applied to the animal's ears (dorsum) for 3 consecutive days and monitored daily for any response, then the animals are rested for 2 days and thymidine is injected into the tail and are returned to their cases to rest for 5 hours before euthanizing. The lymph nodes are excised to be processed and results are calculated by measuring the total disintegrations per minute for each node (Gerberick et al., 2007; OECD, 2010).

In Chemico (Cell Free) Toxicity Tests

Current in chemico tests include the Direct Peptide Reactivity Assay (DPRA) for identification of skin sensitizers (an allergic response following skin contact with the tested chemical), and the Macromolecular Eye Irritation Test (which includes the OptiSafe Eye Irritation Test™ we have developed and another eye test, Ocular Irritection®) (OECD, 2019c; Choksi et al., 2020) and the Corrositex® test for skin corrosives. None of these use enzymes or measure enzymatic activity (OECD, 2015c, 2019c; Choksi et al., 2020).

The Direct Peptide Reactivity Assay (DPRA) in chemico test models the molecular initiating event of the skin sensitization by measuring the binding by chemicals towards model synthetic peptides containing either Lysine or Cysteine. When these peptides are bound by the chemical under evaluation, the peptides have a different HPLC elution profiles. The remaining concentration of unmodified (unbound by the chemical under evaluation) Cysteine- or Lysine-containing following a 24-hour incubation is used to predict the sensitization (Roberts, 2022; OECD, 2022c). This test predicts the ability to illicit an allergic response, presumably because the modified amino acids are no longer recognized, and the immune system becomes stimulated and response to modified proteins, but since part of these protein are part of the organism, the immune system starts to attack its own tissues resulting in an allergic response following exposure to the chemical (Roberts, 2022; OECD, 2022c). The unmodified peptide concentration is measured by high-performance liquid chromatography (HPLC) with elution at 220 nm; no enzymatic activity is measured or involved in the test. Cysteine- and Lysine peptide depletion values are then used in a prediction model which predicts if the chemical is a sensitizer or a non-sensitizer (Roberts, 2022; OECD, 2022c). No enzymes are evaluated or used for the DPRA.

The Macromolecular Eye Irritation test methods are in-chemico methods that uses a set of multiplexed biochemical tests to assess eye irritation potential. The multiplex design allows the identification of chemicals within 24 hours. To conduct the test, the test chemical is applied to macromolecules and the effects are quantified using a spectrophotometer. The optical density (OD) values are used to provide estimates of the chemical's potential to cause eye injury (Choksi et al., 2020; Lebrun et al., 2021a, 2021b, 2022, 2023a, 2023b). No enzymes are evaluated during the macromolecular tests.

The Corrositex® test measures the time it takes for a chemical to be tested to move through a synthetic biobarrier (OECD, 2015c). This test system is comprised of two components, a synthetic macromolecular biobarrier and a chemical detection system (CDS). The time to move through the biobarrier is determined by setting a timer and waiting until the pH indicator dyes on the other side from where the chemical was applied change color. The corrosivity potential of a test chemical is determined by its ability to destroy the biobarrier, which can be seen through a color change as the pH changes to below 4.5 or above 8.5. Three factors are taken into consideration: strength of acid or base, rate of diffusion, and rate of biobarrier destruction (Ulmer and Wang, 2017). No enzymes are used or evaluated for the Corrositex® test.

Live Cell Enzyme and Activity Tests

The MTT (3-(4,5-Dimethylthiazol-2-yl)-2,5-Diphenyltetrazolium Bromide) assay can be used to measure live cell metabolic activity to determine if a cell is alive. If there is sufficient reduced cofactors related to energy metabolism (NADH, NADPH), MTT is reduced resulting in a "positive" MTT reaction (purple precipitate forms within cells) indicating that the cell are viable (are actively metabolizing and producing reduced cofactors). The higher the MTT signal, there more viable ("alive") the cell culture is. Hence, MTT is a positive correlate with cell viability and has in inverse relationship with toxicity. MTT is a positively charged mono-tetrazolium salt that when reduced, forms a violet-blue molecule called formazan which can be quantified using a spectrophotometer at an optical density wavelength of 570 nm (Ghasemi et al., 2021). While cellular enzymes are involved, the critical variable is if the whole cell is alive and actively metabolizing and producing energy stored as reduced cofactors (NADH, NADPH).

The Neutral Red assay can be used to measure cell viability and toxicity by quantifying a viable cell's ability to accumulate neutral red with a spectrophotometer at an optical density wavelength at 540 nm (Repetto et al., 2008). The accumulation of neutral red is depended on active (requires cellular stored energy in the form of ATP) pumping of neutral red into the cell. This test determine if the cell is viable. While enzyme are included, the test is depend on viable cell that can accumulate neutral red within it membranes by active pumping.

The Resazurin assay can be used to monitor viable cells through reduction of resazurin to resorufin, which turns fluorescent pink and can be quantified using a spectrophotometer at an optical density wavelength of 590 nm (Riss et al., 2013). Like MTT this test determines the reducing power of the cell, and hence is related to energy metabolism and only occurs in "viable" (live) cell.

The Protease Viability Marker assay can be used to measure viable cells by adding a substrate that can selectively detect protease activity from viable cells, called glycylphenylalanyl-aminofluorocoumarin (GF-AFC). This substrate penetrates live cells and gets converted by cytoplasmic aminopeptidase to form a fluorescent aminofluorocoumarin that can be quantified using a spectrophotometer at an optical density wavelength of 505 nm (Riss et al., 2013). This test only works with live cells.

Dermal corrosion is defined as direct chemical reactivity on living skin that results in its disintegration and necrosis through the epidermis and into the dermis. Dermal corrosion likely results from abroad range of chemical mechanisms, however the details of how chemicals disintegrate the skin resulting in corrosion are not fully defined. Symptoms of dermal corrosion are referred to clinically as chemical burns, and include vesication (blistering), desiccation (loss of fluids), necrotic tissue, scarring, ulcers, bleeding, bloody sabs, discoloration, and alopecia (OECD, 2015a; Koh et al., 2017). On the other hand, skin irritants are substances that cause temporary changes to the skin with symptoms that include itching, burning sensation, and erythema (OECD 2015; Kose et al., 2018).

Corrosive skin chemicals are classified as Category 1 (corrosive; necrosis in at least one tested animal after exposure for ≤4 hours) (UN, 2021), but contain three subcategories: Category 1A (corrosive responses in at least one animal during exposure period of ≤3 min), Category 1B (corrosive responses in at least one animal during exposure period of ≤1 hour), Category 1C (corrosive responses in at least once animal during exposure period of ≤4 hours) (UN, 2021).

Exposure to dermal corrosives occurs during production, transport, use, and disposal of chemicals and products. Materials are manufactured and transported from all over the world to different destinations and the transport of dangerous goods increases the likelihood of an accident that may cause skin injuries through improper chemical release. During 1999 to 2008, 57,975 chemical release incidents were reported to the Hazardous Substances Emergency Events Surveillance (HSEES) system that was operated by the Centers for Disease Control (CDC) Agency for Toxic Substances and Disease Registry and during this time period there were 13,196 persons reported chemical release-related injuries (Orr et al., 2015). The U.S. Bureau of Labor Statistics reports that chemical burns occurred for every 1 per 10,000 full-time worker and accounted for 0.6% of all occupational injuries (Koh et al., 2017). In a 2015 study on the severity and prevalence of chemical burns, it was found that "despite only making up 3% of a particular burn center's admission, chemical burns were responsible for up to 30% of burn-related deaths" (Robinson and Chhabra, 2015).

Product and chemical testing to determine dermal corrosion potential reduces human suffering and saves lives because testing allows for correct safety labeling so that people can take adequate precautions to avoid injury. Current test methods to identify skin corrosives are all lab tests that take days-weeks (are these all "lab tests" are there any other tests, any rapid field tests for dermal corrosion?).

With additional testing corrosivity can be further divided into three subcategories: 1A (responses after up to 3 minutes exposure and up to 1 hour observation, 1B (responses for exposures between 3 minutes and 1 hour and observations up to 14 days, and 1C (responses that occur after exposures between 1 hour and 4 hours and observations up to 14 days) (UN, 2021).

According to the Code of Federal Regulations (CFR), corrosive substances are considered "Class 8" which is defined as a corrosive material that causes full thickness destruction of human skin at the site of contact and are assigned as I, II, or III. Packing Group I is assigned to test substances that cause irreversible damage to intact skin tissue starting after 3 minutes of exposure or less (49 CFR Part 173 Subpart D, 2023). Packing Group II is assigned to test substances that cause irreversible damage to intact skin tissue after 3 minutes of exposure but not more than 60 minutes (49 CFR Part 173 Subpart D, 2023). Packing Group III is assigned to test substances that cause irreversible damage to intact skin tissue after 60 minutes of exposure but not more than 4 hours (49 CFR 173 Subpart D). Packing Groups I, II, and III are equivalent to GHS Categories 1A, 1B, and 1C, respectively (Alépée et al., 2014).

Corrosive substances are labelled "Category 1". This category contains three optional subcategories which correspond to the UN Packing Groups I, II and III for the transport of goods. The subcategories are implemented in the EU. They differ with regard to the exposure times required to cause skin corrosion in the rabbit and are referred to as 1A ("strong corrosive"), 1B ("moderate corrosive") and 1C ("mild corrosive") (UN, 2021).

At present, there are a limited number of nonanimal tests for dermal corrosion that have been recognized by the Organization for Economic Cooperation and Development (OECD) for which test guidelines have been established. Each of these tests have been validated by comparing the in vitro corrosivity prediction with Draize data results for the same chemicals. These tests include the in vitro Membrane Barrier (OECD 435), Transcutaneous Electrical Resistance (TER; OECD 430) and Reconstructed Human Epidermis (RhE; OECD 431, 439) tests.

The Transcutaneous Electrical Resistance (TER) test measures the skin corrosion potential of a test chemical by evaluating the transcutaneous electrical resistance of rat skin and its ability to produce a loss of normal stratum corneum and barrier function (OECD, 2015b). The test chemical (150 μL) is applied to three rat skin discs for up to 24 hours at 20-23° C. and then removed with tap water and results are quantified by using a low-voltage, alternating current Wheatstone bridge (OECD, 2015b). In addition, if the resistance is below 5 kΩ then the dye, sulforhodamine B, is added to the skin to determine if the stratum corneum is disrupted by measuring the penetration (OECD, 2015b). A validation study (with the modifications to reduce false-positives) demonstrated wide applicability to a range of chemicals and could distinguish between non-corrosives and corrosives. The predictivity statistics include sensitivity of 94% (51/54), specificity of 71% (48/68), accuracy of 81%

(99/122), and balanced accuracy of 82.5% (OECD, 2015b). Like the in vitro Membrane Barrier Test (OECD, 2015c), to order rats and prepare the skin discs and conduct the test has a turnaround time of days to weeks. This is not a rapid field test, this is not an in chemico test and no enzymes are involved with this test.

The Reconstructed Human Epidermis (RhE) Test Method models the epidermis of human skin. Keratinocyte on a solid support are induced to differentiate at the air/liquid interface using a variety differentiation factors ad methods. The 5 commercially available skin corrosion RhE test methods are EpiSkin™, EpiDerm™ Skin Corrosion Test, SkinEthic™ RHE, epiCS®, and LabCyte EPI-MODEL24 SCT. The accuracy is 78.8% is EpiSkin™, 74.2% for EpiDerm™ SCT, 70.0% for SkinEthic™ RHE, 69.8% for epiCS®, and 76.45 for LabCyte EPI-MODEL24 SCT (OECD, 2019). For all RHE tests, tissues are exposed for 3 minutes and 1 hour, with an additional exposure time of 4 hours in the EpiSkin model. The MTT viability assay is used to quantify cell viability and results are compared to a set of standard chemicals to determine corrosion potential. However, this is only a model of the epidermis which may account for the low accuracy (see above). FC To order the tissues and conduct the test (or ship material to be tested to a lab), has a turnaround time of days-weeks. This is not a rapid field test and uses live cell viability as a measure of toxicity; it is not an in chemico test.

The current in chemico tests and toxicity prediction strategies do not measure acellular or dead cell enzymatic activity to predict toxicity.

SUMMARY

The current disclosure provides methods and, kits and compositions that overcome limitations of the prior art.

The current cell based tests use enzymes produced in real time by the live cells, and if this activity is reduced, it indicates the cell is less viable. In other words, these tests measure the transition from "alive" to "dead". Cell and tissue based assays do not start with dead cells or purified or semi purified enzymes.

One of the needs for nonanimal safety tests originated from bans or pending bans on the use of animals for the safety of cosmetics and other products. The EU banned animal testing of finished cosmetic products in 2004, animal-tested ingredients 4 years later, and the transport and sale of cosmetics containing ingredients tested on animals in 2013, pledging to push other parts of the world to accept alternatives (Kanter, 2017). As of 2014, there are bans or severe limitations in Norway, Israel, India, and Brazil (Senate Joint Resolution 22, 2014), and by 2017, the list of countries had grown to 37, according to the Humane Society of the U.S. (Humane Society, 2017).

The United States has been slow to ban animal testing or mandate the use of nonanimal alternatives in the product testing industry; however, recent legislation will ban animals for a wide range of testing applications that have traditionally used live animals. Bill H.R.2790 "The Humane Cosmetics Act" was introduced on Jun. 6, 2017 and would prohibit animal testing of cosmetics within 1 year and the sale or transport of cosmetics tested on animals within 3 years after enactment, which is now supported by more than 200 cosmetics companies and stakeholders (H.R.4148, 2014). Additionally, the "Frank R. Lautenberg Chemical Safety for the 21st Century Act"—S.697, which revises the Toxic Substances Control Act of 1976 (TSCA)—was passed on Jun. 22, 2016. The TSCA now requires EPA to evaluate existing and new chemicals to determine whether regulatory control of a certain chemical is warranted and if it presents an unreasonable risk of injury to health or the environment so as to reduce risks to a reasonable level. The law also requires EPA to "reduce and replace, to the extent practical . . . the use of vertebrate animals in testing chemicals to provide information of equivalent or better scientific quality and relevance for assessing risks of injury to health or the environment of chemical substances or mixtures . . . " and to develop a strategic plan within 2 years of enactment or by June 2018 (S.697, 2016). Section 4 of the new law includes specific guidance on the use of nonanimal tests when available for initial screening and tiered testing of chemical substances and mixtures (S.697, 2016). Therefore, an accurate and internationally accepted nonanimal test for ocular irritation is needed.

In light of these issues, increased interest has focused on the development of nonanimal testing methods and strategies to replace live animal testing. Toward this end, the Interagency Coordinating Committee for the Validation of Alternative Methods (ICCVAM) and the European Centre for Validation of Alternative Methods (ECVAM) conducted retrospective evaluations of data available nonanimal test methods. Based on these retrospective evaluations, the predictive performance of all individual test methods was not felt to be sufficient for any one test, or group of tests, to fully replace the live animal tests (ICCVAM, 2009). ICCVAM and ECVAM did, however, accept Acute Toxicity, BCOP, Cytosensor Microphysiometer (CM), FL, HET-CAM, ICE, Isolated Rabbit Eye (IRE), EpiSkin™, EpiDerm™, EpiOcular™, SkinEthic™ HCE Transcutaneous Electrical Resistance (TER), and Corrositex®.

No single nonanimal test, or combination of nonanimal tests, can currently detect GHS-classified all levels of toxicity (Wilson et al., 2015). There have been new advances with tiered testing that suggests the combination of different validated test methods to accurately classify test substances and replace bottom-up or top-down testing strategies (Scott et al., 2010; Valadares et al., 2021), such as STE and BCOP (Hayashi et al., 2012; Alépée et al., 2019a), RhCE methods and BCOP (Alépée et al., 2019b), or a combination of all three (Hayashi et al., 2012b).

Overall, there are a limited number of types of tests that do not require the use of animals. These tests include animal or microbial cell culture-based tests (in vitro), tests based on excised animal tissue (ex vivo), egg-based tests (organotypic), and non-enzymatic tests (the current in chemico tests). In vitro, ex vivo and organotypic testing matrices are "black box" systems. for the most part, the molecular events that result in the measured response are not known and the relationship to the different responses observed in vivo is not clear; and based on correlation. In addition, The lack of understanding of the underlying reasons why some substances are much more damaging than others has hindered the development of nonanimal tests for eye safety testing. Those familiar with the state of the art strongly support the use of differentiated live tissues, because these in vitro tests systems appear like the tissues that are evaluated in vivo. In general, the most significant developments in the last 20 years of toxicity testing have focused on in vitro, live cell based approaches. Nonetheless, in vitro cell based approaches are still for the most part correlative, because the clinical observations for benchmark in vivo data is not present, and instead another measurement is taken (for example the viability of the cells), cells grown or differentiated in the lab may have very different expression profiles and viabilities, because cells and tissues gown in the lab are maintained under high, artificial growth stimulation by a variety of poorly defined functionality hormones and co-factors, and most importantly in vitro cell and tissue tests are not shelf stable and are generally slow and expensive. However, as mentioned above, those familiar with the state of the art have almost exclusively focused on ex vivo, in vitro live cell and tissue culture approaches, and those familiar with the art would likely argue against using puri-fied or semi purified enzymes to test for general toxicity endpoints (versus specific pharmaceutical receptor or regu-latory binding studies), as disclosed in this patent. Therefore, the use of the nonspecific reduction of enzyme activity as the bases of toxicity tests, has not been found in the literature and represents an unexpected finding, that can enable, low cost, shelf stable and rapid field test for toxicity testing purposes.

Enzymes are used to evaluate health status. Common enzymes that are used to positively correlate with toxicity include alkaline phosphatase, lactate dehydrogenase, alanine aminotransferase, aspartate aminotransferase, beta-glu-curonidase, proteases, and antiproteases (Asmis et al., 2008). Important to this invention to point out that abnormal levels of these enzymes are used to determine toxicity based on the production of the enzyme by live cells, tissues or organs and this is typically a positive correlation between more enzyme produced and more toxicity; the enzyme activity is dependent on the live cells; these are not in-chemico cell free or dead cell tests (Ambali et al., 2007). Phosphatases are an enzyme class that catalyzes the removal of phosphate groups. They exist in blood, most in tissues including liver, heart, brain intestines, skin and eye etc. In humans, there are multiple isoforms (tissue nonspecific, intestinal, placental, and germ cell) that play a role in human metabolic processes and higher than normal levels are used in the diagnose of diseases and disorders such as bone disease, diabetes, acute kidney injury, inflammatory bowel disease (IBD), necrotizing enterocolitis, sepsis, and meta-bolic syndrome (Peters et al., 2014; Fawley and Gourlay, 2016; Bover et al., 2018; Danikowski and Cheng, 2019).

Higher than normal phosphatase levels in bronchoalveo-lar lavage has been used to indicate lung toxicity. In one study this activity is attributed to increased Type II cell secretions in response to toxins (Henderson, 2005). In numerous other examples, higher than normal levels of blood phosphatase is used to determine if a drug or chemical has a toxic effect on the body. (Amato et al., 2009; Kartheek and David, 2018). High alkaline phosphatase (ALP) levels may be a sign of a liver problem or a bone disorder (MedlinePlus, 2022).

Herein is provided an in chemico, cell-free method for predicting living tissue toxicity of a test substance is dis-closed.

A method for predicting the living tissue toxicity of a test substance, the method comprising: applying the test sub-stance to a predefined enzyme or enzyme mixture to effect an in chemico reaction, wherein the test substance does not preferentially or specifically bind to an active or regulatory site of the predefined enzyme or enzyme mixture; measuring any reduction in enzymatic activity of the predefined enzyme or enzyme mixture on a predefined substrate; and, comparing the measured reduction in enzymatic activity to a control activity value or previously established activity value, and predicting the extent of, or classification of, living tissue toxicity of the test substance based on the compared measured reduction in enzymatic activity.

Disclosed is an in chemico method for predicting the toxicity to a tissue or cell of a test substance, the method comprising: applying a test substance which does not specifically bind a predefined enzyme and/or which does not specifically bind an active site of a predefined enzyme to the enzyme in a reaction system, measuring any reduction in enzymatic activity on a predefined substrate; and, comparing the measured reduction in enzymatic activity to a control value or previously established activity value, and predicting the toxicity of the test substance based on the compared measured reduction in enzymatic activity after treatment with more toxic test substances.

In embodiments, the enzyme is purified or semi-purified from nonviable cells or nonviable tissue, and cell or tissue remnants remain in the reaction system.

In embodiments, the reaction system does not comprise live cell(s).

In embodiments, the test substance irreversibly reduces enzyme activity and/or non-competitively reduces the enzyme activity.

In embodiments, the test substance reduces enzyme activ-ity by chemically destroying or denaturing the enzyme and the chemistry or binding is not specific to the active or regulatory sites of the enzyme.

In embodiments, the substance being tested is applied at concentrations that are toxic and not therapeutic.

In embodiments, the substance being tested is applied at concentrations of mg/ml and not at ug/ml-femtograms/ml.

In embodiments, the test substances are a diverse group of toxins without, or not known to have, specific pharmaceu-tical activity.

In embodiments, the tissue or cell comprises dermis.

In embodiments, the enzyme is an alkaline phosphatase or acid phosphatase.

In embodiments, the toxicity is corrosiveness, and the method predicts the corrosiveness or not of the test sub-stance.

In embodiments, corrosiveness is indicated if enzyme activity is reduced to 40% or less of control by said test substance.

In embodiments, non-corrosiveness is indicated if enzyme activity is not reduced by at least 40% of the control value by said test substance.

In embodiments, the tissue or cell comprises an ocular tissue or cell.

In embodiments, the enzyme is an esterase.

In embodiments, the toxicity is irritancy, and the method predicts the test substance as an irritant or non-irritant.

In embodiments, the test substance is indicated as an irritant if enzyme activity is reduced by >60%.

In embodiments, the test substance is indicated as a non-irritant if enzyme activity is reduced by ≤60%.

In embodiments, the tissue or cell comprises a nervous system tissue.

In embodiments, the enzyme is one of the following: 12-succinyl-5-enolpyruvyl-6-hydroxy-3-cyclohexene-1-carboxylic-acid synthase, 3-mercaptopyruvate sulfurtrans-ferase, 4-hydroxy-tetrahydrodipicolinate reductase, 4-hy-droxyphenylpyruvate dioxygenase, 6-oxide hydrolase, acetaldehyde dehydrogenase, acetolactate synthase, acetyl-cholinesterase, acid hydrolase, adenosine deaminase, adeno-sylmethionine hydrolase, adenylate cyclase, alanine amino-peptidase, alanine transaminase, alcohol dehydrogenase, alkaline phosphatase, acid phosphatase, nonspecific phos-phatase, alkenylglycerophosphocholine hydrolase, alk-enylglycerophosphoethanolamine hydrolase, aminolevu-linic acid synthase, aminopropanol oxidoreductase, amylase, arginase, aromatase, arsenate reductase, aspartate transaminase, aspartate transcarbamoylase, ATPase, ATP synthase, beta-carotene isomerase, beta-galactosidase, beta-lactamase, biliverdin reductase, biotin synthase, butyrate kinase, caffeine dehydrogenase, carbon disulfide hydrolase, carbonic anhydrase, carbonyl sulfide hydrolase, catalase, catechol-O-methyl transferase, catechol oxidase, chitinase, cholesterol-5, choline acetyltransferase, cholinesterase, coenzyme Q-cytochrome c reductase, cyclamate sulfohydrolase, cypridina-luciferin 2-monooxygenase, cystathionine beta-lyase, cystathionine gamma-lyase, cysteine desulfurase, cytochrome c oxidase, cytochrome c peroxidase, cytochrome P450 oxidase, D-xylulose reductase, deiodinase, deoxyribonuclease, diacetyl dehydrogenase, dichloromethane dehalogenase, dihydrobenzophenanthridine oxidase, dihydrofolate reductase, DNS methyltransferase, elastase, endonuclease, exonuclease, farnesol 2-isomerase, firefly luciferase, flavin prenyltransferase, fructose-bisphosphate aldolase, fructose bisphosphatase, furfylfuramine isomerase, gamma glutamyl transpeptidase, glucose oxidase, glutathione peroxidase, glutathione reductase, glutathione s-transferase, glyceraldehyde 3-phosphate dehydrogenase, glycerol-3-phosphate dehydrogenase, glycerol dehydrogenase, guanylate cyclase, haloacetate dehalogenase, halohydrin dehalogenase, helicase, hepoxilin-epoxide hydrolase, histone methyltransferase, HMG-CoA reductase, homoserine dehydrogenase, hyaluronidase, hypoxanthine-guanine phosphoribosyltransferase, iodothyronine deiodinase, iodotyrosine deiodinase, isochorismatase, isocitrate dehydrogenase, isopenicillin N synthase, L-gluconolactone oxidase, L-xylulose reductase, laccase, lactase, lactate dehydrogenase, leucoanthocyanidin reductase, leukotriene-A4 hydrolase, leukotriene C4 synthase, linolease isomerase, lipoprotein lipase, lipoyl synthase, lysozyme, malate dehydrogenase, maleate isomerase, maleyacetoacetate isomerase, maltase, mandelate racemase, metalloendopeptidase, methylenetetrahydrofolate reductase, microsomal epoxide hydrolase, molybdenum cofactor sulfurtransferase, molybdopterin synthase, molydopterin synthase sulfurtransferase, monoamine oxidase, myeloperoxidase, N-sulfoglucosamine sulfohydrolase, NADH dehydrogenase, nicotinate hydrogenase, nitrate reductase, nitric oxide dioxygenase, nitric oxide synthase, nitrilase, nitrite reductase, nitrogenase, nuclease, oplophorous-luciferin 2-monooxygenase, ornithine decarboxylase, ornithine transcarbamoylase, oxoglutarate dehydrogenase, phenylalanine hydroxylase, phosphatase, phosphoamidase, phospholipase A, phospholipase C, phospholipase D, phosphonoacetaldehyde hydrolase, phosphonoacetate hydrolase, phosphono pyruvate hydrolase, photoisomerase, photoporphyrinogen oxidase, prolyl isomerase, propanediol-phosphate dehydrogenase, peroxidase, protein arginine phosphatase, proteinase K, pyruvate dehydrogenase, *Renilla*-luciferin 2-monooxygenase, retinal isomerase, retinol isomerase, ribonuclease, ribonucleotidetriphosphate reductase, ribonucleotide reductase, RNase, S-adenosyl-L-homocysteine hydrolase, sarcosine oxidase, separase, serine protease, serine racemase, sucrase, sulfite oxidase, superoxide dismutase, tetrahydrocannabinolic acid synthase, thiaminase, thiamine oxidase, thiazole synthase, thioredoxin reductase, thiosulfate-dithiol sulfurtransferase, thiosulfate-thiol sulfurtransferase, thiosulfate sulfurtransferase, thyroid peroxidase, thyroxine 5-deiodinase, trans-epoxysuccinate hydrolase, transaldolase, transglutaminase, transketolase, trithionate hydrolase, tRNA-5-methyluridine(54) 2-sulfurtransferase, tRNA-5-taurinomethyluridine 2-sulfurtransferase, tRNA-uridine-3-sulfurtransferase, tRNA uracil 4-sulfurtransferase, tryptophan synthase, tyrosinase, ubiquitin carboxy-terminal hydrolase, UDP-sulfoquinovose synthase, urate oxidase, urease, uridine monophosphate synthetase, Vitamin K epoxide reductase, watasenia-luciferin 2-monooxygenase, xanthine dehydrogenase, xanthine oxidase.

In embodiments, the substrate used to determine enzyme activity level is one of the following: 1-(3-bromophenyl) ethanol, 1-(3-chlorophenyl)ethanol, 1-(4'-chlorophenyl) ethanol, 1-(4'-fluorophenyl)ethanol, 1-(4-bromophenyl) ethanol, 1-(4-chlorophenyl)ethanol, 1-(4-fluorophenyl) ethanol, 1-(4-methylphenyl)ethanol, 1-(p-tolyl)-ethanol, 1-butanal, 1-butanol, 1-chloro-5-acetylfuro[2, 1-decalone, 1-decanol, 1-dichloroacetone, 1-dodecanol, 1-heptanol, 1-hexanal, 1-hexanol, 1-hydroxy-2-butanone, 1-hydroxymethyl-6-methylpyrene, 1-hydroxymethyl-8-methylpyrene, 1-hydroxymethylpyrene, 1-indanol, 1-indanone, 1-nonanol, 1-octanol, 1-pentanol, 1-phenyl-1-butanol, 1-phenyl-1-propanol, 1-phenyl-2-butanol, 1-phenyl-2-propanol, 1-phenylethanol, 2, 2-butanediol, 2-butanol, 2-heptanol, 2-hexanediol, 2-hexanol, 2-methylbutan-1-ol, 2-methylpent-2-enal, 2-octanol, 2-pentanediol, 2-pentanol, 2-phenylpropanol, 2-propanediol, 3,3',3'-diaminobenzidine (DAB),3-butanediol, 3-c]pyridine, 3-methylcyclohexanol, 3-methylcyclohexanone, 3b]thiopyran-4-one-7,4-butanediol, 4-hydroxynon-2-enal, 4-methylumbelliferyl acetate, 4-methylumbelliferyl sulfate potassium salt, 4-nitrophenyl acetate, 4-Nitrophenyl beta-D-maltoside, 4-nitrophenyl decanoate, 4-nitrophenyl palmitate, 4-nitrophenyl stearate, 4-phenyl-2-butanol, 5,5,5'-tetramethylbenzidine (TMB), 5-bromo-4-chloro-3'-indolyphosphate, 5-pentanediol, 6-dichloro-4-nitrophenyl phosphate, 6-dienal, 6-dihydro-6-methyl-4H-thieno[2,7-dimethylocta-2,7-dioxide, 11-cis-retinal, 11-cis-retinol, 12-hydroxydodecanoate, 12-hydroxylauric acid methyl ester, 12-oxolauric acid methyl ester, 13-cis-retinal, 13-cis-retinol, 16-hydroxyhexadecanoate, alpha, alpha-linolenic acid, alpha-Naphthol, alpha-tetralol, amylose, arachidonic acid, bicarbonate, but-2-en-1-ol, but-2-enal, carbohydrates, carvone, cellulose, cellulose azure, chitin azure, collagen-fluorescein bovine, colloidal chitin, cyclitol phosphate, dec-2-enal, deoxyribonucleic acid methyl green, dihomo-gamma-linolenic acid, disodium salt, docohexaenoic acid (DHA), eicosapentaenoic acid (EPA), fat, gelatin, glutamine, hex-2-en-1-ol, hex-2-enal, indanol, lactose, laminarin, methylene blue, nicotinamide adenine dinucleotide (NADH), nitro-blue tetrazolium, oct-2-enal, p-nitrophenyl phosphate, peptide bond, perillyl alcohol, phospholipids, pyrophosphate, tributyrin, tyrosine, urea, Z-Gly-Pro-Arg p-nitroanilide acetate salt, 4-Nitrophenyl phosphate disodium salt hexahydrate, 3,3'-Diaminobenzidine tetrahydrochloride, o-Phenylenediamine dihydrochloride, o-Phenylenediamine, o-Dianisidine, 3,3',5,5'-Tetramethylbenzidine dihydrochloride, 4-Chloro-1-naphthol, 3-Amino-9-ethylcarbazole, 4-Nitrophenyl phosphate disodium salt, 10-Acetyl-3,7-dihydroxyphenoxazine, Casein, alpha-Naphthyl acetate.

In embodiments, prior to applying the test substance the enzyme is diluted in one or more of the following solvents; butanol, acetonitrile, acetone, diethylene glycol, diethyl ether, 1,2-dimethoxyethane, dimethylformamide, dimethyl sulfoxide, ethanol, ethyl acetate, ethylene glycol, glycerin, heptane, hexane, methanol, pentane, propanol, tetrahydrofuran, toluene, water, xylene or similar.

In embodiments, the enzyme comprises alkaline phosphatase, acid phosphatase, nonspecific phosphatase, lactate dehydrogenase, peroxidase, esterase, alanine aminotransferase and aspartate aminotransferase, beta-glucuronidase, proteases, or an antiprotease.

In embodiments, the enzyme is a phosphatase with units ranging from (500 to 25,000).

In embodiments, the activity is measured by p-Nitrophenyl phosphate disodium salt.

In embodiments, a reduction in enzyme activity is used to predict dermal, ocular, lung, nervous system, liver, kidney, intestinal developmental or acute toxicity.

In embodiments, the method is used to predict skin corrosion.

A method for identifying a toxin, the method comprising: adding the material to be tested to:
    a. a water (W) and salt solution with the enzyme in it (WE), and
    b. a salt solution with no enzyme (WB) to be used as a blank (B), and
    c. an alcohol or organic solvent (S) solution with enzyme in it (SE), and
    d. an alcohol or organic solvent solution with no enzyme in it (SB) to be used as a blank.
incubating for a defined period of time;
measuring enzymatic activity and blank values, for example by measuring or observing changes in color or turbidity by eye or with a spectrophotometer;
subtracting the water salt solution blank measured value from the water salt enzyme measured value (WE−WB), and
subtracting the organic solvent solution blank measured value from the organic solvent enzyme measured value (SE−SB), and;
identifying the lower value, either (WE−WB) or (SE−SB), and comparing this to a set cut off value or results from known standards used to define a cut off value;
predicting that the chemical tested is toxic if the lower value is below a cut off value or the measured value for a control chemical with known toxicity and/or;
relating the measured enzymatic activity to an index of toxicity, which can be categorized according to established toxicity classes, as to identify the material tested as a toxin or as not a toxin.

A method wherein the enzyme comprises one or more compounds selected from phosphatase, peroxidase, lactate dehydrogenase, alanine aminotransferase and aspartate aminotransferase, beta-glucuronidase or protease.

A toxicity assessment method, wherein the enzyme is a phosphatase.

A toxicity assessment method wherein the activity is measured by p-Nitrophenyl phosphate disodium salt.

A method wherein the method is used to test predict dermal, ocular, lung, nervous system, liver, kidney, intestinal toxicity irritation or corrosion.

A method wherein the method is used to test is used to predict dermal corrosion.

A method wherein the established toxicity classes are selected from nonirritant, irritant and corrosive.

A method in which the water-based salt solution and alcohol or organic solvent are combined.

A product or kit used to test for toxicity, which includes;
    a. tubes with an enzyme diluted in a solvent (test and control tubes)
    b. tubes with the solvent alone (blank tube)
    c. a substrate for the solvent
    d. instructions to
        a. add material to be tested to a tube with enzyme and solvent (test tube) and to a second tube with the solvent alone (blank tube) and retain a 3rd tube with enzyme and solvent but do not add the material to be tested (control tube).

b. incubate all 3 tubes for a set time
        c. transfer an aliquot of each tube to an enzyme substrate
        d. visually or quantitatively measure the amount of enzyme substrate converted to product over a set period of time
        e. subtract the blank tube value (solvent alone) from the value of the test tube (solvent plus enzyme).
        f. classify the material tested as toxic if the amount of substrate converted to product (Test tube) minus the solvent alone (blank tube) is below a set value or below a set value or percent of the control tube (enzyme solvent without the material to be tested).

A product or kit used to identify toxic chemicals, which includes;
    a. a cell free enzyme solution, diluted into one or more suitable solvents, such as water, ethanol or an organic solvent.
    b. a nontoxic chemical to serve as negative control.
    c. A substrate for the enzyme, that when the enzyme solution is added allows for the evaluation of the enzyme's activity.

A product or kit used to test for high throughput testing to identify dermal corrosives, which includes;
    a. 4 types of *prefilled tubes with A1 (buffered saline with alkaline phosphatase), B1 (blank buffered saline), A2 (ethanol with alkaline phosphatase), B2 (blank ethanol). *Can also be provided in bulk vials and user can aliquot into tubes.
    b. Negative control (water)
    c. Positive control (acetic acid)
    d. Provided Detection Reagent (DR) solution (p-Nitrophenyl phosphate disodium salt).

In embodiments, the method includes applying the test substance to a cell-free or dead cell test system under conditions in which substance tested is allowed to interact with the enzyme, including where the enzyme is diluted in: (1) a salt water solution, (2) an organic solvent, (3) or both (1) and (2); adding substrate for the enzyme and then; measuring the product of the activity of the enzyme as the substrate is acted on by the enzyme; and predicting the toxicity of the test substance based on the test system response.

In some embodiments, the enzyme is in a water solution. In other embodiments, the enzyme is in an solvent such as an alcohol or organic solvent. In other embodiments, both the enzyme in a water-based solution and the enzyme in a solvent such as alcohol are both tested and a combination or the result with the greater response is used to predict toxicity.

In some embodiments, the water-based solution and other solvent solution are tested without the enzyme, and this value is used to subtract any background introduced by the chemical being tested.

In one embodiment, the toxicity prediction is for skin, eye, lung, heart, brain, kidney, intestine or another target tissue found in the human body.

A method for determining the toxicity of a test chemical that uses a shelf stable enzyme and its substrate, that can be stored and used in a laboratory or a field setting.

In some embodiments of the method, components are assembled as a kit, which can include, for example, 4 small tubes each with; 1) enzyme in water solution, 2) water solution alone, 3) enzyme in alcohol or organic solvent, alcohol or organic solvent alone and 4 large tubes that each contain the enzyme substrate. To use the kit, the user then adds a drop of the material to be tested into the small tube, incubates for a defined period of time, and transfers a drop of each incubated material into each large tubes, incubates a defined period of time, and observed a color change or measures the optical density using a laboratory spectrophotometer or plate reader; or measures the optical density using a field pipette spectrophotometer, subtracts background by subtract ting the OD for the condition without enzyme from the corresponding condition with enzyme, identified the lowest reading, compares this reading to a set value, and if the reading is below the set value, predicts that the material tested is toxic.

In some embodiments, toxins with no know specific enzyme active site or regulatory site binding activity may include one of more of the following: dodecanaminium, N-(2-hydroxy-3-sulfopropyl)-N,N-dimethyl-,1-naphthaleneacetic acid, 1-octanol, 1,2,4-triazole, sodium salt, 1,3-diisopropylbenzene, 1,3-diiminobenz (f)-isoindoline, 1,5-hexadiene, 2-benzyl-4-chlorophenol, 2-benzyloxyethanol, 2-ethoxyethyl acetate (cellosolve acetate), 2-ethyl-1-hexanol, 2-hydroxyisobutyric acid ethylester, 2-hydroxyisobutyric acid, 2-methyl-1-pentanol, 2-methylbutyric acid, 2-naphthalene sulfonic acid, formaldehyde, hydroxymethylbenzene sulfonic acid monosodium salt, 2-nitro-4-thiocyanoaniline, 2,2-dimethyl-3-pentanol, 2,2-dimethyl butanoic acid, 2,5-dimethyl-2,5-hexanediol, 2,6-dichlorobenzoyl chloride, 2,6-dichloro-5-fluoro-beta-oxo-3-pyridinepropanoate, 3-chloropropionitrile, 3,3-dithiodipropionic acid, 3,4-dichlorophenyl isocyanate, 4-(1,1,3,3-tetramethylbutyl) phenol, 4-tert-butylcatechol, 4-carboxybenzaldehyde, 4-chloro-methanilic acid, 6-methyl purine, p-tert-butylphenol, acetic acid, acetone, acid blue 40, acid red 92, alpha-ketoglutaric acid alpha, ammonia, aluminum chloride, gamma-aminopropyltriethoxy silane, ammonium nitrate, antimony oxide, benzalkonium chloride, benzalkonium chloride (10%), benzenesulfonyl chloride, benzethonium chloride (10%), benzene, 1,1'-oxybis-, tetrapropylene derivatives, sulfonated, sodium salts, benzotrichloride, benzyl alcohol, beta-resorcylic acid, bis-(3-aminopropyl) tetramethyl disiloxane, butanol, butyl acetate, butyl cellosolve, butyl dipropasol solvent, butylnaphthalene sulfonic acid sodium salt, butyrolactone, calcium thioglycolate, captan 90-concentrate (solid), camphene, cetylpyridinium bromide (10%), cetylpyridinium chloride (10%), cetyltrimethylammonium bromide (10%), chlorhexidine, chloroform, cyclohexanol, cyclohexanone, cyclohexyl isocyanate, cyclopentanol, deoxycholic acid sodium salt (10%), di(2-ethylhexyl) sodium sulfosuccinate (10%), di(propylene glycol) propyl ether, dibenzoyl-L-tartaric acid, dibenzyl phosphate, diethylaminopropionitrile, domiphen bromide (10%), ethanol, ethyl 2-methyl acetoacetate, ethyl trimethyl acetate, glycidyl methacrylate, granuform, hydroxyethyl acrylate, imidazole, isobutanal, isobutyl alcohol, isopropyl alcohol, lactic acid, lauric acid, lauryldimethylamine oxide, lime, m-phenylene diamine, magnesium hydroxide, maneb, methoxyethyl acrylate, methyl acetate, methyl cyanoacetate, methyl cyclopentane, methyl ethyl ketone (2-butanone), methyl isobutyl ketone, methylpentynol, methylthioglycolate, myristyl alcohol, n-acetyl-methionine, n-butanol, n-hexanol, n-laurylsarcosine sodium salt (10%), n-octylamine, N,N,N',N'-tetramethylhexanediamine, naphthalenesulfonic acid, 2-naphthalenesulfonic acid, sodium salt, nitric acid, organofunctional silane 45-49, phosphorodicloridic acid, hydrogenated tallow amine, polyoxyethylene(23) lauryl ether, potassium laurate (10%), potassium oleate, promethazine hydrochloride, potassium hydroxide, protectol PP, pyridine, benzyl-C12-16-alkyldimethyl, silver nitrate, sodium 2-naphthalenesulfonate, sodium hydrogen difluoride, sodium hydrogen sulfate, sodium hydroxide (10%), sodium lauryl sulfate, sodium lauryl sulfate (15%), sodium monochloroacetate, sodium oxalate, sodium perborate tetrahydrate, sodium polyoxyethylene(3) lauryl ether sulfate, sodium salicylate, stearyltrimethylammonium chloride, sulfuric acid, tetra-N-octylammonium bromide, tetraethylene glycol diacrylate, tetrahydrofuran, trichloroacetic acid (30%), trichloroacetyl chloride, triethanolamine, triethanolamine polyoxyethylene(3.0) lauryl ether sulfate, triton X-100, triton X-100 (5%), triton X-100 (10%).

In some embodiments, known nonirritants and non-toxicants, some with active site or regulatory site binding activity by toxins may include one or more of the following: 1-bromo-4-chlorobutane, styrene, 1,9-decadiene, 2-ethylhexyl p-dimethylamino benzoate, 2-methylpentane, 2-(n-dodecylthio)-ethanol, 2,2-dimethyl-3-pentanol, 2,4-difluoronitrobenzene, 2,4-pentanediol, 3-methoxy-1,2-propanediol, 3-methylhexane, 3,3-dimethylpentane, acrylic acid homopolymer sodium salt, di-n-propyl disulphide, diisobutyl ketone, ethylhexyl salicylate, glycerol, iso-octyl acrylate, isopropyl bromide, isopropyl myristate, iso-octyl-thioglycolate, methyl trimethyl acetate, n-hexyl bromide, n-octyl bromide, n,n-dimethylguanidine sulfate, polyethylene glycol 400, polyethyleneglycol monolaurate (10 E.O.), polyoxyethylene hydrogenated castor oil (60E.O.), polyoxyethylene(14) tribenzylated phenyl ether, polyoxyethylene (160) sorbitan triisostearate, polyoxyethylene (40) hydrogenated castor oil, potassium tetrafluoroborate, propylene glycol, sodium lauryl sulfate (3%), sorbitan monolaurate, tetra-aminopyrimidine sulfate, toluene, triton X-100 (1%), and tween 80.

In some embodiments, enzymes destroyed or inactivated by toxin chemistries that are not specific to active or regulatory sites may include one of more of the following: 2-succinyl-5-enolpyruvyl-6-hydroxy-3-cyclohexene-1-carboxylic-acid synthase, 3-mercaptopyruvate sulfurtransferase, 4-hydroxy-tetrahydrodipicolinate reductase, 4-hydroxy-phenylpyruvate dioxygenase, 6-oxide hydrolase, acetaldehyde dehydrogenase, acetolactate synthase, acetylcholinesterase, acid hydrolase, adenosine deaminase, adenosylmethionine hydrolase, adenylate cyclase, alanine aminopeptidase, alanine transaminase, alcohol dehydrogenase, alkaline phosphatase, alkenylglycerophosphocholine hydrolase, alkenylglycerophosphoethanolamine hydrolase, aminolevulinic acid synthase, aminopropanol oxidoreductase, amylase, arginase, aromatase, arsenate reductase, aspartate transaminase, aspartate transcarbamoylase, ATPase, ATP synthase, beta-carotene isomerase, beta-galactosidase, beta-lactamase, biliverdin reductase, biotin synthase, butyrate kinase, caffeine dehydrogenase, carbon disulfide hydrolase, carbonic anhydrase, carbonyl sulfide hydrolase, catalase, catechol-O-methyl transferase, catechol oxidase, chitinase, cholesterol-5, choline acetyltransferase, cholinesterase, coenzyme Q-cytochrome c reductase, cyclamate sulfohydrolase, cypridina-luciferin 2-monooxygenase, cystathionine beta-lyase, cystathionine gamma-lyase, cysteine desulfurase, cytochrome c oxidase, cytochrome c peroxidase, cytochrome P450 oxidase, D-xylulose reductase, deiodinase, deoxyribonuclease, diacetyl dehydrogenase, dichloromethane dehalogenase, dihydrobenzophenanthridine oxidase, dihydrofolate reductase, esterase, DNS methyltransferase, elastase, endonuclease, exonuclease, farnesol 2-isomerase, firefly luciferase, flavin prenyltransferase, fructose-bisphosphate aldolase, fructose bisphosphatase, furfylfuramine isomerase, gamma glutamyl transpeptidase, glucose oxidase, glutathione peroxidase, glutathione reductase, glutathione s-transferase, glyceraldehyde 3-phosphate dehydrogenase, glycerol-3-phosphate dehydrogenase, glycerol dehydrogenase, guanylate cyclase, haloacetate dehalogenase, halohydrin dehalogenase, helicase, hepoxilin-epoxide hydrolase, histone methyltransferase, HMG-CoA reductase, homoserine dehydrogenase, hyaluronidase, hypoxanthine-guanine phosphoribosyltransferase, iodothyronine deiodinase, iodotyrosine deiodinase, isochorismatase, isocitrate dehydrogenase, isopenicillin N synthase, L-gluconolactone oxidase, L-xylulose reductase, laccase, lactase, lactate dehydrogenase, leucoanthocyanidin reductase, leukotriene-A4 hydrolase, leukotriene C4 synthase, linolease isomerase, lipoprotein lipase, lipoyl synthase, lysozyme, malate dehydrogenase, maleate isomerase, maleyacetoacetate isomerase, maltase, mandelate racemase, metalloendopeptidase, methylenetetrahydrofolate reductase, microsomal epoxide hydrolase, molybdenum cofactor sulfurtransferase, molybdopterin synthase, molydopterin synthase sulfurtransferase, monoamine oxidase, myeloperoxidase, N-sulfoglucosamine sulfohydrolase, NADH dehydrogenase, nicotinate hydrogenase, nitrate reductase, nitric oxide dioxygenase, nitric oxide synthase, nitrilase, nitrite reductase, nitrogenase, nuclease, oplophorous-luciferin 2-monooxygenase, ornithine decarboxylase, ornithine transcarbamoylase, oxoglutarate dehydrogenase, peroxidase, phenylalanine hydroxylase, phosphatase, phosphoamidase, phospholipase A, phospholipase C, phospholipase D, phosphonoacetaldehyde hydrolase, phosphonoacetate hydrolase, phosphono pyruvate hydrolase, photoisomerase, photoporphyrinogen oxidase, prolyl isomerase, propanediol-phosphate dehydrogenase, protein arginine phosphatase, proteinase, pyruvate dehydrogenase, *Renilla*-luciferin 2-monooxygenase, retinal isomerase, retinol isomerase, ribonuclease, ribonucleotide-triphosphate reductase, ribonucleotide reductase, RNase, S-adenosyl-L-homocysteine hydrolase, sarcosine oxidase, separase, serine protease, serine racemase, sucrase, sulfite oxidase, superoxide dismutase, tetrahydrocannabinolic acid synthase, thiaminase, thiamine oxidase, thiazole synthase, thioredoxin reductase, thiosulfate-dithiol sulfurtransferase, thiosulfate-thiol sulfurtransferase, thiosulfate sulfurtransferase, thyroid peroxidase, thyroxine 5-deiodinase, trans-epoxysuccinate hydrolase, transaldolase, transglutaminase, transketolase, trithionate hydrolase, tRNA-5-methyluridine(54) 2-sulfurtransferase, tRNA-5-taurinomethyluridine 2-sulfurtransferase, tRNA-uridine-3-sulfurtransferase, tRNA uracil 4-sulfurtransferase, tryptophan synthase, tyrosinase, ubiquitin carboxy-terminal hydrolase, UDP-sulfoquinovose synthase, urate oxidase, urease, uridine monophosphate synthetase, Vitamin K epoxide reductase, watasenia-luciferin 2-monooxygenase, xanthine dehydrogenase, xanthine oxidase.

In some embodiments, enzyme solvents to dilute the enzyme and conduct the test may include one of more of the following: 1-(3-bromophenyl)ethanol, 1-(3-chlorophenyl) ethanol, 1-(4'-chlorophenyl)ethanol, 1-(4'-fluorophenyl) ethanol, 1-(4-bromophenyl)ethanol, 1-(4-chlorophenyl) ethanol, 1-(4-fluorophenyl)ethanol, 1-(4-methylphenyl) ethanol, 1-(p-tolyl)-ethanol, 1-butanal, 1-butanol, 1-chloro-5-acetylfuro[2, 1-decalone, 1-decanol, 1-dichloroacetone, 1-dodecanol, 1-heptanol, 1-hexanal, 1-hexanol, 1-hydroxy-2-butanone, 1-hydroxymethyl-6-methylpyrene, 1-hydroxymethyl-8-methylpyrene, 1-hydroxymethylpyrene, 1-indanol, 1-indanone, 1-nonanol, 1-octanol, 1-pentanol, 1-phenyl-1-butanol, 1-phenyl-1-propanol, 1-phenyl-2-butanol, 1-phenyl-2-propanol, 1-phenylethanol, 2, 2-butanediol, 2-butanol, 2-heptanol, 2-hexanediol, 2-hexanol, 2-methylbutan-1-ol, 2-methylpent-2-enal, 2-octanol, 2-pentanediol, 2-pentanol, 2-phenylpropanol, 2-propanediol, 3,3',3'-di-aminobenzidine (DAB),3-butanediol, 3-c]pyridine, 3-methylcyclohexanol, 3-methylcyclohexanone, 3b]thiopyran-4-one-7,4-butanediol, 4-hydroxynon-2-enal, 4-methylumbelliferyl acetate, 4-methylumbelliferyl sulfate potassium salt, 4-nitrophenyl acetate, 4-Nitrophenyl beta-D-maltoside, 4-nitrophenyl decanoate, 4-nitrophenyl palmitate, 4-nitrophenyl stearate, 4-phenyl-2-butanol, 5,5,5'-tetramethylbenzidine (TMB), 5-bromo-4-chloro-3'-indolyphosphate, 5-pentanediol, 6-dichloro-4-nitrophenyl phosphate, 6-dienal, 6-dihydro-6-methyl-4H-thieno[2,7-di-methylocta-2,7-dioxide, 11-cis-retinal, 11-cis-retinol, 12-hydroxydodecanoate, 12-hydroxylauric acid methyl ester, 12-oxolauric acid methyl ester, 13-cis-retinal, 13-cis-retinol, 16-hydroxyhexadecanoate, alpha, alpha-linolenic acid, alpha-Naphthol, alpha-tetralol, amylose, arachidonic acid, bicarbonate, but-2-en-1-ol, but-2-enal, carbohydrates, carvone, cellulose, cellulose azure, chitin azure, collagen-fluorescein bovine, colloidal chitin, corn starch, cyclitol phosphate, dec-2-enal, deoxyribonucleic acid methyl green, dihomo-gamma-linolenic acid, disodium salt, docohexaenoic acid (DHA), eicosapentaenoic acid (EPA), fat, gelatin, glutamine, hex-2-en-1-ol, hex-2-enal, hydrogen peroxide, indanol, lactose, laminarin, linoleic acid, lipids, methylene blue, nicotinamide adenine dinucleotide (NADH), nitro-blue tetrazolium, oct-2-enal, p-nitrophenyl phosphate, peptide bond, perillyl alcohol, phospholipids, potato starch, protein, pyrophosphate, starch, sucrose, tributyrin, tyrosine, urea, Z-Gly-Pro-Arg p-nitroanilide acetate salt, 4-Nitrophenyl phosphate disodium salt hexahydrate, 3,3'-Diaminobenzidine tetrahydrochloride, o-Phenylenediamine dihydrochloride, o-Phenylenediamine, o-Dianisidine, 3,3',5,5'-Tetramethylbenzidine dihydrochloride, 4-Chloro-1-naphthol, 3-Amino-9-ethylcarbazole, 4-Nitrophenyl phosphate disodium salt, 10-Acetyl-3,7-dihydroxyphenoxazine, Casein, alpha-Naphthyl acetate.

In some embodiments, solvents used to dilute the enzyme and conduct the reaction to identify potential toxins may include one of more of the following: acetic acid, acetone, acetonitrile, anisole, benzene, 1-butanol, 2-butanol, 2-butanone, tert-butyl alcohol, carbon tetrachloride, chlorobenzene, chloroform, cumene, cyclohexane, 1,2-dichloroethane, 1,1-dichloroethane, 1,2-dichloroethane, dichloromethane, 1,2-dimethoxyethane, diethylene glycol, diethyl ether, diglyme, 1,2-dimethoxyethane, dimethylformamide, dimethyl sulfoxide, 1,4-dioxane, ethanol, 2-ethoxyethanol, ethyl acetate, ethylene glycol, ethyl ether, ethyl formate, formamide, formic acid, glycerin, heptane, hexamethylphosphoramide, hexamethylphosphorus triamide, hexane, isobutyl acetate, isopropyl acetate, methanol, 2-methoxyethanol, methyl acetate, 3-methyl-1-butanol, methylbutylketone, methyl tert-butyl ether, methylene chloride, N-methyl-2-pyrrolidinone, methylethylketone, methylisobutylketone, 2-methyl-1-propanol, nitromethane, pentane, 1-pentanol, petroleum ether, 1-propanol, 2-propanol, propylacetate, pyridine, sulfolane, tetrachloroethylene, tetrahydrofuran, tetralin, toluene, 1,1,1-trichloroethane, 1,1,2-trichloroethene, triethyl amine, water, o-xylene, m-xylene, and p-xylene.

As used herein, unless otherwise indicated by context, "toxicity" is used to refer to a substance's ability to damage, disintegrate, irritate, or otherwise negatively affect a tissue of the body. Toxicity may be evidenced by pain, irritation, swelling, opaqueness, redness, and discharge. Such effects may be temporary or permanent. Accordingly, the word "toxicity" is defined broadly to include any discomfort or unfavorable experience associated with the presence of a substance contacting an eye. As used herein, "toxicity" or "toxin" is used to cover the spectrum of between irritating to highly corrosive.

BRIEF DESCRIPTION OF THE DRAWINGS

FIGS. 3A-3B depict the raw optical density readings from the initial alkaline phosphatase studies. FIG. 3A depicts the results from the procedure conducted with discs. FIG. 3B depicts the results from the procedure conducted without discs. The top three rows on both figures show the p-Nitrophenyl phosphate (PNPP) readings and the bottom three rows show the blank buffered saline. The blank buffered saline was conducted to account for any chemical interference. Test materials include C1=(2-bromoethyl)benzene, C2=Triethylene glycol, C3=2-Methyl-4-phenyl-2-butanol, C4=Cyclamen aldehyde, C5=Heptanal, C6=di-n-Propyl disulfide, C7=Ethanolamine, C8=Dimethyldipropylenetriamine, and C9=Acetic acid.

FIG. 4 depicts the raw optical density readings from a repeat of the procedure (FIG. 3B). The top three rows on both figures show the p-Nitrophenyl phosphate (PNPP) readings and the bottom three rows show the blank buffered saline. The blank buffered saline was conducted to account for any chemical interference. Test materials include C1=1-Bromo-4-chlorobutane, C2=1,5-Hexadiene, C3=Isopropanol, C4=Isopropyl myristate, C5=di-n-Propyl disulfide, C6=Cyclamen aldehyde, C7=Dimethyldipropylenetriamine, C8=Potassium hydroxide (10%), and C9=2-Methylbutyric acid.

FIGS. 5A-5D depict the raw optical density readings from the study that evaluated a shorter exposure time and different p-Nitrophenyl phosphate disodium salt (PNPP) incubation times. FIG. 5A depicts the results from a 10-minute p-Nitrophenyl phosphate disodium salt (PNPP) reading. FIG. 5B depicts the results from a 1-hour p-Nitrophenyl phosphate disodium salt (PNPP) reading. FIG. 5C depicts the results from a 4-hour p-Nitrophenyl phosphate disodium salt (PNPP) reading. FIG. 5D depicts the results from an 18-hour p-Nitrophenyl phosphate disodium salt (PNPP) reading. The top three rows on both figures show the p-Nitrophenyl phosphate (PNPP) readings and the bottom three rows show the blank buffered saline. The blank buffered saline was conducted to account for any chemical interference. Test materials include C1=1-Bromo-4-chlorobutane, C2=1,5-Hexadiene, C3=Isopropanol, C4=Isopropyl myristate, C5=di-n-Propyl disulfide, C6=Cyclamen aldehyde, C7=Dimethyldipropylenetriamine, C8=Potassium hydroxide (10%), and C9=2-Methylbutyric acid.

FIGS. 6A-6F depict the raw optical density readings from the study that evaluated different sources and concentrations of alkaline phosphatase in the reaction reagent using 30 chemicals. FIG. 6A depicts the results from the controls (C1=Water, C2=Water/1% Ink, C3=Acetic acid, C4=Acetic acid/1% Ink) for each condition (Original alkaline phosphatase [1:1], Original alkaline phosphatase [1:10], Original alkaline phosphatase [1:100], New alkaline phosphatase, Blank [buffered saline]). Three readings were conducted for each chemical. FIG. 6B depicts the results for the original alkaline phosphatase (1:1) concentration. FIG. 6C depicts the results for the original alkaline phosphatase (1:10) concentration. FIG. 6D depicts the results for the original alkaline phosphatase (1:100) concentration. FIG. 6E depicts the results for the new alkaline phosphatase (1:1) concentration. FIG. 6F depicts the results for the blank (buffered saline) condition, which was conducted to account for any chemical interference. The test chemicals were C5=1-Bromo-4-chlorobutane, C6=1,5-Hexadiene, C7=Isopropanol, C8=4-(Methylthio)benzaldehyde, C9=Isopropyl myristate, C10=Benzyl salicylate, C11=Phenylethyl alcohol, C12=Hydroxycitronellal, C13=Benzyl acetate, C14=Dipropylene glycol, C15=di-n-Propyl disulfide, C16=1-Bromopentane, C17=Cyclamen aldehyde, C18=cis-3-Methyl-2-(2-pentenyl)-2-cyclopenten-1-one, C19=p-Metha-1,8-dien-7-ol, C20=Heptanal, C21=trans-3,7-Diemethyl-2,6-octadien-1-ol, C22=alpha-Terpineol, C23=1-Decanol, C24=Nonyl aldehyde, C25=Dimethyldipropylenetriamine, C26=Potassium hydroxide (10%), C27=2-Methylbutyric acid, C28=Octanonic acid, C29=Dimethylisopropylamine, C30=2-tert-Butylphenol, C31=5-Isopropyl-2-methylphenol, C32=n-Heptylamine, C33=Methoxy-3-propylamine, and C34=N,N-Dimethylbenzylamine.

FIGS. 7A-7B depict the raw optical density readings from the study that evaluated different dosing concentrations and solvents. FIG. 7A depicts the results from a 3-hour test chemical exposure with a 30-minute p-Nitrophenyl phosphate disodium salt (PNPP) incubation. FIG. 7B depicts the results from a 3-hour test chemical exposure with a 1-hour p-Nitrophenyl phosphate disodium salt (PNPP) incubation. The top three rows are results from the 10 μL (into 90 μL) dosing concentration and the bottom three rows are from the 50 μL (into 50 μL) dosing concentration. Condition A is the buffered saline reaction reagent, Condition B is the ethanol reaction reagent, and Condition C is the acetone reaction reagent. The test chemicals were water, methanol, mineral oil, 1-Bromo-4-chlorobutane, 1,5-Hexadiene, di-n-Propyl disulfide, Nonyl aldehyde, Octanoic acid, Dimethylisopropylamine, 5-Isopropyl-2-methylphenol, n-Heptylamine, and N,N-Dimethylbenzylamine.

FIGS. 8A-8C depict the raw optical density readings from the study that evaluated different dosing concentrations and solvents. FIG. 8A depicts the results from a 22-hour test chemical exposure with a 10-minute p-Nitrophenyl phosphate disodium salt (PNPP) incubation.

FIG. 8B depicts the results from a 22-hour test chemical exposure with a 30-minute p-Nitrophenyl phosphate disodium salt (PNPP) incubation. FIG. 8C depicts the results from a 22-hour test chemical exposure with a 1-hour p-Nitrophenyl phosphate disodium salt (PNPP) incubation. The top three rows are results from the 10 μL (into 90 μL) dosing concentration and the bottom three rows are from the 50 μL (into 50 μL) dosing concentration. Condition A is the buffered saline reaction reagent, Condition B is the ethanol reaction reagent, and Condition C is the acetone reaction reagent. The test chemicals were water, methanol, mineral oil, 1-Bromo-4-chlorobutane, 1,5-Hexadiene, di-n-Propyl disulfide, Nonyl aldehyde, Octanoic acid, Dimethylisopropylamine, 5-Isopropyl-2-methylphenol, n-Heptylamine, and N,N-Dimethylbenzylamine.

FIGS. 9A-9B depict the raw optical density readings from the study that evaluated the different alkaline phosphatase reaction reagents dilutions (1:100 and 1:1000) at room temperature and 37° C. FIG. 9A depicts the 4-hour test chemical exposure with a 30-minute p-Nitrophenyl phosphate disodium salt (PNPP) incubation. FIG. 9B depicts the 4-hour test chemical exposure with a 1-hour p-Nitrophenyl phosphate disodium salt (PNPP) incubation. The test chemicals were water, 4-(Methylthio)benzaldehyde, 1-Bromo-4-chlorobutane, 1,5-Hexadiene, alpha-Terpineol, di-n-Propyl disulfide, Nonyl aldehyde, Octanoic acid, Dimethylisopropylamine, 5-Isopropyl-2-methylphenol, n-Heptylamine, and N,N-Dimethylbenzylamine.

FIGS. 10A-10B depict the raw optical density readings from the study that evaluated the different alkaline phosphatase reaction reagents dilutions (1:100 and 1:1000) at room temperature and 37° C. FIG. 10A depicts the 22-hour test chemical exposure with a 30-minute p-Nitrophenyl phosphate disodium salt (PNPP) incubation. FIG. 10B depicts the 22-hour test chemical exposure with a 1-hour p-Nitrophenyl phosphate disodium salt (PNPP) incubation. The test chemicals were water, 4-(Methylthio)benzaldehyde, 1-Bromo-4-chlorobutane, 1,5-Hexadiene, alpha-Terpineol, di-n-Propyl disulfide, Nonyl aldehyde, Octanoic acid, Dimethylisopropylamine, 5-Isopropyl-2-methylphenol, n-Heptylamine, and N,N-Dimethylbenzylamine.

FIGS. 11A-11E depict the raw optical density readings from the study that evaluated the performance of 4 mL glass vials with screw caps using thirty chemicals. FIG. 11A depicts the results of the controls for each condition. FIG. 11B depicts the results from R1+ reaction reagent (active buffered saline). FIG. 11C depicts the results from R1− reaction reagent (blank buffered saline; no alkaline phosphatase added). FIG. 11C depicts the results from R2+ reaction reagent (active ethanol). FIG. 11D depicts the results from R2− reaction reagent (blank ethanol; no alkaline phosphatase added). The test chemicals were C5=1-Bromo-4-chlorobutane, C6=1,5-Hexadiene, C7=Isopropanol, C8=4-(Methylthio)benzaldehyde, C9=Isopropyl myristate, C10=Benzyl salicylate, C11=Phenylethyl alcohol, C12=Hydroxycitronellal, C13=Benzyl acetate, C14=Dipropylene glycol, C15=di-n-Propyl disulfide, C16=1-Bromopentane, C17=Cyclamen aldehyde, C18=cis-3-Methyl-2-(2-pentenyl)-2-cyclopenten-1-one, C19=p-Metha-1,8-dien-7-ol, C20=Heptanal, C21=trans-3,7-Diemethyl-2,6-octadien-1-ol, C22=alpha-Terpineol, C23=1-Decanol, C24=Nonyl aldehyde, C25=Dimethyldipropylenetriamine, C26=Potassium hydroxide (10%), C27=2-Methylbutyric acid, C28=Octanonic acid, C29=Dimethylisopropylamine, C30=2-tert-Butylphenol, C31=5-Isopropyl-2-methylphenol, C32=n-Heptylamine, C33=Methoxy-3-propylamine, and C34=N,N-Dimethylbenzylamine.

FIGS. 12A-12D depicts the raw optical density readings from the study that evaluated the performance between 0.5 mL microcentrifuge tubes and 4 mL glass vials with screw caps. FIG. 12A depicts the results from the 0.5 mL microcentrifuge tubes (top half) and the results from aliquoting 20 μL from the 4 mL glass vial into 200 μL of p-Nitrophenyl phosphate disodium salt (PNPP) substrate solution with a 30-minute p-Nitrophenyl phosphate disodium salt (PNPP) incubation. FIG. 12B depicts the results from the 0.5 mL microcentrifuge tubes (top half) and the results from aliquoting 20 μL from the 4 mL glass vial into 200 μL of p-Nitrophenyl phosphate disodium salt (PNPP) substrate solution with a 1-hour p-Nitrophenyl phosphate disodium salt (PNPP) incubation. FIG. 12C depicts the results from adding 2.6 mL of p-Nitrophenyl phosphate disodium salt (PNPP) substrate solution directly into the 4 mL glass vials with a 30-minute p-Nitrophenyl phosphate disodium salt (PNPP) incubation. FIG. 12D depicts the results from adding 2.6 mL of p-Nitrophenyl phosphate disodium salt (PNPP) substrate solution directly into the 4 mL glass vials with a 1-hour p-Nitrophenyl phosphate disodium salt (PNPP) incubation. The chemicals tested were C1=Water, C3=Acetic acid, C20=Heptanal, C29=Dimethylisopropylamine, C32=n-Heptylamine, and C34=N,N-Dimethylbenzylamine.

FIGS. 13A-13E depict the raw optical readings from the study that combined all finalized parameters from previous studies. FIG. 13A depicts the results from the controls for each condition. FIG. 13B depicts the results from the active buffered saline reaction reagent. FIG. 13C depicts the results from the blank buffered saline reaction reagent. FIG. 13D depicts the results from the active ethanol reaction reagent. FIG. 13E depicts the results from the blank ethanol reaction reagent. The test chemicals were C5=1-Bromo-4-chlorobutane, C6=1,5-Hexadiene, C7=Isopropanol, C8=4-(Methylthio)benzaldehyde, C9=Isopropyl myristate, C10=Benzyl salicylate, C11=Phenylethyl alcohol, C12=Hydroxycitronellal, C13=Benzyl acetate, C14=Dipropylene glycol, C15=di-n-Propyl disulfide, C16=1-Bromopentane, C17=Cyclamen aldehyde, C18=cis-3-Methyl-2-(2-pentenyl)-2-cyclopenten-1-one, C19=p-Metha-1,8-dien-7-ol, C20=Heptanal, C21=trans-3,7-Diemethyl-2,6-octadien-1-ol, C22=alpha-Terpineol, C23=1-Decanol, C24=Nonyl aldehyde, C25=Dimethyldipropylenetriamine, C26=Potassium hydroxide (10%), C27=2-Methylbutyric acid, C28=Octanonic acid, C29=Dimethylisopropylamine, C30=2-tert-Butylphenol, C31=5-Isopropyl-2-methylphenol, C32=n-Heptylamine, C33=Methoxy-3-propylamine, and C34=N,N-Dimethylbenzylamine.

FIG. 14 depicts the results from the study that combined all finalized parameters. The blanks are subtracted from the raw readings and analyzed with a prediction model to estimate the dermal corrosives versus non-corrosives.

FIG. 16 depicts a list of 60 chemicals tested in triplicate using the test kit. The different classifications include not classified as an irritant or corrosive (NC), not classified as a corrosive (Category 2), classified as a corrosive (Category 1BC), and classified as an extreme corrosive (Category 1A).

FIG. 17 depicts a direction sheet for the kit. Steps of using the test kit. For each material to be tested:

1. Uniquely label four 0.5-mL reaction tubes to distinguish the four test matrix reagents (i.e., A1, B1, A2, B2). Add 180 μL of the appropriate test matrix reagent to each of the correspondingly labeled reaction tubes.
2. Add 20 ml of test substance to each of the 4 reaction tubes (A1, B1, A2, B2). Mix the contents of each reaction tube via pipette by aspirating and dispensing 5 times. Close caps.
3. Incubate capped tubes at room temperature for 4 hours±10 min.
4. While the reaction tubes are incubating, prepare a 96-well ELISA plate by aliquoting 200 μL Detection Reagent solution into each well.
5. After the 4-hour incubation, re-mix the contents of each reaction tube via pipette by aspirating and dispensing 5 times. Add 20-μL aliquots of each reaction (in triplicate wells) to the ELISA plate.
6. Incubate the ELISA plate at room temperature for 1 hour±10 min.
7. Measure the optical density (OD) of 405 nm using a plate reader.
8. Calculate the percent remaining activity for the chemical being tested. If remaining activity is less than 40%, classify the material as a dermal corrosive.

Figure 18:
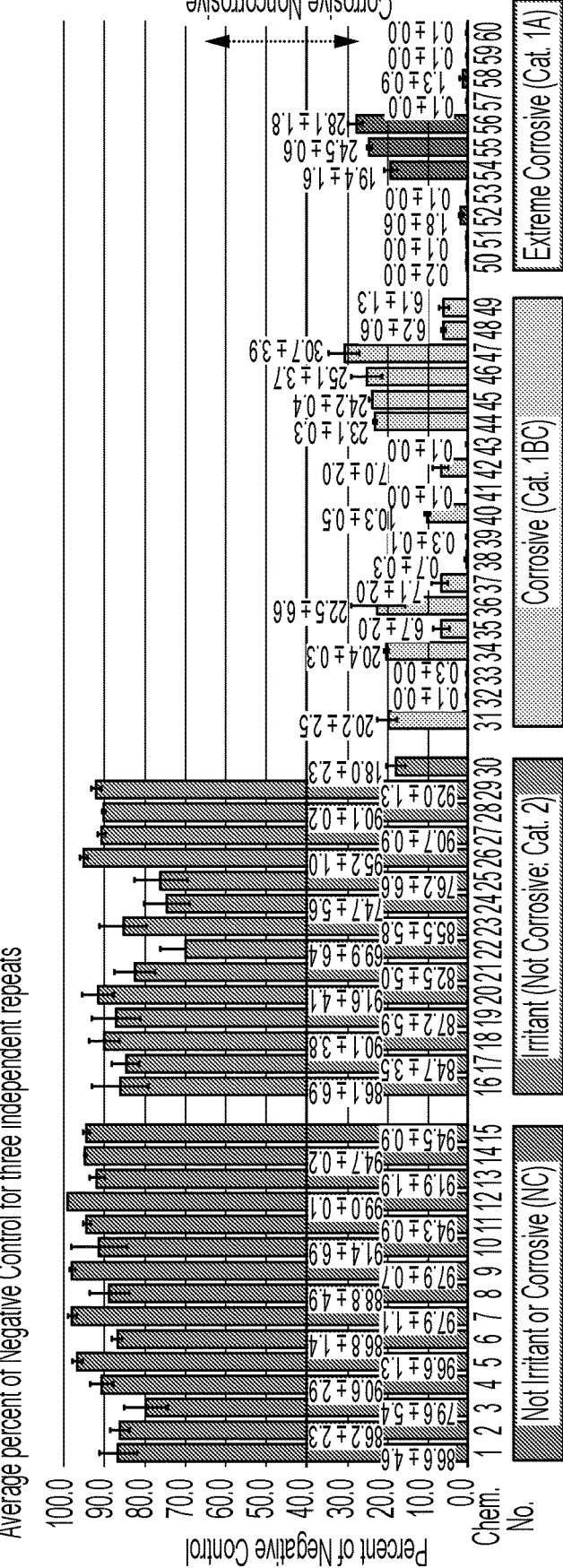

FIG. 18 depicts the results for 60 chemicals tested in triplicate using the test kit. Average percent of Negative Control for three independent repeats. Error bars represent standard error. Chemical numbers are the same as those listed in FIG. 16 which includes the names with the CAS RN in brackets.

FIG. 19 depicts the predictivity data for 60 chemicals tested in triplicate using the test kit.

DETAILED DESCRIPTION

As disclosed herein, the inventors have discovered that a cell free in chemico enzyme solution can be used to predict the toxicity of a test material.

A method for predicting the living tissue toxicity of a test substance, the method comprising:

applying the test substance to a predefined enzyme or enzyme mixture to effect an in chemico reaction, wherein the test substance does not preferentially or specifically bind to an active or regulatory site of the predefined enzyme or enzyme mixture;

measuring any reduction in enzymatic activity of the predefined enzyme or enzyme mixture on a predefined substrate; and, comparing the measured reduction in enzymatic activity to a control activity value or previously established activity value, and predicting the extent of, or classification of, living tissue toxicity of the test substance based on the compared measured reduction in enzymatic activity.

In embodiments, the enzyme is purified or semipurified or is in a mixture composed of nonviable cells and/or nonviable tissue.

In embodiments, the test substance irreversibly reduces the enzyme activity and/or noncompetitively reduces the enzyme activity.

In embodiments, the test substance reduces enzyme activity by chemically destroying or denaturing the enzyme, and/or the chemistry or binding is not specific to the active or regulatory sites of the enzyme.

In embodiments, the test substance is applied at concentrations that are toxic and not therapeutic.

In embodiments, the mass of test substance is applied to the enzyme at a ratio of 1:1-1:100 parts test substance to enzyme solution volume.

In embodiments, the mass of test substance is applied to the enzyme at a ratio of 1:10-1:1,000 parts test substance to enzyme solution volume.

In embodiments, the test substance is applied at concentrations of mg/mL and not at μg/mL-fg/mL.

In embodiments, the test substances are a diverse group of toxins without having specific binding affinity or binding to the enzyme regulatory or active sites.

In embodiments, the test predicts toxicity to living skin, and the accuracy of prediction is 85% or greater.

In embodiments, the enzyme is a phosphatase.

In embodiments, the toxicity is corrosiveness. In embodiments, the method predicts the corrosiveness or not of the test substance with an accuracy of at least 85%.

In embodiments, corrosiveness is predicted if enzyme activity is reduced to 40% or less of control or previously established value by said test substance.

In embodiments, noncorrosiveness is predicted if remaining enzyme activity is greater than 40% of the control or previously established value by said test substance.

In embodiments, the accuracy to predict if the test substance is a dermal corrosive is 90% or greater.

In embodiments, a predefined enzyme or enzyme mixture is sequentially exposed to each of a large number of known toxins (at least 10 toxins) and sequentially exposed to each of a large number of known nontoxins (at least 10 nontoxins), and results for the enzyme activity after toxin exposure are averaged to form an activity class, and results from enzyme activity after exposure to nontoxin exposure is averaged to form an activity class, and the activity class measurement for the toxin class is significantly reduced enzyme activity compared with activity for the nontoxin activity class, and there is a statistically significant separation of the toxin class activity values from the nontoxin class activity values (P value <0.01), and these results are then used to construct a prediction model that identifies toxins based on a specific reduction of enzyme activity with intended use of a prediction model for the identification and classification of the toxicity of unknown materials and when used to test unknowns for toxicity, and an accuracy of prediction of at least 85%.

In embodiments, where a mixture of enzymes are used, activity is determined as an average activity. For example there might be multiple enzymes in a cell extract that all act on the same substrate—and these enzymes may not be defined, but average activity can be measured.

In embodiments, lack of active site binding specificity is verified using a chemical analytical technique. In embodiments, the technique is including mass spectroscopy, HPLC, or gas chromatography.

In embodiments, the tissue to be evaluated comprises an ocular tissue. In embodiments, the accuracy of prediction is at least 85%.

In embodiments, the enzyme is an esterase.

In embodiments, the toxicity is irritancy. In embodiments, the method predicts the test substance as an irritant or nonirritant with an accuracy of at least 85%.

In embodiments, the toxicity is corrosion or irritation, and the method predicts the test substance as corrosive, noncorrosive, irritant or nonirritant.

In embodiments, the enzyme is one of the following: 12-succinyl-5-enolpyruvyl-6-hydroxy-3-cyclohexene-1-carboxylic-acid synthase, 3-mercaptopyruvate sulfurtransferase, 4-hydroxy-tetrahydrodipicolinate reductase, 4-hydroxyphenylpyruvate dioxygenase, 6-oxide hydrolase, acetaldehyde dehydrogenase, acetolactate synthase, acetylcholinesterase, acid hydrolase, adenosine deaminase, adenosylmethionine hydrolase, adenylate cyclase, alanine aminopeptidase, alanine transaminase, alcohol dehydrogenase, alkaline phosphatase, acid phosphatase, nonspecific phosphatase, alkenylglycerophosphocholine hydrolase, alkenylglycerophosphoethanolamine hydrolase, aminolevulinic acid synthase, aminopropanol oxidoreductase, amylase, arginase, aromatase, arsenate reductase, aspartate transaminase, aspartate transcarbamoylase, ATPase, ATP synthase, beta-carotene isomerase, beta-galactosidase, beta-lactamase, biliverdin reductase, biotin synthase, butyrate kinase, caffeine dehydrogenase, carbon disulfide hydrolase, carbonic anhydrase, carbonyl sulfide hydrolase, catalase, catechol-O-methyl transferase, catechol oxidase, chitinase, cholesterol-5, choline acetyltransferase, cholinesterase, coenzyme Q-cytochrome c reductase, cyclamate sulfohydrolase, cypridina-luciferin 2-monooxygenase, cystathionine beta-lyase, cystathionine gamma-lyase, cysteine desulfurase, cytochrome c oxidase, cytochrome c peroxidase, cytochrome P450 oxidase, D-xylulose reductase, deiodinase, deoxyribonuclease, diacetyl dehydrogenase, dichloromethane dehalogenase, dihydrobenzophenanthridine oxidase, dihydrofolate reductase, DNS methyltransferase, elastase, endonuclease, exonuclease, farnesol 2-isomerase, firefly luciferase, flavin prenyltransferase, fructose-bisphosphate aldolase, fructose bisphosphatase, furfylfuramine isomerase, gamma glutamyl transpeptidase, glucose oxidase, glutathione peroxidase, glutathione reductase, glutathione s-transferase, glyceraldehyde 3-phosphate dehydrogenase, glycerol-3-phosphate dehydrogenase, glycerol dehydrogenase, guanylate cyclase, haloacetate dehalogenase, halohydrin dehalogenase, helicase, hepoxilin-epoxide hydrolase, histone methyltransferase, HMG-CoA reductase, homoserine dehydrogenase, hyaluronidase, hypoxanthine-guanine phosphoribosyltransferase, iodothyronine deiodinase, iodotyrosine deiodinase, isochorismatase, isocitrate dehydrogenase, isopenicillin N synthase, L-gluconolactone oxidase, L-xylulose reductase, laccase, lactase, lactate dehydrogenase, leucoanthocyanidin reductase, leukotriene-A4 hydrolase, leukotriene C4 synthase, linolease isomerase, lipoprotein lipase, lipoyl synthase, lysozyme, malate dehydrogenase, maleate isomerase, maleyacetoacetate isomerase, maltase, mandelate racemase, metalloendopeptidase, methylenetetrahydrofolate reductase, microsomal epoxide hydrolase, molybdenum cofactor sulfurtransferase, molybdopterin synthase, molydopterin synthase sulfurtransferase, monoamine oxidase, myeloperoxidase, N-sulfoglucosamine sulfohydrolase, NADH dehydrogenase, nicotinate hydrogenase, nitrate reductase, nitric oxide dioxygenase, nitric oxide synthase, nitrilase, nitrite reductase, nitrogenase, nuclease, oplophorus-luciferin 2-monooxygenase, ornithine decarboxylase, ornithine transcarbamoylase, oxoglutarate dehydrogenase, phenylalanine hydroxylase, phosphatase, phosphoamidase, phospholipase A, phospholipase C, phospholipase D, phosphonoacetaldehyde hydrolase, phosphonoacetate hydrolase, phosphonopyruvate hydrolase, photoisomerase, photoporphyrinogen oxidase, prolyl isomerase, propanediol-phosphate dehydrogenase, peroxidase, protein arginine phosphatase, proteinase K, pyruvate dehydrogenase, Renilla-luciferin 2-monooxygenase, retinal isomerase, retinol isomerase, ribonuclease, ribonucleotide-triphosphate reductase, ribonucleotide reductase, RNase, S-adenosyl-L-homocysteine hydrolase, sarcosine oxidase, separase, serine protease, serine racemase, sucrase, sulfite oxidase, superoxide dismutase, tetrahydrocannabinolic acid synthase, thiaminase, thiamine oxidase, thiazole synthase, thioredoxin reductase, thiosulfate-dithiol sulfurtransferase, thiosulfate-thiol sulfurtransferase, thiosulfate sulfurtransferase, thyroid peroxidase, thyroxine 5-deiodinase, trans-epoxysuccinate hydrolase, transaldolase, transglutaminase, transketolase, trithionate hydrolase, tRNA-5-methyluridine(54) 2-sulfurtransferase, tRNA-5-taurinomethyluridine 2-sulfurtransferase, tRNA-uridine-3-sulfurtransferase, tRNA uracil 4-sulfurtransferase, tryptophan synthase, tyrosinase, ubiquitin carboxy-terminal hydrolase, UDP-sulfoquinovose synthase, urate oxidase, urease, uridine monophosphate synthetase, vitamin K epoxide reductase, Watasenia-luciferin 2-monooxygenase, xanthine dehydrogenase, or xanthine oxidase.

In embodiments, the substrate used to determine enzyme activity level is one of the following: 1-(3-bromophenyl) ethanol, 1-(3-chlorophenyl)ethanol, 1-(4'-chlorophenyl) ethanol, 1-(4'-fluorophenyl)ethanol, 1-(4-bromophenyl) ethanol, 1-(4-chlorophenyl)ethanol, 1-(4-fluorophenyl) ethanol, 1-(4-methylphenyl)ethanol, 1-(p-tolyl)-ethanol, 1-butanal, 1-butanol, 1-chloro-5-acetylfuro[2, 1-decalone, 1-decanol, 1-dichloroacetone, 1-dodecanol, 1-heptanol, 1-hexanal, 1-hexanol, 1-hydroxy-2-butanone, 1-hydroxymethyl-6-methylpyrene, 1-hydroxymethyl-8-methylpyrene, 1-hydroxymethylpyrene, 1-indanol, 1-indanone, 1-nonanol, 1-octanol, 1-pentanol, 1-phenyl-1-butanol, 1-phenyl-1-propanol, 1-phenyl-2-butanol, 1-phenyl-2-propanol, 1-phenylethanol, 2, 2-butanediol, 2-butanol, 2-heptanol, 2-hexanediol, 2-hexanol, 2-methylbutan-1-ol, 2-methylpent-2-enal, 2-octanol, 2-pentanediol, 2-pentanol, 2-phenylpropanol, 2-propanediol, 3,3',3'-diaminobenzidine (DAB),3-butanediol, 3-c]pyridine, 3-methylcyclohexanol, 3-methylcyclohexanone, 3b]thiopyran-4-one-7,4-butanediol, 4-hydroxynon-2-enal, 4-methylumbelliferyl acetate, 4-methylumbelliferyl sulfate potassium salt, 4-nitrophenyl acetate, 4-nitrophenyl beta-D-maltoside, 4-nitrophenyl decanoate, 4-nitrophenyl palmitate, 4-nitrophenyl stearate, 4-phenyl-2-butanol, 5,5,5'-tetramethylbenzidine (TMB), 5-bromo-4-chloro-3'-indolyphosphate, 5-pentanediol, 6-dichloro-4-nitrophenyl phosphate, 6-dienal, 6-dihydro-6-methyl-4H-thieno[2,7-dimethylocta-2,7-dioxide, 11-cis-retinal, 11-cis-retinol, 12-hydroxydodecanoate, 12-hydroxylauric acid methyl ester, 12-oxolauric acid methyl ester, 13-cis-retinal, 13-cis-retinol, 16-hydroxyhexadecanoate, alpha, alpha-linolenic acid, alpha-Naphthol, alpha-tetralol, amylose, arachidonic acid, bicarbonate, but-2-en-1-ol, but-2-enal, carbohydrates, carvone, cellulose, cellulose azure, chitin azure, collagen-fluorescein bovine, colloidal chitin, cyclitol phosphate, dec-2-enal, deoxyribonucleic acid methyl green, dihomo-gamma-linolenic acid, disodium salt, docohexaenoic acid (DHA), eicosapentaenoic acid (EPA), fat, gelatin, glutamine, hex-2-en-1-ol, hex-2-enal, indanol, lactose, laminarin, methylene blue, nicotinamide adenine dinucleotide (NADH), nitro-blue tetrazolium, oct-2-enal, p-nitrophenyl phosphate, peptide bond, perillyl alcohol, phospholipids, pyrophosphate, tributyrin, tyrosine, urea, Z-Gly-Pro-Arg p-nitroanilide acetate salt, 4-nitrophenyl phosphate disodium salt hexahydrate, 3,3'-diaminobenzidine tetrahydrochloride, o-phenylenediamine dihydrochloride, o-phenylenediamine, o-dianisidine, 3,3',5,5'-tetramethylbenzidine dihydrochloride, 4-chloro-1-naphthol, 3-amino-9-ethylcarbazole, 4-nitrophenyl phosphate disodium salt, 10-acetyl-3, 7-dihydroxyphenoxazine, casein, or alpha-naphthyl acetate.

In embodiments, prior to applying the test substance the enzyme is diluted in one or more of the following solvents: butanol, acetonitrile, acetone, diethylene glycol, diethyl ether, 1,2-dimethoxyethane, dimethylformamide, dimethyl sulfoxide, ethanol, ethyl acetate, ethylene glycol, glycerin, heptane, hexane, methanol, pentane, propanol, tetrahydrofuran, toluene, water, xylene, or similar.

In embodiments, prior to applying the test substance, the enzyme is diluted in both 1) ethanol or similar and 2) water or similar, and the test substance is applied to both 1 and 2, and the greater reduction in enzyme activity from either 1 or 2 is used to predict toxicity of the test substance or material.

In embodiments, the enzyme comprises alkaline phosphatase, acid phosphatase, nonspecific phosphatase, lactate dehydrogenase, peroxidase, esterase, alanine aminotransferase and aspartate aminotransferase, beta-glucuronidase, protease, or an antiprotease.

In embodiments, the enzyme is a phosphatase and from 500 to 25,000 units are applied to each 1) salt water and 2) ethanol.

In embodiments, the activity is measured by p-nitrophenyl phosphate disodium salt.

In embodiments, a reduction in enzyme activity is used to predict dermal, ocular, lung, nervous system, liver, kidney, intestinal developmental, or acute toxicity.

In embodiments, the method is used to test is used to predict skin corrosion.

The developed test disclosed herein has predictive value. In embodiments, the control values are, or are derived from, a validation dataset. Validation data can be derived, e.g., from the test performed using standard, known toxics (e.g., irritants, corrosives) and/or by confirming substances identified as toxic to living tissue (e.g., irritants, corrosives) by other secondary known tests conforming the same identity.

A method for identifying a toxin, the method comprising: adding the material to be tested to:
  a. a water (W) and salt solution with the enzyme in it (WE), and
  b. a salt solution with no enzyme (WB) to be used as a blank (B), and
  c. an alcohol or organic solvent (S) solution with enzyme in it (SE), and
  d. an alcohol or organic solvent solution with no enzyme in it (SB) to be used as a blank;
incubating for a defined period of time;
measuring enzymatic activity and blank values, for example, by measuring or observing changes in color or turbidity by eye or with a spectrophotometer;
subtracting the water salt solution blank measured value from the water salt enzyme measured value (WE−WB);
subtracting the organic solvent solution blank measured value from the organic solvent enzyme measured value (SE−SB);
identifying the lower value, either (WE−WB) or (SE−SB), and comparing this to a set cut off value or results from known standards used to define a cut-off value;
predicting that the chemical tested is toxic if the lower value is below a cut-off value or the measured value for a control chemical with known toxicity, and/or;
relating the measured enzymatic activity to an index of toxicity, which can be categorized according to established toxicity classes, as to identify the material tested as a toxin or nontoxin.

In embodiments, the enzyme comprises one or more compounds selected from phosphatase, peroxidase, lactate dehydrogenase, alanine aminotransferase and aspartate aminotransferase, beta-glucuronidase, or protease.

In embodiments, the enzyme is a phosphatase.

In embodiments, the activity is measured by p-nitrophenyl phosphate disodium salt.

In embodiments, the method is used to test predict dermal, ocular, lung, nervous system, liver, kidney, intestinal toxicity irritation, or corrosion.

In embodiments, the method is used to test is used to predict dermal corrosion.

In embodiments, the established toxicity classes are selected from nonirritant, irritant, and corrosive.

In embodiments, the water-based salt solution and alcohol or organic solvent are combined.

A product or kit used to test for toxicity, which includes;
  a. tubes with an enzyme diluted in a solvent (test and control tubes)
  b. tubes with the solvent alone (blank tube)
  c. a substrate for the solvent
  d. instructions to:
    a. add material to be tested to a tube with enzyme and solvent (test tube) and to a second tube with the solvent alone (blank tube) and retain a third tube with enzyme and solvent but do not add the material to be tested (control tube);
    b. incubate all three tubes for a set time;
    c. transfer an aliquot of each tube to an enzyme substrate;
    d. visually or quantitatively measure the amount of enzyme substrate converted to product over a set period of time;
    e. subtract the blank tube value (solvent alone) from the value of the test tube (solvent plus enzyme); and
    f. classify the material tested as toxic if the amount of substrate converted to a product (test tube) minus the solvent alone (blank tube) is below a set value or below a set value or percent of the control tube (enzyme solvent without the material to be tested).
    A product or kit used to identify toxic chemicals, which includes:
  a. a cell free enzyme solution, diluted into one or more suitable solvents, such as water, ethanol or an organic solvent.
  b. a nontoxic chemical to serve as negative control.
  c. a substrate for the enzyme, that when the enzyme solution is added allows for evaluation of the enzyme's activity.
A product or kit used to test for high throughput testing to identify dermal corrosives, which includes:
  a. four types of *prefilled tubes with A1 (buffered saline with alkaline phosphatase), B1 (blank buffered saline), A2 (ethanol with alkaline phosphatase), B2 (blank ethanol). *Can also be provided in bulk vials and user can aliquot into tubes.
  b. negative control (water)
  c. positive control (acetic acid)
  d. detection reagent (DR) solution (p-nitrophenyl phosphate disodium salt).
Previously we have developed the in chemico test for ocular irritants and corrosives (called the OptiSafe Eye Irritation Test™) (Choksi et al., 2020; Lebrun, 2021a, 2021b; Lebrun et al., 2021a, 2021b, 2022, 2023a, 2023b). The OptiSafe "macromolecular test" measures the turbidity resulting from the denaturation of proteins by chemical irritants. No enzymatic activity is involved. Initially we evaluated our OptiSafe test for the ability to identify other types of toxins including dermal corrosives, but found little or no correlation with OptiSafe results for dermal corrosives; clearly the skin and eye have very different histological, protective and macromolecular compositions. The eye has a thin (5-7 cells) layer of epithelium covering a transparent cornea, composed chiefly of collagen. The skin has a comparatively thick epidermis, with epithelial cells in various stages of terminal differentiation with the apical layer fully keratinized, resulting in a water-resistant protective barrier, and below the epidermis, the dermis layer with connective tissue. Initially we assumed that the significant structural differences between the eye and the skin likely explain why the OptiSafe test did not accurately predict skin toxicity. Therefore, to try and identify additional molecular targets or markers that could be used to develop other shelf stable toxicity tests, over the last four years we have performed a series of studies where we have dosed rabbit or porcine tissues and then after incubation performed wide range of immunohistochemistry experiments on post exposure cryosections. We have used conjugated antibodies or other probes for a large number of inflammatory markers, cytokines and markers for connective tissue disruption (collagen, actin, etc.). The main reason we worked so many years on ex vivo and 3D tissue models was we were convinced that an accurate toxicity test required and especially a skin toxicity test requires a full thickness skin. Our histopathology studies using ex vivo "buttons" (5 mm biopsy) punches followed by sectioning and probing with antibodies found that ex vivo tissue full thickness "buttons" have considerable heterogeneity (random occurrence of vessels, glands hair follicles etc) which stain differentially and interfere with quantification and reproducibility. In addition, both ex vivo tissue and differentiated culture models (that we produced ourself and purchased from outside vendors, for example Mattek, USA), for our studies, had low accuracy, sensitivity and specificity for the detection of dermal irritants or corrosives. Also, we could not imagine how live tissues could be developed into an easy to use and shelf stable test kit. Although there were years of effort without developing an accurate ex vivo or 3D tissue construct corrosion test, these experiments were not a total loss because for some of these studies we tried to identify potential markers of corrosion using enzyme conjugated antibodies. Typically, paraformaldehyde fixed tissues (which crosslinks proteins and inactivates most enzymes) are used for this type of histology. However, because we wanted to identify native protein markers, we used unfixed rabbit and pig skin. We noticed significant background endogenous phosphatase activity for skin treated with dermal noncorrosive, but this activity was not observed for skin treated with corrosives; skin has significant endogenous phosphatase activity, however skin treated with dermal corrosives did not continue to exhibit the endogenous phosphatase activity.

EXPERIMENTAL DETAILS AND EXAMPLES

Our initial studies involved using fresh and frozen porcine skin "buttons". These buttons were punched out of porcine skin (Spear Products, Cooopersburg, PA) using a 0.6 mm biopsy punch tool. Three different kinds of skin buttons were prepared from fresh porcine skin, frozen porcine skin, and frozen porcine skin with the fatty layer removed. Nine chemicals ((2-Bromoethyl)benzene, Triethylene glycol, 2-Methyl-4-phenyl-2-butanol, Heptanal, di-n-Propyl disulfide, Cyclamen aldehyde, Ethanolamine, Dimethyldipropylenetriamine, and Acetic acid) and two controls (water and naïve) were tested. Each skin button was put into a 96-well plate and dosed with 140 μL of the test substance for 30 minutes, then transferred to tubes containing 2 mL of phosphate buffered saline (PBS) with added sodium azide and incubated for 18 hours at 37° C. The next day, the tubes were taken out and vortexed and 500 μL of the solution was aliquoted into cuvettes to read at three different optical density wavelengths (OD190, OD290, OD300) to evaluate the best response.

Protocol:

Skin Button Experiment

First Week

Chemical List

| Condition | Chemical Name | CASRN | in vivo GHS |
|---|---|---|---|
| Water | | | |
| Naive | | | |
| C1 | (2-Bromoethyl)benzene | 103-63-9 | NC |
| C2 | Triethylene glycol | 112-27-6 | NC |
| C3 | 2-Methyl-4-phenyl-2-butanol | 103-05-9 | NC |
| C4 | Heptanal | 111-71-7 | Cat. 2 |
| C5 | di-n-Propyl disulfide | 629-19-6 | Cat. 2 |
| C6 | Cyclamen aldehyde | 103-95-7 | Cat. 2 |
| C7 | Ethanolamine | 141-43-5 | Cat. 1 |
| C8 | Dimethyldipropylenetriamine | 10563-29-8 | Cat. 1 |
| C9 | Acetic Acid | 64-19-7 | Cat. 1 |

Skin Preparation

1. Thaw 2 pieces of frozen porcine skin
2. Punch out buttons: 24 buttons in each tube filled with 40 mL PB S-Azide 96-well plate Preparation
1. Plate layout for dosing:

| | Water | Naïve | C1 | C2 | C3 | C4 | C5 | C6 | C7 | C8 | C9 |
|---|---|---|---|---|---|---|---|---|---|---|---|
| Original Tissue | | | | | | | | | | | |
| Frozen Tissue | | | | | | | | | | | |
| Frozen Fat Removed | | | | | | | | | | | |

Procedure

1. Dose each tissue with 140 μL of test chemical
2. Put into incubator for 3 hours and then transfer into 7 mL tubes filled with 2 mL of PBS-Azide, then put back into incubator for 18 hours Reading Results 1. Take out of incubator and vortex pulse 3×
2. Aliquot 500 μL to cuvette and read results at OD190, OD290, and OD300

Results are shown in as shown in Tables 1A-1C below.

TABLE 1A

Results from Initial Studies using Fresh Porcine Skin

| Chemical Name | CASRN | in vivo GHS | R | OD190 | OD290 | OD300 |
|---|---|---|---|---|---|---|
| Water | n/a | n/a | 1 | 0.124 | 0.147 | 0.108 |
| | | | 2 | 0.170 | 0.129 | 0.097 |
| Naive | n/a | n/a | 1 | 0.141 | 0.154 | 0.119 |
| | | | 2 | 0.313 | 0.250 | 0.213 |
| (2-Bromoethyl)benzene | 103-63-9 | NC | 1 | 0.128 | 0.125 | 0.080 |
| | | | 2 | 0.304 | 0.133 | 0.094 |
| Triethylene glycol | 112-27-6 | NC | 1 | 0.221 | 0.153 | 0.118 |
| | | | 2 | 0.372 | 0.105 | 0.068 |
| 2-Methyl-4-phenyl-2-butanol | 103-05-9 | NC | 1 | 0.210 | 0.339 | 0.272 |
| | | | 2 | 0.559 | 0.426 | 0.371 |
| Heptanal | 111-71-7 | Cat. 2 | 1 | 0.486 | 0.170 | 0.123 |
| | | | 2 | 0.365 | 0.165 | 0.123 |
| di-n-Propyl disulfide | 629-19-6 | Cat. 2 | 1 | 0.419 | 0.139 | 0.105 |
| | | | 2 | 0.400 | 0.137 | 0.096 |
| Cyclamen aldehyde | 103-95-7 | Cat. 2 | 1 | 0.694 | 0.290 | 0.274 |
| | | | 2 | 0.716 | 0.477 | 0.447 |
| Ethanolamine | 141-43-5 | Cat. 1BC | 1 | >3A | 0.848 | 0.711 |
| | | | 2 | >3A | 1.169 | 1.044 |
| Dimethyldipropylenetriamine | 10563-29-8 | Cat. 1A | 1 | >3A | 0.922 | 0.819 |
| | | | 2 | >3A | 1.016 | 0.887 |
| Acetic acid | 64-19-7 | Cat. 1A | 1 | >3A | 1.122 | 1.065 |
| | | | 2 | >3A | 0.931 | 0.857 |

TABLE 1B

Results from Initial Skin Button Studies using Frozen Porcine Skin

| Chemical Name | CASRN | in vivo GHS | R | OD190 | OD290 | OD300 |
|---|---|---|---|---|---|---|
| Water | n/a | n/a | 1 | 0.204 | 0.186 | 0.098 |
| | | | 2 | 0.184 | 0.177 | 0.080 |
| Naive | n/a | n/a | 1 | 0.299 | 0.19 | 0.092 |
| | | | 2 | 0.185 | 0.397 | 0.274 |
| (2-Bromoethyl)benzene | 103-63-9 | NC | 1 | 0.129 | 0.279 | 0.137 |
| | | | 2 | 0.272 | 0.254 | 0.128 |
| Triethylene glycol | 112-27-6 | NC | 1 | 0.231 | 0.156 | 0.072 |
| | | | 2 | 0.474 | 0.257 | 0.149 |
| 2-Methyl-4-phenyl-2-butanol | 103-05-9 | NC | 1 | 0.338 | 0.496 | 0.342 |
| | | | 2 | 0.362 | 0.637 | 0.497 |
| Heptanal | 111-71-7 | Cat. 2 | 1 | 0.362 | 0.245 | 0.154 |
| | | | 2 | 0.371 | 0.241 | 0.137 |
| di-n-Propyl disulfide | 629-19-6 | Cat. 2 | 1 | 0.314 | 0.294 | 0.161 |
| | | | 2 | 0.396 | 0.240 | 0.119 |
| Cyclamen aldehyde | 103-95-7 | Cat. 2 | 1 | >3A | 1.023 | 0.901 |
| | | | 2 | 0.675 | 0.955 | 0.852 |
| Ethanolamine | 141-43-5 | Cat. 1BC | 1 | >3A | 0.708 | 0.524 |
| | | | 2 | 0.550 | 0.767 | 0.598 |
| Dimethyldipropylenetriamine | 10563-29-8 | Cat. 1A | 1 | >3A | 0.936 | 0.806 |
| | | | 2 | >3A | 0.775 | 0.636 |
| Acetic acid | 64-19-7 | Cat. 1A | 1 | >3A | 1.002 | 0.935 |
| | | | 2 | >3A | 0.873 | 0.859 |

TABLE 1C

| | | | | | | |
|---|---|---|---|---|---|---|
| Results from Initial Skin Button Studies using Frozen Porcine Skin with Fat Layer Removed | | | | | | |
| Chemical Name | CASRN | in vivo GHS | R | OD190 | OD290 | OD300 |
| Water | n/a | n/a | 1 | 0.094 | 0.042 | 0.017 |
| | | | 2 | 0.106 | 0.065 | 0.027 |
| Naive | n/a | n/a | 1 | 0.105 | 0.069 | 0.020 |
| | | | 2 | 0.201 | 0.046 | 0.016 |
| (2-Bromoethyl)benzene | 103-63-9 | NC | 1 | 0.131 | 0.071 | 0.030 |
| | | | 2 | 0.144 | 0.080 | 0.034 |
| Triethylene glycol | 112-27-6 | NC | 1 | 0.101 | 0.054 | 0.016 |
| | | | 2 | 0.201 | 0.050 | 0.016 |
| 2-Methyl-4-phenyl-2-butanol | 103-05-9 | NC | 1 | 0.215 | 0.079 | 0.026 |
| | | | 2 | 0.322 | 0.094 | 0.052 |
| Heptanal | 111-71-7 | Cat. 2 | 1 | 0.144 | 0.111 | 0.040 |
| | | | 2 | 0.149 | 0.140 | 0.050 |
| di-n-Propyl disulfide | 629-19-6 | Cat. 2 | 1 | 0.443 | 0.082 | 0.031 |
| | | | 2 | 0.405 | 0.063 | 0.018 |
| Cyclamen aldehyde | 103-95-7 | Cat. 2 | 1 | 0.222 | 0.195 | 0.142 |
| | | | 2 | 0.214 | 0.153 | 0.119 |
| Ethanolamine | 141-43-5 | Cat. 1BC | 1 | 0.761 | 0.168 | 0.099 |
| | | | 2 | 0.800 | 0.093 | 0.048 |
| Dimethyldipropylenetriamine | 10563-29-8 | Cat. 1A | 1 | 0.610 | 0.238 | 0.162 |
| | | | 2 | 0.594 | 0.170 | 0.118 |
| Acetic acid | 64-19-7 | Cat. 1A | 1 | 0.591 | 0.054 | 0.040 |
| | | | 2 | 0.599 | 0.064 | 0.047 |

Interpretation of Tables 1A-1C: Nine chemicals ((2-Bromoethyl)benzene, Triethylene glycol, 2-Methyl-4-phenyl-2-butanol, Heptanal, di-n-Propyl disulfide, Cyclamen aldehyde, Ethanolamine, Dimethyldipropylenetriamine, and Acetic acid) and two controls (water and naïve) were tested on three different porcine skin (fresh, frozen, and frozen with the fatty layer removed). There were three readings done at an optical density of 190, 290, and 300 nm to evaluate the best response. At an optical density of 190 nm, the spectrophotometer readings were unstable and fluctuating while at 290 nm and 300 nm, the reading were stable with no fluctuations, therefore the optical density wavelength for the next study was chosen to be 300 nm. These results represent the presence of proteins, with higher readings containing a greater protein response and lower readings containing a lower protein response. As shown on Tables 1A and 1B, the response of the dermal corrosive chemicals was greater than the dermal irritants and nonirritants. However, as shown on Table 1C, the response of the dermal corrosive, dermal irritant, and dermal nonirritant chemicals were variable and therefore inconclusive. The responses from this study led us to critically think about the surface area of the skin buttons and how the test chemical (some viscous, some non-viscous) sits on the epidermis during the exposure period, such as whether it remains on strictly on the epidermis or if it drips down to the sides of the skin button and potentially changing the way the chemical is inducing toxicity to the skin button through the sides. To address the variable exposure conditions, our next studies involved placing a larger porcine skin section into a holder that exposes only the epidermis side with no potential for test chemical exposure from the backside or through the sides.

Our next studies involved applying the test substance (500 µL) directly to the epidermis side of previously frozen porcine skin (Spear Products, Coopersburg, PA) that is placed in a holder that only exposes the epidermis side for 30 minutes, adding phosphate buffered saline (PBS) with added sodium azide (metabolic inhibitor that ensure no viable tissue), then aliquoting into cuvettes to read at an optical density of 300 nm. The results were inconclusive since the aliquoted solution in the cuvettes were opaque and giving the same reading of >3A (outside of the spectrophotometer's readable range). We then tried the Lowry Method for a different method of protein determination, but results were also inconclusive because there was no clear difference in color change for the test substances and controls. After multiple studies trying to looking for skin damage, changes in viability, released factors and damage and not finding anything significant, as an afterthought after a failed experiment, we recalled prior experience (described above) doing histology on skin cross sections treated with dermal corrosives, where we noticed that maybe the phosphatase activity was reduced after exposure to skin corrosives. So, at the end of the initial studies described above, almost out of frustration, we tried to probe for released phosphatase activity using p-Nitrophenyl phosphate disodium salt (PNPP; Sigma Aldrich, St. Louis, MO) substrate solution to detect any presence of phosphatase. After removing the chemical, we added 1 mL of PNPP and incubated for 48 hours. We then recovered the incubated p-Nitrophenyl phosphate disodium salt (PNPP) from each of the different skin sections and read the optical density at 405 nm and results are shown in Table 2 below.

Protocol:

Skin Experiment

Second Week

Chemical List

| Condition | Chemical Name | CASRN | in vivo GHS |
|---|---|---|---|
| Water | | | |
| C1 | (2-Bromoethyl)benzene | 103-63-9 | NC |
| C2 | Triethylene glycol | 112-27-6 | NC |
| C3 | 2-Methyl-4-phenyl-2-butanol | 103-05-9 | NC |
| C4 | Heptanal | 111-71-7 | Cat. 2 |
| C5 | di-n-Propyl disulfide | 629-19-6 | Cat. 2 |

-continued

| Condition | Chemical Name | CASRN | in vivo GHS |
|---|---|---|---|
| C6 | Cyclamen aldehyde | 103-95-7 | Cat. 2 |
| C7 | Ethanolamine | 141-43-5 | Cat. 1 |
| C8 | Dimethyldipropylenetriamine | 10563-29-8 | Cat. 1 |
| C9 | Acetic Acid | 64-19-7 | Cat. 1 |
| Naive | Note: If enough tissue discs | | |

Preparation
1. Thaw 2 pieces of frozen porcine skin
   a. Punch out as many skin discs and mount in holders
2. Label cuvettes (3 for each chemical)
Procedure
1. Add 500 μL of test chemical to holder; incubate at room temperate for 30 minutes
2. After 30 minutes, add 2 mL of PBS-Azide to both the holder containing the test chemical; forcefully pipette and re-pipette 10 times
3. From the holder, aliquot 400 μL into 3 cuvettes; forcefully pipette and re-pipette 3 times before dispensing into cuvettes
Reading Results
1. Measure at OD300 for all cuvettes

TABLE 2

Results from Initial Skin Holder Studies with Frozen Skin Sections

| Chemical Name | CASRN | in vivo GHS | Corrosive | Reading 1 | Reading 2 |
|---|---|---|---|---|---|
| Water | n/a | n/a | No | >3A | >3A |
| Naive | n/a | n/a | No | >3A | >3A |
| (2-Bromoethyl)benzene | 103-63-9 | NC | No | >3A | >3A |
| Triethylene glycol | 112-27-6 | NC | No | 0.886 | 0.845 |
| 2-Methyl-4-phenyl-2-butanol | 103-05-9 | NC | No | 2.957 | >3A |
| Heptanal | 111-71-7 | Cat. 2 | No | >3A | 2.831 |
| di-n-Propyl disulfide | 629-19-6 | Cat. 2 | No | 2.044 | 2.148 |
| Cyclamen aldehyde | 103-95-7 | Cat. 2 | No | >3A | >3A |
| Ethanolamine | 141-43-5 | Cat. 1BC | Yes | 0.603 | 0.587 |
| Dimethyldipropylenetriamine | 10563-29-8 | Cat. 1A | Yes | 0.706 | 0.531 |
| Acetic acid | 64-19-7 | Cat. 1A | Yes | 0.574 | 0.559 |

CASRN = Chemical Abstracts Service Registry Number;
GHS = Globally Harmonized System of Classification and Labeling of chemicals;
n/a = Not Applicable;
NC = Not Classified;
>3A = Reading outside of the spectrophotometer's readable range.

Interpretation of Table 2: Nine chemicals ((2-Bromoethyl) benzene, Triethylene glycol, 2-Methyl-4-phenyl-2-butanol, Heptanal, di-n-Propyl disulfide, Cyclamen aldehyde, Ethanolamine, Dimethyldipropylenetriamine, and Acetic acid) and two controls (water and naïve) were added to the epidermis of previously frozen porcine skin sections to evaluate skin corrosion potential after a 30 minute exposure. Using the measured optical density values compared to the naïve condition to get the percent of phosphatase measured, the three GHS Category 1 chemicals (Ethanolamine: 20.1%, 19.6%, average 19.9%; Dimethyldipropylenetriamine: 23.5%, 17.7%, average 20.6%; Acetic acid: 19.1%, 18.6%, average 18.9%) showed a significantly lower response than the dermal irritants (Heptanal: 100.0%, 94.4%, average 97.2%; di-n-Propyl disulfide: 68.1%, 71.6%, average 69.9%; Cyclamen aldehyde: 100.0%, 100.0%, average 100.0%) or nonirritants ((2-Bromoethyl)benzene: 100.0%, 100.0%, average 100.0%; 2-Methyl-4-phenyl-2-butanol: 98.6%, 100.0%, average 99.3%) with the exception of Triethylene glycol (29.5%, 28.2%, average 28.9%) which had low response. As shown in Table 2, to our surprise there was significantly less phosphatase activity for the dermal corrosives (Ethanolamine: 0.603, 0.587; Dimethyldipropylenetriamine: 0.706, 0.531; Acetic Acid: 0.574, 0.559) compared with the dermal irritants (Heptanal: >3A, 2.831; di-n-Propyl disulfide: 2.044, 2.148; Cyclamen aldehyde: >3A, >3A) or nonirritants ((2-Bromoethyl)benzene: >3A, >3A; Triethylene glycol: 0.886, 0.845; 2-Methyl-4-phenyl-2-butanol: 2.957, >3A). Skin corrosion by GHS Category 1 dermal corrosive chemicals results in the disintegration of the epidermis into the dermis. This was the first experiment where we discovered that dermal corrosives inhibited enzyme activity. Based on the preliminary discovery, shown in Table 2, we set out to further explore and optimize the study with a larger focus on the phosphatase and p-Nitrophenyl phosphate disodium salt (PNPP) substrate system.

Figure 1:
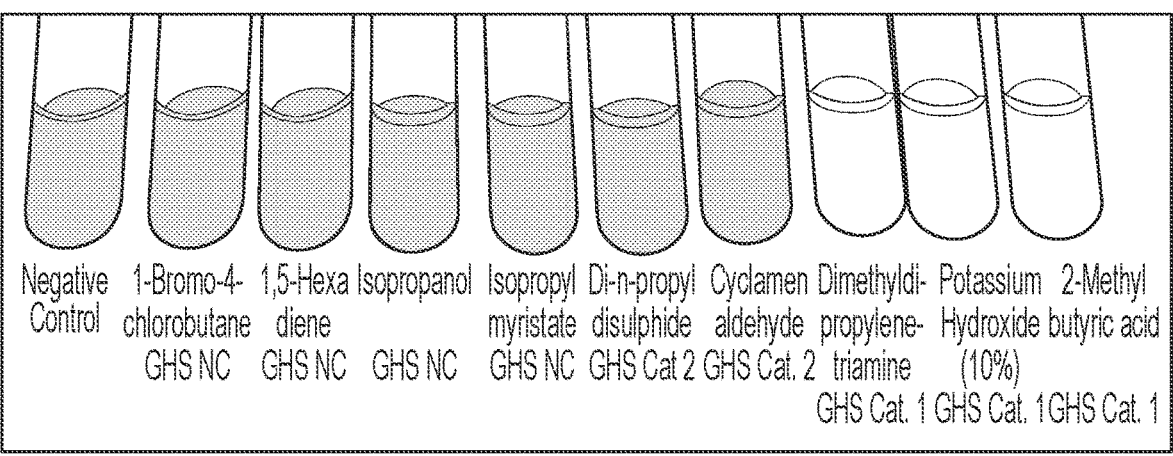
FIG. 1 depicts test results for 3 skin corrosives (clear vials on right "GHS Cat 1")) compared with 6 noncorrosives ("GHS NC and Cat 2") and a negative control (water, on the far left). Enzyme was diluted and chemicals were aliquoted into glass tubes at a ratio of 1:10 (100 mg/ml). The chemical/ enzyme solutions were incubated for 4 hours at room temperature. After incubation, 2 mls of an enzyme substrate that turns from clear to yellow was added to each tube, and then tubes ere incubated at room temperature for 1 hour. Results for corrosives show almost complete enzyme inhibition as indicated by the clear tube without observable yellow reaction product versus the other tubes with enzyme incubated with noncorrosives which have an obvious high concentration of yellow reaction product. Using this method, a test material could be tested for toxicity in a field setting without equipment.
Figure 2:
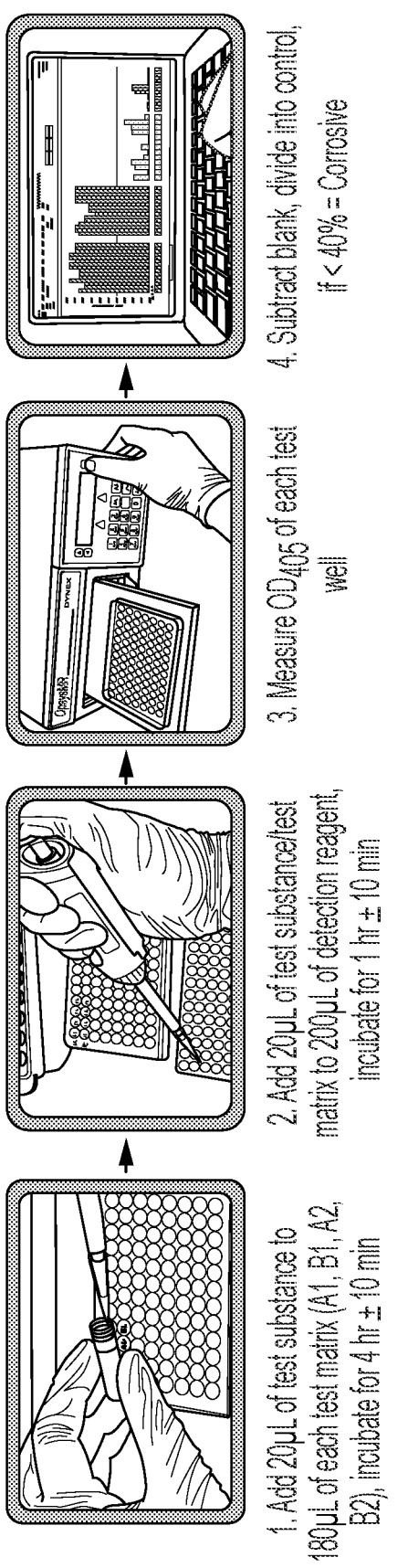
FIG. 2 depicts how to conduct and quantify an embodiment of an in chemico test in the laboratory. The material to be tested, plus the controls, are added directly to the enzyme solution. After an incubation, aliquots are added to the "detection reagent" (enzyme substrate), which strongly absorbs when active. This reaction is quantified using a plate reader, the backgrounds are subtracted, the resulting net OD values are normalized by dividing into the net ODs of the corresponding background subtracted negative controls, and the result with the lower percentage is the "In Chemico (IC) value", which is used to determine if the material tested is a toxic.

Our next study focused on an in vitro method of detecting the potential of dermal corrosives to inhibit nonspecific phosphatases that may be released from the skin. We decided to test pure phosphate instead of relying on endogenous skin phosphatase. Alkaline phosphatase (Sigma Aldrich, St. Louis, MO) was purchased and suspended to make the reaction reagent (10,000 units). We conducted an initial pilot study by suspending alkaline phosphatase in saline and then adding the chemicals to be tested at ratio of 1 part chemical to 9 parts enzyme suspension. We note that the ratio used was 0.1 g/ml or 10% chemical—which is far in excess of any pharmaceutical applications. We further note that pharmaceutical enzyme inhibition tests, studies an use involve highly specific active site binding and these assays are conducted at ratios of micrograms-femtograms per ml. These studies are done at these ranges because these are the realistic concentrations for drug applications and therapeutics. For example, the desired working dose—a single tablet to be consumed by a human, might have 5 mg of drug. So when a 50 Kg human consumes the tables, the tissues will be exposed at a 5 mg/50 kg=0.1 mg/kg=0.0000001 g/ml. So while both the method described here and pharmaceutical uses may inhibit enzymatic activity, the concentration used for the method described here is around 6 orders of magnitude greater than used for specific drug active site or regulatory site binding drug effects. On the other hand, the method disclosed here is nonspecific and the active site, regulatory sites, and the entire enzyme are destroyed or inactivated as a result of a very high concentration of the chemical being tested and the resulting generalized not specific molecular damage by the toxin being tested. FIG. 1 shows our pilot results where we added 3 dermal corrosives and 6 dermal noncorrosives to an enzyme solution at a ratio of 0.1 g chemical/ml enzyme solution, incubated for 4 hours at room temperature and then added a clear enzyme substrate that turns yellow when the enzyme is active, the enzyme remains active for noncorrosive (yellow tubes) and is inactive for dermal corrosives (clear tubes).

Next two quantitative methods were evaluated: 1) using the discs parts from our OptiSafe™ test method and 2) directly into the 24-well plate. For the first exposure method, 100 μL of the test chemical was added to the center of the ocular disc, placed in a 24-well plate containing 1.25 mL of the alkaline phosphatase reaction reagent (10,000 units), and incubated at 37° C. for 18 hours. For the second exposure method, 100 μL of the test chemical was added to the corresponding well of a 24-well plate containing 1.25 mL of the alkaline phosphatase reaction reagent, mixed with the same pipette tip, wrapped, and incubated at 37° C. for 18 hours. The next day, 20 μL of the alkaline phosphatase reaction reagent in the wells were added to a 96-well plate containing 200 μL of p-Nitrophenyl phosphate disodium salt (PNPP) substrate solution, incubated for 1 hour and results were read at 405 nm using a spectrophotometer.

Protocol:

Alkaline Phosphatase Experiment

Third Week

Chemical List

| Condition | Chemical Name | CASRN | in vivo GHS |
|---|---|---|---|
| PBS | | | |
| C1 | (2-Bromoethyl)benzene | 103-63-9 | NC |
| C2 | Triethylene glycol | 112-27-6 | NC |
| C3 | 2-Methyl-4-phenyl-2-butanol | 103-05-9 | NC |
| C4 | Cyclamen aldehyde | 103-95-7 | Cat. 2 |
| C5 | Heptanal | 111-71-7 | Cat. 2 |
| C6 | di-n-Propyl disulfide | 629-19-6 | Cat. 2 |
| C7 | Ethanolamine | 141-43-5 | Cat. 1 |
| C8 | Dimethyldipropylenetriamine | 10563-29-8 | Cat. 1 |
| C9 | Acetic Acid | 64-19-7 | Cat. 1 |
| Naive | | | |

Preparation

1. Alkaline phosphatase reaction reagent
   a. Take 1 vial of AP, add 1 mL of PBS, mix by pipette/re-pipette 10 times
   b. To a 50 mL conical tube, add 1 mL of the AP solution prepared above and 40 mL of PBS
2. Prepare two 24-well plates (1 with discs, 1 without discs)
3. Prepare two 96-well plates for PNPP reading (3 wells for each test chemical)
   a. Aliquot 200 μL PNPP and PBS Procedure 1. Plate 1 (No Discs)
   a. Add 1.25 mL from the prepared PBS-AP conical tube to each well (11 wells)
   b. Add 100 μL of the test material to the well, mix with the same pipette tip, dispose and repeat for the rest of the test materials
   c. Wrap the plate in saran wrap and place into the container
2. Plate 2 (Discs)
   a. Configure the 11 discs in the plate so the plate cover is stable
   b. Add 1.25 mL from the prepared PBS-AP conical tube to each well (11 wells)

c. Add 100 μL of the test material to the center of the disc and repeat for the rest of the test materials
   d. Put the plate cover on and place into the container
3. Incubate for 18 hours at 37° C.
4. To the prepared 96-well plates with 200 μL PNPP and PBS, add 20 μL from the 24-well plate
5. Incubate for 1 hour Reading Results 1. Measure at OD405
   The results are shown in FIGS. 3A and 3B.
   Interpretation of FIGS. 3A and 3B: The same nine chemicals (C1: (2-Bromoethyl)benzene, C2: Triethylene glycol, C3: 2-Methyl-4-phenyl-2-butanol, C4: Cyclamen aldehyde, C5: Heptanal, C6: di-n-Propyl disulfide, C7: Ethanolamine, C8: Dimethyldipropylenetriamine, and C9: Acetic acid) were tested in a new study to find the best exposure method by comparing results with and without ocular discs. As shown in FIGS. 3A and 3B, there was no significant difference in the readings between the two methods and so the without discs was chosen to keep the test method less complicated. In FIG. 3A, the results for the three dermal corrosives (C7 [Ethanolamine]: 0.170, 0.166, 0.172; C8 [Dimethyldipropylenetriamine]: 0.152, 0.159, 0.140; C9 [Acetic acid]: 0.106, 0.102, 0.103) were much lower than the dermal irritants and nonirritants (C1 [(2-Bromoethyl)benzene], C2 [Triethylene glycol], C3 [2-Methyl-4-phenyl-2-butanol], C4 [Cyclamen aldehyde], C5 [Heptanal], C6 [di-n-Propyl disulfide]) which were all above 3.000, which suggests that there was no inhibition of alkaline phosphatase. In FIG. 3B, the results for the three dermal corrosives (C7 [Ethanolamine]: 0.174, 0.185, 0.175; C8 [Dimethyldipropylenetriamine]: 0.138, 0.176, 0.133; C9 [Acetic acid]: 0.104, 0.129, 0.101) were lower than the dermal irritants and nonirritants (C1 [(2-Bromoethyl)benzene], C2 [Triethylene glycol], C3 [2-Methyl-4-phenyl-2-butanol], C4 [Cyclamen aldehyde], C5 [Heptanal], C6 [di-n-Propyl disulfide]) which were all above 3.000, which suggests that there was no inhibition of alkaline phosphatase. This results expanded our discovery, since dermal corrosives had the potential to inhibit purified alkaline phosphatase outside of the tissue, therefore the p-Nitrophenyl phosphate disodium salt (PNPP) substrate system could not detect the presence of alkaline phosphatase. For the blank reaction reagents, no alkaline phosphatase was added to the reagent to account for any chemical interference in OD value. We tested two conditions (with and without discs) to evaluate the need for a controlled entry of the test chemical to the reaction reagent, however, based on the results of this experiment, the results show that the discs were not needed. For analysis purposes, if we set the corrosive cut-off to less than about 0.500, then this study shows that our test system has correctly identified the dermal corrosives. With these results, we decided to repeat this study and proceed forward to the next study to optimize the exposure period and p-Nitrophenyl phosphate disodium salt (PNPP) incubation period.

Our next study included repeating the previous study (no ocular discs method) and introducing a new study with a test chemical exposure period of 10 minutes and p-Nitrophentyl phosphate disodium salt (PNPP) incubation period range of 10 minutes, 1 hour, 4 hours, and 18 hours. For the new study, the alkaline phosphatase was suspended in phosphate buffered saline (PBS) to make the reaction reagent. Then, 100 μL of the test chemical is added directly into the corresponding wells on a 24-well plate with 1.25 mL of alkaline phosphatase reaction reagent already aliquoted. After 10 minutes, the wells are mixed with the pipette tip and 20 μL of the reaction reagent is aliquoted into a 96-well plate containing 200 μL of p-Nitrophenyl phosphate disodium salt (PNPP) and phosphate buffered saline (PBS; blank). The p-Nitrophenyl phosphate disodium salt (PNPP) results are then read after 10 minutes, 1 hour, 4 hours, and 18 hours of incubation at 37° C.

Protocol:
Alkaline Phosphatase Experiment
Fourth Week
Chemical List

| Condition | Chemical Name | CASRN | in vivo GHS |
|---|---|---|---|
| PBS | | | |
| C1 | 1-Bromo-4-chlorobutane | 6940-78-9 | NC |
| C2 | 1,5-Hexadiene | 592-42-7 | NC |
| C3 | Isopropanol | 67-63-0 | NC |
| C4 | Isopropyl Myristate | 110-27-0 | NC |
| C5 | di-n-Propyl Disulphide | 629-19-6 | Cat. 2 |
| C6 | Cyclamen aldehyde | 103-95-7 | Cat. 2 |
| C7 | Dimethyldipropylenetriamine | 10563-29-8 | Cat. 1 |
| C8 | Potassium hydroxide (10%) | 1310-58-3 | Cat. 1 |
| C9 | 2-Methyl butyric acid | 116-53-0 | Cat. 1 |
| Naive | | | |

Preparation
1. Alkaline phosphatase reaction reagent
    a. Take 1 vial of AP, add 1 mL of PBS, mix by pipette/re-pipette 10 times
    b. To a 50 mL conical tube, add 1 mL of the AP solution prepared above and 40 mL of PBS
2. Prepare two 24-well plates
3. Prepare two 96-well plates for PNPP reading (3 wells for each test chemical)
    a. Aliquot with 200 μL PNPP and PBS
4. Prepare glass vials
Repeat Procedure from 1-3-23
1. 24-well plate
    a. Add 1.25 mL from the prepared PBS-AP conical tube to each well (11 wells)
    b. Add 100 μL of the test material to the well, mix with the same pipette tip, dispose and repeat for the rest of the test materials
    c. Wrap the plate in saran wrap and place into the container
2. Incubate for 18 hours at 37° C.
3. To the prepared 96-well plate with 200 μL PNPP or PBS, add 20 μL from the 24-well plate
4. Incubate for 1 hour
5. Measure at 405 nm
Procedure
1. 24-well plate
    a. Add 1.25 mL from the prepared PBS-AP conical tube to each well (11 wells)
    b. Add 100 μL of the test material to the well, mix with the same pipette tip, dispose and repeat for the rest of the test materials
    c. After 10 minutes, mix each well
2. To the prepared 96-well plate with 200 μL PNPP or PBS, add 20 μL from the 24-well plate
3. Measure at 10 minutes, 1 hour, 4 hours, 18 hours
Test Tube Procedure
1. Aliquot 200 μL from the 24-well plate to glass vials filled with 2 mL of PNPP
The results from the repeated study are shown in FIG. 4, results for the different p-Nitrophenyl phosphate disodium salt (PNPP) incubation periods are shown below in FIGS. 5A-5D, and results from the visual test tube study are shown in FIG. 1.

Interpretation of FIG. 1, FIG. 4, and FIGS. 5A-5D: In the repeat of the previous study, we concluded that results were reproducible and the best exposure method was directly adding to the well containing the alkaline phosphatase reaction reagent For example, as shown on FIG. 4, the results for the dermal corrosives (C7 [Dimethyldipropylenetriamine]: 0.132, 0.128, 0.127); C8 [Potassium hydroxide (10%)]: 0.123, 0.124, 0.124; C9 [2-Methylbutyric acid]: 0.138, 0.138, 0.137) were still significantly less than the dermal irritants or nonirritants (C1 [1-Bromo-4-chlorobutane), C2 [1,5-Hexadiene], C3 [Isopropanol], C4 [Isopropyl myristate], C5 [di-n-Propyl disulfide], C6 [Cyclamen aldehyde]) which had readings above 3.000. For the 10-minute test chemical exposure study, we concluded that this exposure period was too fast and not enough time for the dermal corrosives to interact with the alkaline phosphatase reaction reagent. This study concluded the optimal exposure period was 18 hours with a p-Nitrophenyl phosphate disodium salt (PNPP) incubation period of 1-hour. For example, for Dimethyldipropylenetriamine, the 10-minute PNPP incubation readings were 3.449, 3.502, and 3.500 (FIG. 5A), the 1-hour PNPP incubation readings were 0.352, 0.283, and 0.333 (FIG. 5B), the 4-hour PNPP incubation readings were 0.122, 0.116, and 0.114 (FIG. 5C), and the 18-hour PNPP incubation readings were 0.112, 0.105, and 0.110 (FIG. 5D). Therefore, based on these results, the most optimal PNPP incubation period was 1-hour. As shown in FIG. 1, we did a visual study by adding 200 μL to 2 mL of p-Nitrophenyl phosphate disodium salt (PNPP) substrate solution to see the color reaction and observed no color for the dermal corrosive chemicals whereas the dermal irritants and nonirritants all turned yellow (FIG. 1). Then, for our next study, we obtained another source of alkaline phosphatase (Sigma Aldrich, St. Louis, MO; Catalog No. P7640) to try to optimize the concentration of alkaline phosphatase present in the reaction reagent to mediate the p-Nitrophenyl phosphate disodium salt (PNPP) reaction's color intensity.

Our next study compared different dilutions of the original alkaline phosphatase source (1:10 [Activity: 1,000 units] and 1:100 [100 units]) and two sources of alkaline phosphatase, both purchased from Sigma Aldrich (St. Louis, MO). The first alkaline phosphatase (Catalog No. P0114) is a buffered aqueous glycerol solution with 10,000 units, a specific activity of ≥5,700 DEA units/mg protein, and concentration of ≥10 mg/mL; this was the original alkaline phosphatase used for the previous studies. The second alkaline phosphatase (Catalog No. P7640) is a lyophilized powder with a specific activity of ≥10 DEA units/mg solid; this was prepared by adding 400 mg to 40 mL of phosphate buffered saline (PBS). The five conditions for this study included original alkaline phosphatase (1:1), original alkaline phosphatase (1:10), original alkaline phosphatase (1:100), new alkaline phosphatase (1:1), and the blanks (phosphate buffered saline (PBS)). Four controls (Water, Water/1% Ink, Acetic acid, Acetic acid/1% Ink) and thirty chemicals (1,5-Hexadiene, Isopropanol, 4-(Methylthio)benzaldehyde, Isopropyl myristate, Benzyl salicylate, Phenylethyl alcohol, Hydroxycitronellal, Benzyl acetate, Dipropylene glycol, di-n-propyl disulfide, 1-Bromopentane, Cyclamen aldehyde, cis-3-Methyl-2-(2-pentenyl)-2-cyclopenten-1-one, p-Metha-1,8-dien-7-ol, Heptanal, trans-3,7-Dimethyl-2,6-octadien-1-ol, alpha-Terpineol, 1-Decanol, Nonyl aldehyde, Dimethyldipropylenetriamine, Potassium hydroxide (10%), 2-Methylbutyric acid, Octanoic acid, Dimethylisopropylamine, 2-tert-Butylphenol, 5-Isopropyl-2-methylphenol, n-Heptylamine, Methoxy-3-propylamine, N,N-Dimethylbenzylamine) were tested. The two controls contained ink to determine if there would be any background effect. In a 24-well plate, 1 mL of each condition's reaction reagent was added to the corresponding well and then 100 µL of the test chemical was added, mixed with the pipette tip, and incubated for 18 hours at room temperature. The next day, 96-well plates were prepared with 200 µL of p-Nitrophenyl phosphate disodium salt and phosphate buffered saline (blanks) and then 20 µL from the 24-well plates was added and incubated for 1 hour with results read at 405 nm.

Protocol:

Alkaline Phosphatase Experiment

Fifth Week

Chemical List

| Chemical No. | Chemical Name | CASRN | in vivo GHS |
|---|---|---|---|
| 1 | NC1: Water | | |
| 2 | NC2: Water/1% Ink | | |
| 3 | PC1: Acetic Acid | | |
| 4 | PC2: Acetic Acid/1% Ink | | |
| 5 | 1-Bromo-4-chlorobutane | 6940-78-9 | NC |
| 6 | 1,5-Hexadiene | 592-42-7 | NC |
| 7 | Isopropanol | 67-63-0 | NC |
| 8 | 4-(Methylthio)benzaldehyde | 3446-89-7 | NC |
| 9 | Isopropyl Myristate | 110-27-0 | NC |
| 10 | Benzyl Salicylate | 118-58-1 | NC |
| 11 | Phenylethyl alcohol | 60-12-8 | NC |
| 12 | Hydroxycitronellal | 107-75-5 | NC |
| 13 | Benzyl Acetate | 140-11-4 | NC |
| 14 | Dipropylene glycol | 25265-71-8 | NC |
| 15 | di-n-Propyl Disulfide | 629-19-6 | Cat. 2 |
| 16 | 1-Bromopentane | 110-53-2 | Cat. 2 |
| 17 | Cyclamen aldehyde | 103-95-7 | Cat. 2 |
| 18 | cis-3-Methyl-2-(2-pentenyl)-2-cyclopenten-1-one | 488-10-8 | Cat. 2 |
| 19 | p-Metha-1,8-dien-7-ol | 18457-55-1 | Cat. 2 |
| 20 | Heptanal | 111-71-7 | Cat. 2 |
| 21 | trans-3,7-Dimethyl-2,6-octadien-1-ol | 106-24-1 | Cat. 2 |
| 22 | alpha-Terpineol | 98-55-5 | Cat. 2 |
| 23 | 1-Decanol | 112-30-1 | Cat. 2 |
| 24 | Nonyl aldehyde | 124-19-6 | Cat. 2 |
| 25 | Dimethyldipropylenetriamine | 10563-29-8 | Cat. 1A |
| 26 | Potassium hydroxide (10%) | 1310-58-3 | Cat. 1B |
| 27 | 2-Methylbutyric acid | 116-53-0 | Cat. 1B/1C |
| 28 | Octanoic Acid | 124-07-02 | Cat. 1B/1C |
| 29 | Dimethylisopropylamine | 996-35-0 | Cat. 1B/1C |
| 30 | 2-tert-Butylphenol | 88-18-6 | Cat. 1B/1C |
| 31 | 5-Isopropyl-2-methylphenol | 499-75-2 | Cat. 1B/1C |
| 32 | n-Heptylamine | 111-68-2 | Cat. 1B/1C |
| 33 | Methoxy-3-propylamine | 5332-73-0 | Cat. 1B/1C |
| 34 | N,N-Dimethylbenzylamine | 103-83-3 | Cat. 1C |

Preparation

1. Alkaline phosphatase reaction reagent
   a. Original AP
      i. Add 1 mL PBS into AP vial, pipette re-pipette 10 times, then invert with cap on, to mix well. Take this 1 mL and add to 50 mL conical tube filled with 40 mL PBS. Invert to mix 10 times, vortex mix, let sit 2 minutes, invert to mix again 10 times
      ii. Prepare 2 more 50 mL conical tubes
         1. 1:10
            a. Take 4 mL of solution made above, add to 36 mL PBS. vortex mix and then invert to mix 10 times
         2. 1:100
            a. Take 4 mL of solution made above, add to 36 mL PBS. Vortex mix and then invert to mix 10 times b. New AP
      i. Add 400 mg into a 50 mL conical tube filled with 40 mL PBS. Invert to mix 10 times, vortex mix, let sit 2 minutes, invert to mix 10 more times. Check to make sure all suspended. If not, vortex mix and invert until fully suspended.
2. Prepare 24-well plates
3. Prepare six 96-well plates for PNPP reading (3 wells for each test chemical)
   a. Aliquot with 200 µL PNPP Conditions 1. Old AP
2. Old AP (1:10)
3. Old AP (1:100)
4. New AP
5. Blank (PBS only)

Procedure 1. 24-well plates
   a. Add 1 mL (using P1000, blue tips) of the prepared PBS-AP to the plate (for each condition)
   b. Add 100 µL of the test material to the well, mix with the same pipette tip, dispose and repeat for the rest of the test materials
   c. Wrap the plate in saran wrap and place into the container
   d. Incubate for 18 hours at room temperature
2. To the prepared 96-well plate with 200 µL PNPP or PBS, add 20 µL from the 24-well plate
3. Incubate for 1 hour
4. Read at 405 nm Results from this study are shown in FIGS. 6A-6F. From this study, we concluded that a good alkaline phosphatase source was the original source (Sigma Aldrich, St. Louis. MO; Catalog No. P0114) but both will work and the best reaction reagent concentration was at 1:100 (100 units).

Interpretation of FIGS. 6A-6F: As shown in FIG. 6B, the alkaline phosphatase concentration of 1:1 appears to be saturated and too high a concentration because it resulted in maximum or close to maximum OD405 readings for all chemicals except for No. 25 Dimethyldipropylenetriamine and No. 26 Potassium hydroxide (10%). The other dermal corrosives (No. 27 2-Methylbutyric acid, No. 28 Octanoic acid, No. 29 Dimethylisopropylamine, No. 30 2-tert-Butylphenol, No. 31 5-Isopropyl-2-methylphenol, No. 32 n-Heptylamine, No. 33 Methoxy-3-propylamine, and No. 34 N,N-Dimethylbenzylamine were incorrectly predicted based on the high OD405 values. As shown in FIG. 6C, for the 1:10 dilution, there was still a high OD405 reading for most dermal corrosives, however, the results for No. 25 Dimethyldipropylenetriamine were now mispredicted. This dilution corrected for No. 27 2-Methylbutyric acid and No. 33 Methoxy-3-propylamine. As shown in FIG. 6D, the 1:100 dilution correctly predicted No. 25 Dimethyldipropylenetriamine, No. 26 Potassium hydroxide (10%), No. 27 2-Methylbutyic acid, No. 30 2-tert-Butylphenol, and No. 33 Methoxy-3-propylamine. As shown in FIG. 6D, for the chemicals that did not cause a significant reduction in enzyme activity (No. 28 Octanoic acid [3.462, 3.491, 3.333]; No. 29 Dimethylisopropylamine [3.466, 3.502, 3.502]; No. 31 5-Isopropyl-2-methylphenol [0.991, 0.974, 1.167]; No. 32 n-Heptylamine [3.244, 3.057, 3.152]; No. 34 N,N-Dimethylbenzylamine [3.431, 3.502, 3.61]), we studied the chemical and questioned the solubility of these chemicals in phosphate buffered saline (PBS) and further researched their properties and found that these were mostly insoluble with water and therefore in the next experiments we tried some different solvents.

In our next study, we screened different solvents (dimethyl sulfoxide [DMSO], methanol, ethanol, acetone, vegetable oil, and mineral oil) by adding 200 µL of the solvent into 2 mL of p-Nitrophenyl phosphate disodium salt (PNPP) in a 24-well plate and letting the plate sit for 1-hour. The results were not quantified with the spectrophotometer but the color change was visually observed. The solvents with the brightest yellow intensity similar to water were ethanol, acetone, and vegetable oil, while the lesser yellow intensity were methanol and mineral oil and no response (clear) was seen with dimethyl sulfoxide (DMSO). With these results, we proceeded to the main experiment with two solvents picked, ethanol and acetone. Three alkaline phosphatase reaction reagents (concentration 1:10) were tested: phosphate buffered saline (PBS), ethanol, and acetone. Twelve chemicals were selected (water, methanol, mineral oil, 1-Bromo-4-chlorobutane, 1,5-Hexadiene, di-n-propyl disulfide, Nonyl aldehyde, Octanoic acid, Dimethylispropylamine, 5-Isopropyl-2-methylphenol, n-Heptylamine, N,N-Dimethylbenzylamine). Two different dosing concentrations were evaluated, 10 L of test chemical added to 90 µL of alkaline phosphatase reaction reagent and 50 µL of test chemical added to 50 µL of alkaline phosphatase reaction reagent; all aliquoted in 96-well plates. After dosing, the 96-well plates were incubated for 3 hours and 22 hours at room temperature and 20 µL was added to a different 96-well plate containing 200 µL of p-Nitrophenyl phosphate disodium salt (PNPP) and incubated for 30-minutes and 1-hour at room temperature for the 3-hour exposure and then 10-minutes, 30-minutes, and 1-hour for the 22-hour exposure. We observed some wells had evaporated or melted and could not recover to quantify using the spectrophotometer at an optical density of 405 nm, as shown in FIGS. 7A-7B and FIGS. 8A-8C.

Protocol:

Alkaline Phosphatase Experiment

Sixth Week

Chemical List

| Chemical No. | Chemical Name | CASRN | in vivo GHS |
|---|---|---|---|
| 1 | Water | n/a | n/a |
| 2 | Methanol | 67-56-1 | n/a |
| 3 | Mineral Oil | 8042-47-5 | n/a |
| 4 | 1-Bromo-4-chlorobutane | 6940-78-9 | NC |
| 5 | 1,5-Hexadiene | 592-42-7 | NC |
| 6 | di-n-Propyl Disulfide | 629-19-6 | Cat. 2 |
| 7 | Nonyl aldehyde | 124-19-6 | Cat. 2 |
| 8 | Octanoic Acid | 124-07-02 | Cat. 1B/1C |
| 9 | Dimethylisopropylamine | 996-35-0 | Cat. 1B/1C |
| 10 | 5-Isopropyl-2-methylphenol | 499-75-2 | Cat. 1B/1C |
| 11 | n-Heptylamine | 111-68-2 | Cat. 1B/1C |
| 12 | N,N-Dimethylbenzylamine | 103-83-3 | Cat. 1C |

Preparation

1. Alkaline phosphatase reaction reagent (fresh, 1:100)
    a. Take 4 mL of AP (1:10) stock solution, add to 36 mL PBS. Vortex mix and then invert to mix 10 times
2. Prepare alkaline phosphatase reaction reagent for every condition
    a. 200 µL AP (1:10) in 1.8 mL PBS
    b. 200 µL AP (1:10) in 1.8 mL Ethanol
    c. 200 µL AP (1:10) in 1.8 mL Acetone 3. Prepare 96-well plates for dosing
4. Prepare 96-well plates for PNPP reading (3 wells for each test chemical)
    a. Aliquot with 200 µL PNPP Conditions
    1. 1:10 in PBS (A)
    2. 1:10 in Ethanol (B)
    3. 1:10 in Acetone (C)

Procedure
    1. Set 1
        a. 10 µL chemical added to 90 µL AP reaction reagent
    2. Set 2
        a. 50 µL chemical added to 50 µL AP reaction reagent
    3. Incubate for 3 hours
        a. To the prepared 96-well plate with 200 µL PNPP aliquoted, add 20 µL
        b. Read results at 405 nm at 30 minutes and 1 hour
    4. Hold remainder for 18 hours
        a. To the prepared 96-well plate with 200 µL PNPP aliquoted, add 20 µL
        b. Read results at 405 nm at 10 minutes, 30 minutes, and 1 hour Interpretation of FIGS. 7A-7B and FIGS. 8A-8C: Twelve chemicals were selected to screen three solvents (buffered saline, ethanol, and acetone) to try to troubleshoot the dermal corrosive chemicals in the previous study that did not have the expected low results. The twelve chemicals include water, methanol, mineral oil, 1-Bromo-4-chlorobutane, 1,5-Hexadiene, di-n-Propyl disulfide, Nonyl aldehyde, Octanoic acid, Dimethylisopropylamine, 5-Isopropyl-2-methylphenol, n-Heptylamine, and N,N-Dimethylbenzylamine. Two different dosing concentrations were evaluated (10 µL into 90 µL reaction reagent and 50 µL into 50 µL reaction reagent) and we found that the results for the 10 µL dose concentration was better because the 50 µL dose concentration results in many dermal irritants and nonirritants were low. For example, as shown in FIG. 7A, in the ethanol solvent, No. 4 1-Bromo-4-chlorobutane was 3.349 (10 µL) as compared to 0.700 (50 µL). In addition, we concluded that letting the p-Nitrophenyl phosphate disodium salt (PNPP) reaction only incubate for 30 minutes was too short and the readings for the dermal irritants and nonirritants were lower than if the reaction incubated for the full hour. For example, as shown in FIG. 7A, for the 10 µL dose in the ethanol solvent, at 30 minutes, No. 5 1,5-Hexadiene was 1.702 and No. 7 Nonyl aldehyde was 1.589. However, after the full 1-hour incubation, as shown in FIG. 7B, No. 5 1,5-Hexadiene was 2.947 and No. 7 Nonyl aldehyde was 3.078. As shown in FIGS. 8A-8B, after the 18 hours incubation, acetone was not the ideal solvent because most of the wells either evaporated or melted. However, ethanol was appeared to be a good solvent because it resolved our problems with previous dermal corrosives not providing the low readings reading. The dermal corrosive chemicals from the previous experiment now had a significant reduction in enzyme activity as shown on FIGS. 8A-8B. Based on this discovery, we focused on refining the alkaline phosphatase reaction reagent to be made from buffered saline and ethanol and to confirm if the 1:100 dilution of the alkaline phosphatase in ethanol and work.

In our next study, we focused on ethanol and buffered saline (potassium chloride, potassium phosphate monobasic, sodium chloride, sodium phosphate dibasic) as our solvents. First we compared two different concentrations (1:100 and 1:1000) of the alkaline phosphatase reaction reagent to optimize the alkaline phosphatase p-Nitrophenyl phosphate disodium salt (PNPP) substrate color intensity response, and incubation at room temperature or at 37° C. Twelve chemicals (4-(Methylthio)benzaldehyde, 1-Bromo-4-chlorobutane, 1,5-Hexadiene, alpha-Terpineol, di-n-Propyl disulfide, Nonyl aldehyde, Octanoic acid, Dimethylisopropylamine, 5-Isopropyl-2-methylphenol, n-Heptylamine, and N,N-Dimethylbenzylamine) were tested. The test chemicals (20 μL) were added to two sets of 0.5 mL microcentrifuge tubes containing 180 μL of the alkaline phosphatase reaction reagent, then incubated at room temperature or 37° C. for 4 hours and 18 hours. After the exposure period, 20 μL of the reaction reagent is added to 200 μL of p-Nitrophenyl phosphate disodium salt (PNPP) substrate solution in a 96-well plate, for readings at 30-minutes and 1-hr at 405 nm.

Protocol

Alkaline Phosphatase Experiment

Seventh Week

Chemical List

| Chemical No. | Chemical Name | CASRN | in vivo GHS |
|---|---|---|---|
| 1 | Water | n/a | n/a |
| 2 | 4-(Methylthio)benzaldehyde | 3446-89-7 | NC |
| 3 | 1-Bromo-4-chlorobutane | 6940-78-9 | NC |
| 4 | 1,5-Hexadiene | 592-42-7 | NC |
| 5 | alpha-Terpineol | 98-55-5 | Cat. 2 |
| 6 | di-n-Propyl Disulfide | 629-19-6 | Cat. 2 |
| 7 | Nonyl aldehyde | 124-19-6 | Cat. 2 |
| 8 | Octanoic Acid | 124-07-02 | Cat. 1B/1C |
| 9 | Dimethylisopropylamine | 996-35-0 | Cat. 1B/1C |
| 10 | 5-Isopropyl-2-methylphenol | 499-75-2 | Cat. 1B/1C |
| 11 | n-Heptylamine | 111-68-2 | Cat. 1B/1C |
| 12 | N,N-Dimethylbenzylamine | 103-83-3 | Cat. 1C |

Preparation

1. Alkaline phosphatase reaction reagent
   a. 1:100
      i. PBS: Take 400 μL of AP (1:10) stock solution, add to 3.6 mL PBS. Vortex mix and then invert to mix 10 times
      ii. Ethanol: Take 400 μL of AP (1:10) stock solution, add to 3.6 mL Ethanol. Vortex mix and then invert to mix 10 times
   b. 1:1000
      i. PBS: Take 400 μL of AP (1:100) stock solution, add to 3.6 mL PBS. Vortex mix and then invert to mix 10 times
      ii. Ethanol: Take 400 μL of AP (1:10)0 stock solution, add to 3.6 mL Ethanol. Vortex mix and then invert to mix 10 times
2. Prepare 0.5 mL microcentrifuge tubes for dosing
   a. One set for room temperature, one set for 37° C.
3. Prepare 96-well plates for PNPP reading (3 wells for each test chemical)
   a. Aliquot with 200 μL PNPP Conditions 1. 1:100 in PBS at RT
2. 1:100 in Ethanol at RT
3. 1:100 in PBS at 37° C.
4. 1:100 in Ethanol at 37° C.
5. 1:1000 in PBS at RT
6. 1:1000 in Ethanol at RT
7. 1:1000 in PBS at 37° C.
8. 1:1000 in Ethanol at 37° C.

Procedure

1. In each microcentrifuge tube for each condition, add 180 μL of the corresponding AP reaction reagent
2. Add 20 μL of the test chemical to each microcentrifuge tube
3. Incubate for 4 hours (one set at room temperature; one set at 37° C.)
4. To prepared 96-well plates with 200 μL PNPP aliquoted, add 20 μL of each microcentrifuge tube to the corresponding well
5. Read at 30 minutes and 1 hour at 405 nm.

Results are shown in FIGS. 9A-9B and FIGS. 10A-10B.

Interpretation for FIGS. 9A-9A and 1A-10B: Twelve chemicals were tested to evaluate the different alkaline phosphatase reaction reagent diluted at 1:100 and 1:1000, the results using ethanol as a solvent, and if exposure incubation temperature affects the results. Based on the results shown in FIGS. 9A-9B and 10A-10B, the 1:1000 dilution of the alkaline phosphatase reaction reagent was too dilute and results were inconclusive because the readings were variable and were not indicative of the normal trend observed in previous studies for the dermal corrosives, irritants, and nonirritants. For example, on FIG. 9B for the 1:1000 ethanol solvent condition, No. 3 1-Bromo-4-chlorobutane, a dermal nonirritant was 0.799 while No. 12 N,N-Dimethylbenzylamine, a dermal corrosive, was 0.587. In addition, the results for incubation at 37° C. were not as good as the results for incubation at room temperature. For example, on FIG. 9D for the 1:100 ethanol solvent condition, No. 2 4-(Methylthio)benzaldehyde was 2.243 at room temperature and 0.857 at 37° C. Therefore, for our next study, we picked the most optimal conditions from this study, which was to use the alkaline phosphatase reaction reagent dilution at 1:100 with buffered saline and ethanol and with a 4 hour incubation at room temperature.

Feb. 1, 2023: In our next study, we focused on the 1:100 concentration of the alkaline phosphatase reaction reagent and explored the option of using a 4 mL glass vial with screw cap instead of the 0.5 mL plastic microcentrifuge tubes. We tested 30 chemicals (1,5-Hexadiene, Isopropanol, 4-(Methylthio)benzaldehyde, Isopropyl myristate, Benzeyl salicylate, Phenylethyl alcohol, Hydroxycitronellal, Benzyl acetate, Dipropylene glycol, di-n-propyl disulfide, 1-Bromopentane, Cyclamen aldehyde, cis-3-Methyl-2-(2-pentenyl)-2-cyclopenten-1-one, p-Metha-1,8-dien-7-ol, Heptanal, trans-3,7-Dimethyl-2,6-octadien-1-ol, alpha-Terpineol, 1-Decanol, Nonyl aldehyde, Dimethyldipropylenetriamine, Potassium hydroxide (100%), 2-Methylbutyric acid, Octanoic acid, Dimethylisopropylamine, 2-tert-Butylphenol, 5-Isopropyl-2-methylphenol, n-Heptylamine, Methoxy-3-propylamine, N,N-Dimethylbenzylamine). We changed the test chemical dosage to 30 μL and the alkaline phosphatase reaction reagent to 300 μL, but kept the incubation to 4 hours at room temperature. The four reaction reagents are R1+ (alkaline phosphatase in phosphate buffered saline), R1− (only phosphate buffered saline), R2+ (alkaline phosphatase in ethanol), and R2− (only ethanol). Another change was adding 3 mL of the p-Nitrophenyl phosphate disodium salt (PNPP) substrate solution directly into the glass vial and letting it sit for 1 hour then adding 200 μL into a 96-well plate for quantification at 405 nm using a spectrophotometer.

Protocol

Alkaline Phosphatase Experiment

Eighth Week

Chemical List

| Chemical No. | Chemical Name | CASRN | in vivo GHS |
|---|---|---|---|
| 1 | NC1: Water | | |
| 2 | NC2: Water/1% Ink | | |
| 3 | PC1: Acetic Acid | | |
| 4 | PC2: Acetic Acid/1% Ink | | |
| 5 | 1-Bromo-4-chlorobutane | 6940-78-9 | NC |
| 6 | 1,5-Hexadiene | 592-42-7 | NC |
| 7 | Isopropanol | 67-63-0 | NC |
| 8 | 4-(Methylthio)benzaldehyde | 3446-89-7 | NC |
| 9 | Isopropyl Myristate | 110-27-0 | NC |
| 10 | Benzyl Salicylate | 118-58-1 | NC |
| 11 | Phenylethyl alcohol | 60-12-8 | NC |
| 12 | Hydroxycitronellal | 107-75-5 | NC |
| 13 | Benzyl Acetate | 140-11-4 | NC |
| 14 | Dipropylene glycol | 25265-71-8 | NC |
| 15 | di-n-Propyl Disulfide | 629-19-6 | Cat. 2 |
| 16 | 1-Bromopentane | 110-53-2 | Cat. 2 |
| 17 | Cyclamen aldehyde | 103-95-7 | Cat. 2 |
| 18 | cis-3-Methyl-2-(2-pentenyl)-2-cyclopenten-1-one | 488-10-8 | Cat. 2 |
| 19 | p-Metha-1,8-dien-7-ol | 18457-55-1 | Cat. 2 |
| 20 | Heptanal | 111-71-7 | Cat. 2 |
| 21 | trans-3,7-Dimethyl-2,6-octadien-1-ol | 106-24-1 | Cat. 2 |
| 22 | alpha-Terpineol | 98-55-5 | Cat. 2 |
| 23 | 1-Decanol | 112-30-1 | Cat. 2 |
| 24 | Nonyl aldehyde | 124-19-6 | Cat. 2 |
| 25 | Dimethyldipropylenetriamine | 10563-29-8 | Cat. 1A |
| 26 | Potassium hydroxide (10%) | 1310-58-3 | Cat. 1B |
| 27 | 2-Methylbutyric acid | 116-53-0 | Cat. 1B/1C |
| 28 | Octanoic Acid | 124-07-02 | Cat. 1B/1C |
| 29 | Dimethylisopropylamine | 996-35-0 | Cat. 1B/1C |
| 30 | 2-tert-Butylphenol | 88-18-6 | Cat. 1B/1C |
| 31 | 5-Isopropyl-2-methylphenol | 499-75-2 | Cat. 1B/1C |
| 32 | n-Heptylamine | 111-68-2 | Cat. 1B/1C |
| 33 | Methoxy-3-propylamine | 5332-73-0 | Cat. 1B/1C |
| 34 | N,N-Dimethylbenzylamine | 103-83-3 | Cat. 1C |

Preparation

1. Reaction Reagents a. 1:100 AP Reaction Reagent i. PBS: Take 4 mL of AP (1:10) stock solution, add to 36 mL PBS. Vortex mix and then invert to mix 10 times ii. Ethanol: Take 4 mL of AP (1:10) stock solution, add to 36 mL Ethanol. Vortex mix and then invert to mix 10 times b. PBS (lx)

c. Ethanol

2. Prepare 4 mL glass vials for dosing a. Four sets i. R1+ (PBS-AP)

ii. R1– (PBS)

iii. R2+ (Ethanol-AP)

iv. R2– (Ethanol)

3. Prepare 96-well plates for PNPP reading (3 wells for each test chemical)

Procedure

1. Aliquot 300 μL of each reaction reagent to 4 mL glass vials.

2. Add 30 μL of the test sample to each 4 mL glass vial.

3. Incubate at room temperature for 4 hours.

4. Aliquot 3 mL of PNPP to each 4 mL glass vial, let sit for 1 hr.

a. Aliquot 750 μL into the 4 mL glass vial to stop the reaction.

5. Incubate for 1 hour and then read results at 405 nm. The results are shown in FIGS. 11A-11E.

Interpretation for FIGS. 1A-1E: Thirty chemicals were tested to evaluate the use of 4 mL glass vials with screw caps instead of 0.5 mL microcentrifuge tubes. Based on the results, as shown on FIGS. 11B and 11D, the dermal corrosives that we troubleshooted were now showing high readings. For example, on FIG. 11B, for the buffered saline alkaline phosphatase reaction reagent, No. 28 (Octanoic Acid; 1.427, 1.415, 1.416), No. 29 (Dimethylisopropylamine; 3.354, 3.466, 3.502), No. 31 (5-Isopropyl-2-methylphenol; 1.990, 1.990, 1.926), and No. 34 (N,N-Dimethylbenzylamine; 3.360, 3.238, 3.273) were high readings. For example, on FIG. 11D, for the ethanol alkaline phosphatase reaction reagent, No. 28 (Octanoic Acid; 3.283, 3.408, 3.220), No. 29 (Dimethylisopropylamine; 2.926, 2.922, 2.852), No. 31 (5-Isopropyl-2-methylphenol; 3.444, 3.465, 3.398), and No. 34 (N,N-Dimethylbenzylamine; 3.429, 3.249, 3.164) were high readings. In previous studies, these dermal corrosives were corrected by the ethanol solvent condition. We discussed the experiment and what variables could have cause these inconsistent results and came to the conclusion that the glass vial was a new variable and discussed how the reagent inside the vial was mixed. We believe that by tilting the vial to mix by pipette and re-pipette, the alkaline phosphatase enzyme may have gotten stuck on the side of the vial and therefore when adding in 3 mL of p-Nitrophenyl phosphate (PNPP) solution, the untouched alkaline phosphatase was interacting with the substrate solution. Therefore, for our next study, we compared with results between the 0.5 mL microcentrifuge tubes previously used with the 4 mL glass vials with screw caps.

Feb. 2, 2023: In our next study, we wanted to compare the difference between the 0.5 mL microcentrifuge tubes and the 4 mL glass vials since the results from the glass vials did not match up with what we have observed in previous studies. The test chemicals included water, acetic acid, heptanal, dimethylisopropylamine, n-Heptylamine, and N,N-Dimethylbenzylamine. We believe that when tilting the glass vial to mix by pipette/re-pipette, the alkaline phosphatase is sticking to the sides and therefore when the p-Nitrophenyl phosphate disodium salt (PNPP) is added, it immediately detects alkaline phosphatase presence and turns intensely yellow. In addition, by sticking to the side of the vial, since the volume of the test chemical added is low, the chance the test chemical interacting with the alkaline phosphatase might be less, therefore resulting in an intensely yellow enzyme reaction product. This study focused on the two stocks (one from previous experiment and a freshly made one) 1:100 concentration ethanol alkaline phosphatase reaction reagent. For the 0.5 mL microcentrifuge tubes, 20 μL of the test chemical is added to 180 μL of the alkaline phosphatase reaction reagent and incubated for 4 hours at room temperature. After the 4-hr incubation, take 20 μL from the 0.5 mL microcentrifuge tube and add to 200 μL of p-Nitrophenyl phosphate disodium salt (PNPP) in a 96-well plate, let sit for 1 hour and then read the results at 405 nm at 30-minutes and 1-hour. For the 4 mL vials, 30 μL of the test chemical is added to 300 μL of the alkaline phosphatase reaction reagent and incubated for 4 hours at room temperature. After the 4-hr incubation, add 3 mL of the p-Nitrophenyl phosphate disodium salt (PNPP) substrate solution and let sit for 30 minutes, then aliquot to a 96-well plate to read results at 405 nm and then repeat this step again with a 1-hour incubation.

Protocol
Alkaline Phosphatase Experiment
Ninth Week
Chemical List

| Chemical No. | Chemical Name | CASRN | in vivo GHS |
|---|---|---|---|
| 1 | NC1: Water | | |
| 3 | PC1: Acetic Acid | | |
| 20 | Heptanal | 111-71-7 | Cat. 2 |
| 29 | Dimethylisopropylamine | 996-35-0 | Cat. 1B/1C |
| 32 | n-Heptylamine | 111-68-2 | Cat. 1B/1C |
| 34 | N,N-Dimethylbenzylamine | 103-83-3 | Cat. 1C |

Conditions
1. Ethanol-AP (1:100) [used during 2.1.23 experiment]
2. Ethanol-AP (1:00)—Newly made prior to this experiment Procedure (0.5 mL microcentrifuge tube)
1. Aliquot 180 µL of each reaction reagent into corresponding tube.
2. Add 20 µL of each test sample, mix by pipette/re-pipette.
3. Incubate at RT for 4 hours.
4. Prepare 96-well plate by aliquoting 200 µL of PNPP, then add 20 µL from the 0.5 mL microcentrifuge tube.
5. Read OD405 at 30 min and 60 min.

Procedure (4 mL vials)
1. Aliquot 300 µL of each reaction reagent into corresponding vial.
2. Add 30 µL of each test sample, mix by pipette/re-pipette.
3. Incubate at RT for 4 hours.
4. Add 3 mL of PNPP to each vial.
5. At 30 minutes, aliquot 200 µL into 96-well plate for reading at OD405
6. At 60 minutes, read the PNPP plate again.

The results for this study are shown in FIGS. 12A-12D.
Interpretation for FIGS. 12A-12D: Four chemicals and two controls were tested to evaluate the differences between using 0.5 mL microcentrifuge tubes and 4 mL glass vials with screw caps and if there were any issues with the ethanol alkaline phosphatase reaction reagent stock. The three dermal corrosives that provided inconsistent results were tested (dimethylisopropylamine, n-heptylamine, and n,n-dimethylbenzylamine). As shown on FIG. 12B, for No. 20 (Heptanal) the results were different between the microcentrifuge tubes (2.360, 2.539, 2.690) and glass vials (0.804, 0.852, 0.901), indicating that this dermal irritant was inhibiting alkaline phosphatase when earlier studies did not show this. Therefore, we concluded that the glass vials were not going to be used and switched back to the 0.5 mL microcentrifuge tubes for the next study.

For our next study, we proceeded with testing of 30 chemicals with the 0.5 mL microcentrifuge tube since the previous experiment determined that glass can confound the results. New stocks were made the of the 1:100 alkaline phosphatase reaction reagents. For the test chemical exposure, 20 µL was added to 0.5 mL microcentrifuge tube aliquoted with 180 µL of the corresponding reaction reagent, incubated for 4 hours, then 20 µL from the 0.5 mL microcentrifuge tube was added to a 96-well plate with 200 µL of p-Nitrophenyl phosphate disodium salt (PNPP) substrate solution and incubated for 1 hour with the results read at 405 nm.

Protocol
Alkaline Phosphatase Experiment
Tenth Week
Chemical List

| Chemical No. | Chemical Name | CASRN | in vivo GHS |
|---|---|---|---|
| 1 | NC1: Water | | |
| 2 | NC2: Water/1% Ink | | |
| 3 | PC1: Acetic Acid | | |
| 4 | PC2: Acetic Acid/1% Ink | | |
| 5 | 1-Bromo-4-chlorobutane | 6940-78-9 | NC |
| 6 | 1,5-Hexadiene | 592-42-7 | NC |
| 7 | Isopropanol | 67-63-0 | NC |
| 8 | 4-(Methylthio)benzaldehyde | 3446-89-7 | NC |
| 9 | Isopropyl Myristate | 110-27-0 | NC |
| 10 | Benzyl Salicylate | 118-58-1 | NC |
| 11 | Phenylethyl alcohol | 60-12-8 | NC |
| 12 | Hydroxycitronellal | 107-75-5 | NC |
| 13 | Benzyl Acetate | 140-11-4 | NC |
| 14 | Dipropylene glycol | 25265-71-8 | NC |
| 15 | di-n-Propyl Disulfide | 629-19-6 | Cat. 2 |
| 16 | 1-Bromopentane | 110-53-2 | Cat. 2 |
| 17 | Cyclamen aldehyde | 103-95-7 | Cat. 2 |
| 18 | cis-3-Methyl-2-(2-pentenyl)-2-cyclopenten-1-one | 488-10-8 | Cat. 2 |
| 19 | p-Metha-1,8-dien-7-ol | 18457-55-1 | Cat. 2 |
| 20 | Heptanal | 111-71-7 | Cat. 2 |
| 21 | trans-3,7-Dimethyl-2,6-octadien-1-ol | 106-24-1 | Cat. 2 |
| 22 | alpha-Terpineol | 98-55-5 | Cat. 2 |
| 23 | 1-Decanol | 112-30-1 | Cat. 2 |
| 24 | Nonyl aldehyde | 124-19-6 | Cat. 2 |
| 25 | Dimethyldipropylenetriamine | 10563-29-8 | Cat. 1A |
| 26 | Potassium hydroxide (10%) | 1310-58-3 | Cat. 1B |
| 27 | 2-Methylbutyric acid | 116-53-0 | Cat. 1B/1C |
| 28 | Octanoic Acid | 124-07-02 | Cat. 1B/1C |
| 29 | Dimethylisopropylamine | 996-35-0 | Cat. 1B/1C |
| 30 | 2-tert-Butylphenol | 88-18-6 | Cat. 1B/1C |
| 31 | 5-Isopropyl-2-methylphenol | 499-75-2 | Cat. 1B/1C |
| 32 | n-Heptylamine | 111-68-2 | Cat. 1B/1C |
| 33 | Methoxy-3-propylamine | 5332-73-0 | Cat. 1B/1C |
| 34 | N,N-Dimethylbenzylamine | 103-83-3 | Cat. 1C |

Preparation
1. Reaction Reagents
   a. 1:100 AP Reaction Reagent
      i. PBS: Take 4 mL of AP (1:10) stock solution, add to 36 mL PBS. Vortex mix and then invert to mix 10 times
      ii. Ethanol: Take 4 mL of AP (1:10) stock solution, add to 36 mL Ethanol. Vortex mix and then invert to mix 10 times
   b. Blank PBS
   c. Blank Ethanol
2. Prepare 0.5 mL microcentrifuge tubes for dosing
   a. Check to make sure they can securely cap
   b. Label accordingly to each condition and chemical
3. Prepare 96-well plates for PNPP reading (3 wells for each test chemical)
   a. Aliquot 200 µL of PNPP into wells Procedure
1. Aliquot 180 µL of each reaction reagent into corresponding tube.
2. Add 20 µL of each test sample, mix by pipette/re-pipette.
3. Incubate at RT for 4 hours.
4. Prepare 96-well plate by aliquoting 200 µL of PNPP before the end of the 4-hour incubation.
5. Add 20 µL from the 0.5 mL microcentrifuge tube.
6. Incubate in PNPP for 60 min.
7. Read results at 405 nm.

Two protocols were developed:

In Chemico Skin Corrosion Test

High Throughput Procedure

This protocol is for testing 6 materials plus controls per 96 well plate.

1. Add 20 μl (or 20 mg if solid) of the material to be tested to each of the 4 types of *prefilled ½ ml tubes labeled A1, B1, A2, B2. Mix by pipette/re-pipette 5 times. NOTE: use a new pipette tip for each aliquot into A1, B1, A2, B2. Close caps. Repeat for each additional test material.

Can also be provided in bulk 20 ml vials and user can aliquot 200 ul to ½ ml tubes.

2. Add 20 μl of the negative control to prefilled 0.5 ml vials labeled NC-A1, NC-B1 and NC-A2, NC-A2. Mix by pipette/re-pipette 5 times. Close caps.

3. Add 20 μl of the positive control to prefilled 0.5 ml vials labeled PC-A1, PC-B1, PC-B1, PC-B2. Mix by pipette/re-pipette 5 times. Close caps.

4. Incubate capped tubes at room temperature for 4 hours+/−10 min.

5. Prefill a 96 well ELISA plate with 200 μl per well with the provided Detection Reagent (DR) solution. Note: Triplicate detection reactions will be done per 0.5 ml tube.

6. After the 4-hour incubation, add 20 μl triplicate aliquots of each ½ ml tube reaction to the ELISA plate. Note: Mix by pipette re-pipette 5 times prior to first aliquot.

7. Incubate at room temperature for 1 hour+/−10 min.

8. Measure the OD 405 nm using a plate reader.

9. Calculate the IC Corrosion score:

a. Subtract the average (of the triplicate aliquots) Blank (B) from the average Active (A) OD results to get the NET OD value. The minimum value is 0.001.

(Plate reader reads only to thousandths place, additional fractions are insignificant)

NET1=A1−B1; NET2=A2−B2 b. Take the NET result and divide by the NET Negative Control OD value to get the NET Ratio. Round Net ratio to nearest thousandth place, the minimum value is 0.001.

NET1 Ratio=NET1/NC1; NET2 Ratio=NET2/NC2 c. Take the inverse of the NET Ratio (1/NET Ratio).

1/NET1 Ratio; 1/NET2 Ratio. (Round to the nearest whole number)

d. The IC Corrosion score is the greater value for either the inverse of NET1 or the inverse of NET2.

10. Apply the IC Corrosion score to the Prediction Model.

11. Predict if the material is corrosive by applying the IC corrosion score to the prediction model.

Field Test Procedure

This protocol is for testing 1 material plus controls in non-laboratory setting.

1. Using the provided calibrated spoons, apply 1 level spoon full (~25 mg) of the material to be tested to each of the prefilled small tubes labeled A1, B1, A2, B2. Use a separate spoon for each tube. Cap and mix by inversion.

2. Add a level spoon full of the negative control to prefilled small tube labeled NC-A1 and NC-A2. Cap and mix by inversion.

3. Add a level spoon full of the positive control to prefilled small tube labeled NC-A1 and NC-A2. Cap and mix by inversion.

4. Incubate capped tubes at room temperature for 4 hours+/−10 min.

5. Retrieve the larger pre-filled glass reaction vials labeled A1, B1, A2, B2.

6. Remove the cap of each small tube and place inverted over the opening of the large tube, so that the entire contents move from small tube to large tube.

7. Recap the small tube and safely discard it. Recap the large vial and mix by inverting 3 times.

8. Incubate at room temperature for 1 hour+/1 10 min.

9. Using a spectrophotometric pipette measure the OD 405 nm.

a. Open the software application for the pipette and tap on "Auto Zero" to blank the pipette using the supplied blanking solution.

b. Tap on "Measurement" to scan the material.

c. Measurements will be saved in the "Datasets" screen.

10. Calculate the IC Corrosion score.

a. Subtract the Blank (B) from the Active (A) OD results to get the NET OD value. The minimum value is 0.001.

(Spectrophotometer reads only to thousandths place, additional fractions are insignificant)

NET1=A1-B1; NET2=A2-B2 b. Take the NET result and divide by the NET Negative Control OD value to get the NET Ratio. Round Net ratio to nearest thousandth place, the minimum value is 0.001.

NET1 Ratio=NET1/NC1; NET2 Ratio=NET2/NC2 c. Take the inverse of the NET Ratio (1/NET Ratio).

1/NET11 Ratio; 1/NET2 Ratio. (Round to the nearest whole number)

d. The IC Corrosion score is the greater value for either the inverse of the NET1 or NET2.

11. Predict if the material is corrosive by applying the IC corrosion score to the prediction model.

Prediction IC Corrosion Score

| Prediction | IC Corrosion Score |
|---|---|
| Noncorrosive | <3 |
| Corrosive | ≥3 |

12. Confirm the positive control A1 and A2 scores are greater than 3, if not the test has failed quality assurance.

| Prediction | IC Corrosion Score |
|---|---|
| Noncorrosive | <3 |
| Corrosive | ≥3 |

12. Confirm the positive control A1 and A2 scores are greater than 3, if not the test has failed quality assurance.

The results for this study are shown in FIGS. 13A-13E.

TABLE 3A

Results for Active Buffered Saline Reaction Reagent

| Chemical | | | A1 - Results | | | | |
|---|---|---|---|---|---|---|---|
| No. | Chemical Name | CASRN | R1 | R2 | R3 | AVG | SE |
| 1 | NC1: Water | | 3.502 | 3.502 | 3.502 | 3.502 | 0.000 |
| 2 | NC2: 1% Water/Ink | | 3.502 | 3.502 | 3.425 | 3.476 | 0.026 |
| 3 | PC1: Acetic Acid | | 0.096 | 0.096 | 0.096 | 0.096 | 0.000 |
| 4 | PC2: 1% Acetic Acid/Ink | | 0.130 | 0.125 | 0.125 | 0.127 | 0.002 |
| 5 | 1-Bromo-4-chlorobutane | 6940-78-9 | 3.387 | 3.502 | 3.502 | 3.464 | 0.038 |
| 6 | 1,5-Hexadiene | 592-42-7 | 3.502 | 3.489 | 3.498 | 3.496 | 0.004 |
| 7 | Isopropanol | 67-63-0 | 3.484 | 3.48 | 3.305 | 3.423 | 0.059 |
| 8 | 4-(Methylthio)benzaldehyde | 3446-89-7 | 3.354 | 3.441 | 3.238 | 3.344 | 0.059 |
| 9 | Isopropyl Myristate | 110-27-0 | 3.373 | 3.496 | 3.484 | 3.451 | 0.039 |
| 10 | Benzyl Salicylate | 118-58-1 | 3.502 | 3.444 | 3.445 | 3.464 | 0.019 |
| 11 | Phenylethyl alcohol | 60-12-8 | 3.502 | 3.502 | 3.403 | 3.469 | 0.033 |
| 12 | Hydroxycitronellal | 107-75-5 | 3.412 | 3.502 | 3.154 | 3.356 | 0.104 |
| 13 | Benzyl Acetate | 140-11-4 | 3.401 | 3.485 | 3.502 | 3.463 | 0.031 |
| 14 | Dipropylene glycol | 25265-71-8 | 3.502 | 3.502 | 3.499 | 3.501 | 0.001 |
| 15 | Di-n-Propyl Disulphide | 629-19-6 | 3.467 | 3.474 | 3.395 | 3.445 | 0.025 |
| 16 | 1-Bromopentane | 110-53-2 | 3.428 | 3.298 | 3.056 | 3.261 | 0.109 |
| 17 | Cyclamen aldehyde | 103-95-7 | 3.405 | 3.502 | 3.502 | 3.470 | 0.032 |
| 18 | cis-3-Methyl-2-(2-pentenyl)-2-cyclopenten-1-one | 488-10-8 | 3.502 | 3.502 | 3.502 | 3.502 | 0.000 |
| 19 | p-Metha-1,8-dien-7-ol | 18457-55-1 | 3.502 | 3.476 | 3.453 | 3.477 | 0.014 |
| 20 | Heptanal | 111-71-7 | 3.409 | 3.131 | 3.049 | 3.196 | 0.109 |
| 21 | trans-3,7-Dimethyl-2,6-octadien-1-ol | 106-24-1 | 3.406 | 3.502 | 3.502 | 3.470 | 0.032 |
| 22 | alpha-Terpineol | 98-55-5 | 3.502 | 3.502 | 3.502 | 3.502 | 0.000 |
| 23 | 1-Decanol | 112-30-1 | 3.502 | 3.466 | 3.380 | 3.449 | 0.036 |
| 24 | Nonyl aldehyde | 124-19-6 | 3.393 | 3.445 | 3.050 | 3.296 | 0.124 |
| 25 | Dimethyldipropylenetriamine | 10563-29-8 | 0.118 | 0.121 | 0.124 | 0.121 | 0.002 |
| 26 | Potassium hydroxide (10%) | 1310-58-3 | 0.118 | 0.111 | 0.112 | 0.114 | 0.002 |
| 27 | 2-Methyl butyric acid | 116-53-0 | 0.101 | 0.117 | 0.135 | 0.118 | 0.010 |
| 28 | Octanoic Acid | 124-07-02 | 0.741 | 0.791 | 0.860 | 0.797 | 0.034 |
| 29 | Dimethylisopropylamine | 996-35-0 | 3.423 | 3.465 | 3.485 | 3.458 | 0.018 |
| 30 | 2-tertiary-Butyl Phenol | 88-18-6 | 0.437 | 0.528 | 0.607 | 0.524 | 0.049 |
| 31 | 5-Isopropyl-2-methylphenol | 499-75-2 | 0.211 | 0.242 | 0.272 | 0.242 | 0.018 |
| 32 | n-Heptylamine | 111-68-2 | 2.141 | 2.668 | 2.862 | 2.557 | 0.215 |
| 33 | Methoxy-3-propylamine | 5332-73-0 | 0.130 | 0.132 | 0.133 | 0.132 | 0.001 |
| 34 | N,N-Dimethylbenzylamine | 103-83-3 | 3.265 | 3.225 | 3.230 | 3.240 | 0.013 |

TABLE 3B

Results for Blank Buffered Saline Reaction Reagent

| Chemical | | | B1 - Results | | | | |
|---|---|---|---|---|---|---|---|
| No. | Chemical Name | CASRN | R1 | R2 | R3 | AVG | SE |
| 1 | NC1: Water | | 0.130 | 0.129 | 0.131 | 0.130 | 0.001 |
| 2 | NC2: 1% Water/Ink | | 0.144 | 0.144 | 0.148 | 0.145 | 0.001 |
| 3 | PC1: Acetic Acid | | 0.096 | 0.094 | 0.095 | 0.095 | 0.001 |
| 4 | PC2: 1% Acetic Acid/Ink | | 0.126 | 0.127 | 0.125 | 0.126 | 0.001 |
| 5 | 1-Bromo-4-chlorobutane | 6940-78-9 | 0.166 | 0.184 | 0.191 | 0.180 | 0.007 |
| 6 | 1,5-Hexadiene | 592-42-7 | 0.161 | 0.152 | 0.150 | 0.154 | 0.003 |
| 7 | Isopropanol | 67-63-0 | 0.123 | 0.122 | 0.120 | 0.122 | 0.001 |
| 8 | 4-(Methylthio)benzaldehyde | 3446-89-7 | 0.175 | 0.170 | 0.169 | 0.171 | 0.002 |
| 9 | Isopropyl Myristate | 110-27-0 | 0.131 | 0.134 | 0.127 | 0.131 | 0.002 |
| 10 | Benzyl Salicylate | 118-58-1 | 0.151 | 0.144 | 0.149 | 0.148 | 0.002 |
| 11 | Phenylethyl alcohol | 60-12-8 | 0.130 | 0.122 | 0.140 | 0.131 | 0.005 |
| 12 | Hydroxycitronellal | 107-75-5 | 0.123 | 0.121 | 0.126 | 0.123 | 0.001 |
| 13 | Benzyl Acetate | 140-11-4 | 0.133 | 0.121 | 0.138 | 0.131 | 0.005 |
| 14 | Dipropylene glycol | 25265-71-8 | 0.130 | 0.133 | 0.133 | 0.132 | 0.001 |
| 15 | Di-n-Propyl Disulphide | 629-19-6 | 0.139 | 0.137 | 0.148 | 0.141 | 0.003 |
| 16 | 1-Bromopentane | 110-53-2 | 0.123 | 0.124 | 0.125 | 0.124 | 0.001 |
| 17 | Cyclamen aldehyde | 103-95-7 | 0.180 | 0.122 | 0.121 | 0.141 | 0.020 |
| 18 | cis-3-Methyl-2-(2-pentenyl)-2-cyclopenten-1-one | 488-10-8 | 0.131 | 0.131 | 0.140 | 0.134 | 0.003 |
| 19 | p-Metha-1,8-dien-7-ol | 18457-55-1 | 0.127 | 0.122 | 0.233 | 0.161 | 0.036 |
| 20 | Heptanal | 111-71-7 | 0.153 | 0.161 | 0.136 | 0.150 | 0.007 |
| 21 | trans-3,7-Dimethyl-2,6-octadien-1-ol | 106-24-1 | 0.132 | 0.119 | 0.120 | 0.124 | 0.004 |

TABLE 3B-continued

Results for Blank Buffered Saline Reaction Reagent

| Chemical | | | B1 - Results | | | | |
|---|---|---|---|---|---|---|---|
| No. | Chemical Name | CASRN | R1 | R2 | R3 | AVG | SE |
| 22 | alpha-Terpineol | 98-55-5 | 0.121 | 0.119 | 0.119 | 0.120 | 0.001 |
| 23 | 1-Decanol | 112-30-1 | 0.131 | 0.126 | 0.118 | 0.125 | 0.004 |
| 24 | Nonyl aldehyde | 124-19-6 | 0.146 | 0.131 | 0.124 | 0.134 | 0.006 |
| 25 | Dimethyldipropylenetriamine | 10563-29-8 | 0.124 | 0.116 | 0.120 | 0.120 | 0.002 |
| 26 | Potassium hydroxide (10%) | 1310-58-3 | 0.110 | 0.111 | 0.112 | 0.114 | 0.002 |
| 27 | 2-Methyl butyric acid | 116-53-0 | 0.103 | 0.117 | 0.135 | 0.118 | 0.010 |
| 28 | Octanoic Acid | 124-07-02 | 0.129 | 0.791 | 0.860 | 0.797 | 0.034 |
| 29 | Dimethylisopropylamine | 996-35-0 | 0.115 | 3.465 | 3.485 | 3.458 | 0.018 |
| 30 | 2-tertiary-Butyl Phenol | 88-18-6 | 0.127 | 0.528 | 0.607 | 0.524 | 0.049 |
| 31 | 5-Isopropyl-2-methylphenol | 499-75-2 | 0.122 | 0.242 | 0.272 | 0.242 | 0.018 |
| 32 | n-Heptylamine | 111-68-2 | 0.124 | 2.668 | 2.862 | 2.557 | 0.215 |
| 33 | Methoxy-3-propylamine | 5332-73-0 | 0.115 | 0.132 | 0.133 | 0.132 | 0.001 |
| 34 | N,N-Dimethylbenzylamine | 103-83-3 | 0.123 | 3.225 | 3.230 | 3.240 | 0.013 |

TABLE 3C

Results for Active Ethanol Reaction Reagent

| Chemical | | | A2 - Results | | | | |
|---|---|---|---|---|---|---|---|
| No. | Chemical Name | CASRN | R1 | R2 | R3 | AVG | SE |
| 1 | NC1: Water | | 3.451 | 3.502 | 2.954 | 3.302 | 0.175 |
| 2 | NC2: 1% Water/Ink | | 3.502 | 3.444 | 3.326 | 3.424 | 0.052 |
| 3 | PC1: Acetic Acid | | 0.996 | 0.724 | 0.829 | 0.850 | 0.079 |
| 4 | PC2: 1% Acetic Acid/Ink | | 0.466 | 0.581 | 0.470 | 0.506 | 0.038 |
| 5 | 1-Bromo-4-chlorobutane | 6940-78-9 | 2.948 | 2.731 | 2.869 | 2.849 | 0.063 |
| 6 | 1,5-Hexadiene | 592-42-7 | 2.692 | 2.767 | 2.693 | 2.717 | 0.025 |
| 7 | Isopropanol | 67-63-0 | 2.294 | 2.902 | 2.389 | 2.528 | 0.189 |
| 8 | 4-(Methylthio)benzaldehyde | 3446-89-7 | 3.379 | 3.355 | 3.266 | 3.333 | 0.034 |
| 9 | Isopropyl Myristate | 110-27-0 | 3.413 | 3.244 | 3.360 | 3.339 | 0.050 |
| 10 | Benzyl Salicylate | 118-58-1 | 3.345 | 3.272 | 3.333 | 3.317 | 0.023 |
| 11 | Phenylethyl alcohol | 60-12-8 | 3.342 | 3.280 | 3.287 | 3.303 | 0.020 |
| 12 | Hydroxycitronellal | 107-75-5 | 2.513 | 2.154 | 3.089 | 2.585 | 0.272 |
| 13 | Benzyl Acetate | 140-11-4 | 3.42 | 3.252 | 3.484 | 3.385 | 0.069 |
| 14 | Dipropylene glycol | 25265-71-8 | 2.343 | 2.467 | 2.685 | 2.498 | 0.100 |
| 15 | Di-n-Propyl Disulphide | 629-19-6 | 2.649 | 2.398 | 2.368 | 2.472 | 0.089 |
| 16 | 1-Bromopentane | 110-53-2 | 2.590 | 2.870 | 2.598 | 2.686 | 0.092 |
| 17 | Cyclamen aldehyde | 103-95-7 | 2.736 | 2.75 | 2.845 | 2.777 | 0.034 |
| 18 | cis-3-Methyl-2-(2-pentenyl)-2-cyclopenten-1-one | 488-10-8 | 2.405 | 2.471 | 2.704 | 2.527 | 0.091 |
| 19 | p-Metha-1,8-dien-7-ol | 18457-55-1 | 2.757 | 2.754 | 2.868 | 2.793 | 0.038 |
| 20 | Heptanal | 111-71-7 | 2.730 | 2.395 | 2.098 | 2.408 | 0.183 |
| 21 | trans-3,7-Dimethyl-2,6-octadien-1-ol | 106-24-1 | 1.876 | 1.851 | 1.956 | 1.894 | 0.032 |
| 22 | alpha-Terpineol | 98-55-5 | 2.223 | 2.751 | 2.793 | 2.589 | 0.183 |
| 23 | 1-Decanol | 112-30-1 | 2.205 | 2.441 | 2.472 | 2.373 | 0.084 |
| 24 | Nonyl aldehyde | 124-19-6 | 2.496 | 2.067 | 2.117 | 2.227 | 0.135 |
| 25 | Dimethyldipropylenetriamine | 10563-29-8 | 0.119 | 0.118 | 0.114 | 0.117 | 0.002 |
| 26 | Potassium hydroxide (10%) | 1310-58-3 | 0.107 | 0.109 | 0.108 | 0.108 | 0.001 |
| 27 | 2-Methyl butyric acid | 116-53-0 | 2.305 | 2.035 | 3.339 | 2.560 | 0.397 |
| 28 | Octanoic Acid | 124-07-02 | 2.12 | 2.776 | 2.129 | 2.342 | 0.217 |
| 29 | Dimethylisopropylamine | 996-35-0 | 0.226 | 0.212 | 0.295 | 0.244 | 0.026 |
| 30 | 2-tertiary-Butyl Phenol | 88-18-6 | 2.829 | 2.567 | 2.448 | 2.615 | 0.113 |
| 31 | 5-Isopropyl-2-methylphenol | 499-75-2 | 2.462 | 2.558 | 2.772 | 2.597 | 0.092 |
| 32 | n-Heptylamine | 111-68-2 | 0.170 | 0.161 | 0.193 | 0.175 | 0.010 |
| 33 | Methoxy-3-propylamine | 5332-73-0 | 0.121 | 0.118 | 0.127 | 0.122 | 0.003 |
| 34 | N,N-Dimethylbenzylamine | 103-83-3 | 0.588 | 0.583 | 0.539 | 0.570 | 0.016 |

TABLE 3D

| | | | | | | | | |
|---|---|---|---|---|---|---|---|---|
| Results for Blank Ethanol Reaction Reagent | | | | | | | | |
| Chemical | | | B2 - Results | | | | | |
| No. | Chemical Name | CASRN | R1 | R2 | R3 | AVG | SE | |
| 1 | NC1: Water | | 0.103 | 0.100 | 0.098 | 0.100 | 0.001 | |
| 2 | NC2: 1% Water/Ink | | 0.119 | 0.119 | 0.120 | 0.119 | 0.000 | |
| 3 | PC1: Acetic Acid | | 0.097 | 0.097 | 0.100 | 0.098 | 0.001 | |
| 4 | PC2: 1% Acetic Acid/Ink | | 0.112 | 0.120 | 0.119 | 0.117 | 0.003 | |
| 5 | 1-Bromo-4-chlorobutane | 6940-78-9 | 0.350 | 0.310 | 0.325 | 0.328 | 0.012 | |
| 6 | 1,5-Hexadiene | 592-42-7 | 0.108 | 0.110 | 0.108 | 0.109 | 0.001 | |
| 7 | Isopropanol | 67-63-0 | 0.102 | 0.105 | 0.107 | 0.105 | 0.001 | |
| 8 | 4-(Methylthio)benzaldehyde | 3446-89-7 | 0.206 | 0.291 | 0.240 | 0.246 | 0.025 | |
| 9 | Isopropyl Myristate | 110-27-0 | 0.131 | 0.126 | 0.111 | 0.123 | 0.006 | |
| 10 | Benzyl Salicylate | 118-58-1 | 0.397 | 0.488 | 0.509 | 0.465 | 0.034 | |
| 11 | Phenylethyl alcohol | 60-12-8 | 0.116 | 0.120 | 0.120 | 0.119 | 0.001 | |
| 12 | Hydroxycitronellal | 107-75-5 | 0.124 | 0.123 | 0.119 | 0.122 | 0.002 | |
| 13 | Benzyl Acetate | 140-11-4 | 0.193 | 0.153 | 0.137 | 0.161 | 0.017 | |
| 14 | Dipropylene glycol | 25265-71-8 | 0.114 | 0.111 | 0.110 | 0.112 | 0.001 | |
| 15 | Di-n-Propyl Disulphide | 629-19-6 | 0.194 | 0.296 | 0.174 | 0.221 | 0.038 | |
| 16 | 1-Bromopentane | 110-53-2 | 0.232 | 0.239 | 0.254 | 0.242 | 0.006 | |
| 17 | Cyclamen aldehyde | 103-95-7 | 0.138 | 0.153 | 0.144 | 0.145 | 0.004 | |
| 18 | cis-3-Methyl-2-(2-pentenyl)-2-cyclopenten-1-one | 488-10-8 | 0.143 | 0.144 | 0.143 | 0.143 | 0.000 | |
| 19 | p-Metha-1,8-dien-7-ol | 18457-55-1 | 0.204 | 0.198 | 0.117 | 0.173 | 0.028 | |
| 20 | Heptanal | 111-71-7 | 0.146 | 0.149 | 0.154 | 0.150 | 0.002 | |
| 21 | trans-3,7-Dimethyl-2,6-octadien-1-ol | 106-24-1 | 0.104 | 0.105 | 0.106 | 0.105 | 0.001 | |
| 22 | alpha-Terpineol | 98-55-5 | 0.106 | 0.106 | 0.108 | 0.107 | 0.001 | |
| 23 | 1-Decanol | 112-30-1 | 0.107 | 0.106 | 0.109 | 0.107 | 0.001 | |
| 24 | Nonyl aldehyde | 124-19-6 | 0.153 | 0.176 | 0.160 | 0.163 | 0.007 | |
| 25 | Dimethyldipropylenetriamine | 10563-29-8 | 0.109 | 0.108 | 0.109 | 0.109 | 0.000 | |
| 26 | Potassium hydroxide (10%) | 1310-58-3 | 0.108 | 0.107 | 0.108 | 0.108 | 0.000 | |
| 27 | 2-Methyl butyric acid | 116-53-0 | 0.111 | 0.111 | 0.111 | 0.111 | 0.000 | |
| 28 | Octanoic Acid | 124-07-02 | 0.154 | 0.135 | 0.137 | 0.142 | 0.006 | |
| 29 | Dimethylisopropylamine | 996-35-0 | 0.108 | 0.107 | 0.105 | 0.107 | 0.001 | |
| 30 | 2-tertiary-Butyl Phenol | 88-18-6 | 0.111 | 0.109 | 0.115 | 0.112 | 0.002 | |
| 31 | 5-Isopropyl-2-methylphenol | 499-75-2 | 0.113 | 0.108 | 0.121 | 0.114 | 0.004 | |
| 32 | n-Heptylamine | 111-68-2 | 0.131 | 0.124 | 0.160 | 0.138 | 0.011 | |
| 33 | Methoxy-3-propylamine | 5332-73-0 | 0.108 | 0.107 | 0.106 | 0.107 | 0.001 | |
| 34 | N,N-Dimethylbenzylamine | 103-83-3 | 0.115 | 0.110 | 0.113 | 0.113 | 0.001 | |

TABLE 4

| Predictivity Statistics | |
|---|---|
| Accuracy | 100.0% (30/30) |
| Bal Acc. | 100.0% |
| Sensitivity | 100.0% (10/10) |
| Specificity | 100.0% (20/20) |
| False Positive Rate | 0.0% (0/20) |
| False Negative Rate | 0.0% (0/10) |

Bal Acc = Balanced accuracy

TABLE 5

| Prediction Model | |
|---|---|
| Prediction | IC Corrosion Score |
| Noncorrosive | <3 |
| Corrosive | ≥3 |

IC = In-chemico

Interpretation of FIGS. 13A-13E, Tables 3A-3D, FIG. 14, Table 4, and Table 5: After reviewing all previous studies, we tested thirty chemicals. The conditions included: 1:100 dilution of alkaline phosphatase reaction reagent with two solvents (buffered saline and ethanol), dosing in 0.5 mL microcentrifuge tubes with 20 μL of chemical added to 180 μL of reaction reagent, and incubating with p-Nitrophenyl phosphate disodium salt (PNPP) substrate for 1-hour. FIGS. 13A-13E show the raw data from the study while Tables 3A-3D calculate the average and standard error. FIG. 14 shows the blank corrected data and calculates the readings as a score that can be interpreted based on the prediction model (Table 5). Table 4 shows the predictivity statistics. This study was highly successful with 100% sensitivity, 100% specificity and 100% accuracy. Compared to the other available nonanimal tests this is a very high level of performance (unheard of level of accuracy, other tests are have accuracies around 80%); and this test is much faster and easier to conduct than other nonanimal test. We concluded that we have discovered a novel test method that is quick and simple way to test the toxicity potential of chemicals. Despite an extensive database search, including the patent databases, peer reviewed publications and the internet, we did could not find any examples of other people or groups trying this approach. We believe we are the first to discover this approach to toxicity testing, it is not expected, and given its ease of use, shelf stability and applications to onsite field testing, this is a novel and potentially useful invention. Again, we stress that no other test takes the approach of using a less activity of purified or semi purified enzymes as a method to identify toxins and no other nonanimal test has a this high predictivity.

Figure 15:
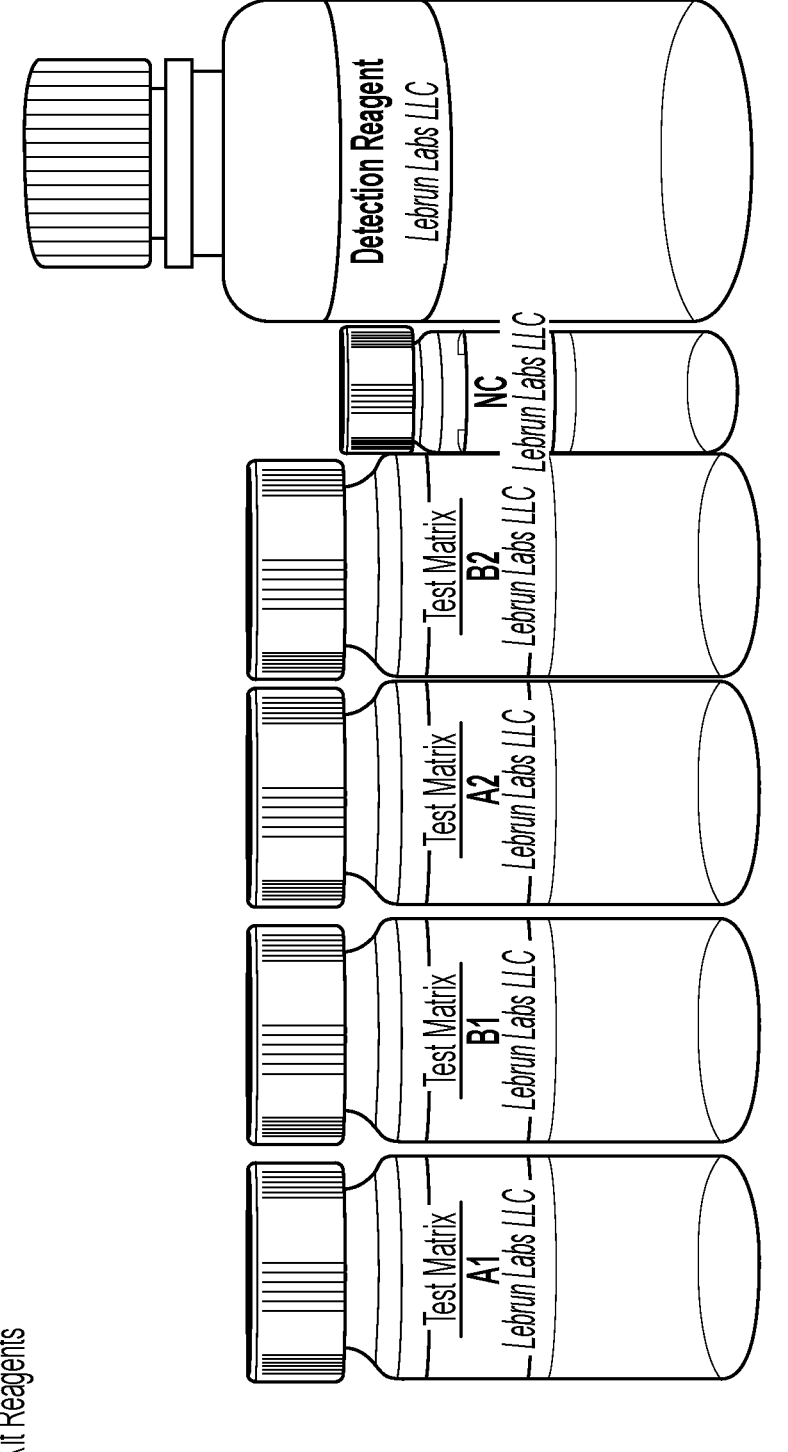
FIG. 15 shows the test kit. The test kit includes the active test matrices (A1 and A2) and the blank test matrices (B1 and B2), the negative control (NC), and the detection reagent. The test kit has a 1-year shelf life. 6 kits were used to test 60 chemicals in triplicate.

As shown in FIG. 15, we have made test kits and used the test kits to study to further evaluate the invention and confirm the accuracy and repeatability of the test method. The ECETOC skin toxin database (ECETOC, 1995) lists in vivo rabbit Draize data including clinical observations after exposure to a large number of readily available chemicals. In addition, there are publications from OECD and ICCVAM that provide guidance on test method validation and include requirements about chemical selection (ICCVAM & NICEA™, 2003; OECD GD 34, 2005), ICCVAM, 1997, ICCVAM, 2023). For preliminary studies, 60 chemicals from the ECETOC database (ECETOC, 1995), published ICCVAM-NICEA™ reference banks (ICCVAM & NICEA™, 2004), OECD Test Guidelines (OECD TG 431, 2019; OECD TG 439, 2021), and published validation studies (Alépée et al., 2019; Han et al., 2021) were selected. Chemicals were selected based diversity of chemical groups and physiochemical properties that fit the chemical selection guidance from the OECD (OECD GD 34, 2005). We made sure to select chemicals with confirmatory secondary in vivo GHS classifications that are accepted by the OECD because they were used for the OECD validation studies for OECD-accepted skin corrosion tests (OECD TG 431, 2019; OECD TG 439, 2021, Alépée et al., 2019; Han et al., 2021). The classifications are listed in FIG. 16 (colored bars). Each chemical name is followed with its CAS RN (in brackets) and has a number which is used to identify the chemical and classification in FIG. 16. The test kit instruction sheet is shown in FIG. 17. Briefly, the test kit procedure involves adding 20 μL of the test substance to 180 μL of each kitted test matrix reagent (FIG. 16, A1, A2, B1, B2) and incubating for 4 h+10 min. After the 4-h incubation, 20 μL from the reaction tube is added to a pre-prepared 96-well plate with 200 μL of the detection reagent (PNPP) and incubated for 1 h+10 min and then read at 405 nm using a microplate reader.

The 60 chemicals tested with the kit included different levels of in vivo skin damage, including NC, Category 2, Category 1BC, and Category 1A. Results are shown in FIG. 18. The average results and standard error from three separate independent runs on different days are shown as the average percent with the background subtracted and normalized into control. FIG. 18 has a cut-off line showing where if the normalized result (percent of negative control) is less than 40% the chemical is predicted to be a corrosive. For the chemicals tested that are: "Not Irritant or Corrosive (NC)" (blue), the normalized results (percent of negative control) ranged from 79.6% to 99.0% with a standard error range from 0.1 to 6.9; For "Irritant (Not Corrosive/Category 2)" (green), the normalized results (percent of negative control) ranged from 69.9% to 95.2% (with the exception of 18.0% for Chemical No. 30, which is a false positive). For Corrosive (Category 1BC; shown in yellow), the normalized result ranged from 0.1% to 30.7% with a standard error range from 0.0 to 6.6. For Extreme Corrosive (Category 1A; shown in red), the normalized results ranged from 0.1% to 28.1% with a standard error range from 0.0 to 1.8. As shown in FIG. 19, the consensus of independent triplicate results (each repeat performed on a different day, with different reagents) indicates the method has excellent predictivity. It is highly sensitive (100%; all corrosives were identified with no FNs), specific (96.7%; only one false positive); and accurate (98.3%) with high within-lab repeatability (100% repeatability) based on corrosive vs. noncorrosive predictions compared with in vivo. We presented the procedure and these results in a webinar to a large audience of skin corrosion experts, and they agreed the shelf stability, ease of use and the 98% accuracy and 100% repeatability of test make it something that was viewed as a highly innovative discovery and can be used to test products and chemicals for the purpose of labeling. Indeed, commercial opportunities for the invention have already emerged.

Novelty and intellectual property: Thus far, our results suggest that chemical toxicity can be modeled using this simple, shelf-stable lab test. This hypothesis is based on the consideration that the epidermis is a complex protective matrix that is chiefly composed of a highly crosslinked protein (keratin) but also includes other proteins and protective factors, one of which is EP. As such, EP has structural and skin distribution properties that make it representative (a "biomarker" for) of the vulnerability of the skin to dermal corrosives. Specifically, strong corrosives degrade the epidermis into the dermis, and, since the EP enzyme is localized within this tissue, it is also degraded by dermal corrosives. Hence, EP activity declines as a function of exposure to dermal corrosives. As shown in FIG. 18, a reduction in EP activity identified all of the dermal corrosives tested with 100% sensitivity, indicating that the mechanisms of corrosion by these chemicals are accounted for. Since we have selected chemicals based on guidelines to be as diverse as possible; the test will be broadly applicable to the identification of dermal corrosives and may be generalizable to all corrosive chemicals. The very high accuracy of our preliminary studies means that even if additional studies identify some mispredictions, the current accuracy will likely still be higher than that of alternatives. In addition, our test has an additional competitive advantage because it is very easy to use and can sit on the shelf (possibly for years) and be ready to quickly and accurately identify toxic materials. Based on the ease of use and predictivity demonstrated so far, this test has the potential to introduce a novel and unexpected paradigm in toxicity testing that may expand test development.

A database search was conducted using Google Scholar, PubMed, USPTO Patent Search Database, Google Patents, and NIH Report. Despite an extensive search, we could not identify any cell-free test that uses enzymatic activity to predict dermal corrosion. To the best of our knowledge, the data presented in this proposal are novel, and we are the first to discover and apply this approach to identify dermal corrosives.

Hypothesis While the most notable proteins of the epidermis are the keratins (intermediate filaments that protect epithelial cells from stressors that may cause cell rupture and death) and of the dermis, collagen (protein that fortifies the skin), there are a broad range of other macromolecules such as elastin and amino acids (Gu and Coulombe, 2007; Brown and Krishnamurthy, 2022) enzymes etc. Our hypothesis that explains our discovery is that the ability of a chemical to destroy molecules and disintegrate the skin or other tissues is not very target specific when the chemical is at a high concentrations compared with the enzyme to be inactivated during the toxin identification test procedure. Based on preliminary findings, we propose that enzyme destruction by a chemical can be used to model (or as a marker for) the potential of a toxin to destroy the molecules of and thereby disintegrate or otherwise disrupt tissues. As noted above, we assumed that an accurate toxicity, irritation or corrosion test would require evaluation of a full thickness tissue model, and we appreciate that those skilled in the art assume that a full thickness tissues or cells or required to determine toxicity, and use of a single enzyme to model toxicity to a larger and complex tissue or organ may be counterintuitive to some or even apparently lack rigor to others. However, we also note that a true "invention" is by definition counterintuitive and not expected by those skilled in the art; and that the purpose of experimentation is to demonstrate results with a level of rigor that if consistent with the hypothesis tested, can overcome intuition and thereby advance the field of study; since we have demonstrated that an enzyme can be used to accurately model tissue and organ toxicity, it is relatively straightforward to apply the same discovery to different enzymes and target systems, we do so in the following prophetic examples:

Prophetic Example: Lung

In a prophetic example, an in chemico test for pulmonary toxins was developed by dilution of 25 units of the enzyme horseradish peroxidase into a "reaction solution 1" (10 ml of 100 mM potassium chloride solution) and also a "reaction solution 2" (50 units of the enzyme horhardish peroxidase diluted into a second vial of 10 ml of Dimethyl sulphoxide). Following a mixing step, ½ ml of each (reaction solution 1 and reaction solution 2) were aliquoted into separate tubes and 10 ul negative control (water) or pulimary toxins (lewisite, nitrogen mustard, phosgene oxime, sulfur mustard, ammonia, bromine, chlorine, hydrogen chloride, methyl bromide, methyl isocyanate, osmium tetroxide, phosgene, phosphine, phosphorus (elemental, white, yellow), sulfuryl fluoride, hydrogen sulfide, cyanide, carbon monoxide, nitrogen, sulfur oxide) and chemicals not toxic to the lungs to form complete reaction 1 and complete reaction 2. In another prophetic step, unknown chemicals were tested. After mixing, the tubes were incubated for 1 hour at 37 C. 200 ul of 3,3',5,5'-Tetramethylbenzidine (TMB) substrate were added to each well of a 96 well plate and 10 ul aliquots of complete reaction 1 were added to 3 wells and 10 ul aliquots of complete reaction 2 were added to another 3 wells. The reaction was incubated for 20 minutes and then 50 ul of 0.16 M sulfuric acid was added to each well to stop the reaction and the Optical density (OD 450) was measured. The measured optical density of the pulmonary irritants and the nonirritant was compared to the control (water) by dividing the measured value into the control value. The materials including the knows and unknowns were identified as a pulmonary irritants if the resulting value was less than 0.6 (60% of control or less).

Prophetic Example: Nervous System

In a prophetic example, an in chemico test for neurotoxins was developed by dilution of semi purified nonspecific peroxidase into a solution of diethylene glycol. Following a mixing step, 100 ul was aliquoted into ½ ml tubes and 10 ul negative control (water) or neurotoxins (sarin, soman, tabun, methylphosphonothioic acid, cyclosarin, S-(Diethylamino) ethyl O-ethyl ethylphosphonothioate, O,O-Diethyl-S-[2-(diethylamino)ethyl]phosphorothioate, Phosphonothioic acid, methyl-, S-(2-(diethylamino)ethyl)O-ethyl ester, O-ethyl-S-[2(diisopropylamino)ethyl]methylphosphonothiolate, lead, ethanol, glutamate, nitric oxide, botulinum toxin, tetanus toxin, gamma-butyrolactone, 2-chloropropanoic acid, amphetamine, nicotine, 1,2,3-trimethylbenzene, 1,2,4-trimethylbenzene, 1,2,5,6,9,10-hexabromocyclodedecane, 1,3-dinitrobenzene, 1-bromopropane, 1-methyl-4-phenyl-1,2,3,6-tetrahydropyridine, 2,5-hexanedione, 3,4-dihydroxymandelaldehyde, 3,4-inethylenedioxymethamphetainine, 3-nitropropanoic acid, 4-hydroxybutyric acid, N-butyilbenzenesulfonamide, N-hydroxy-PhIP, N-methyl-4-phenylpyridinium, N-methylnorsalsolinol, rac-gabaculine, acromelic acid A, acrylamide, aetokthonotoxin, allyl cyanide, bicuculline, butane-1,4-diol, carbon monoxide, ammonia, decabromodiphenyl ether, decarbamoylsaxitoxin, dexorrnaplatin, diethyl phthalate, domoic acid, edifenphos, endrin, hexane, hydrogen peroxide, ibotenic acid, ketamine, lead chromate, leptophos, mancozeb, maneb, mercury, methamphetamine, neosatitoxin, oltipraz, ormaplatin, oxidopamine, paralytic shellfish toxin, phencyclidine, potassium cyanide, resiniferatoxin, salsolinol, saxitoxin, tetrodotoxin, thallium(I) acetate, tinyatoxin, toluene, trimethyltin) and chemicals not toxic to the nervous system to form complete reaction. In additional steps, materials with no know neurotoxicity were tested for neurotoxicity by adding to for additional complete reactions. After mixing, the tubes were incubated at 30 C for 3 hours. Next 100 ul of 2,2'-Azino-bis(3-ethylbenzothiazoline-6-sulfonic acid) diammonium salt was added to each well of a 96 well plate and 100 ul aliquots of complete reaction 1 were added to 3 wells. The reaction was incubated for 60 minutes and then the Optical density at 405 nm was measured. The measured optical density of the neurotoxins and the not neurotoxins and unknowns were compared to the control (water) by dividing the measured value into the control value. The material was identified as a toxin if the resulting value was less than 0.6 (60% n of control or less).

Prophetic Example: Heart

In a prophetic example, a preparation of dried bovine hearts, supplied as a light, fine powder was used as the source of enzymes. The dry powder was added 1% w/v to normal saline and also to an organic solvent (for example DMSO or ethanol). After the solutions were mixed, either in one condition an unknown material or in another condition a known cardiotoxin, for example anthracyclines (daunorubicin, doxorubicin, epirubicin, idarubicin), organophosphates, carbamates, pyrethroids, organochlorines, phosphides, triazoles, triazines, dipyridyls, platinum, cobalt, mercury, nanoparticles (titanium, zinc, silver, carbon, silica, iron oxide), ethanol, or in a third condition a non-cardiotoxic chemical was added. In addition, each material to be tested was added to the saline or organic solvent that did not contain the bovine heart powder. After incubation at a defined temperature for a defined time period, aliquots of each were added to substrates for phosphatase (4-Nitrophenyl phosphate disodium salt [PNPP]), peroxidase (10-Acetyl-3,7-dihydroxyphenoxazine [ADHP]), protease (Casein) or esterase (alpha-Naphthyl acetate). The amount of each product for phosphatase, peroxidase, protease and esterase were quantified by (405 nm, 590 nm, 660 nm, 390-440 nm, respectively) and the toxicity of test material was identified based on a reduction of one or more of the levels of enzymatic product compared to a standard not cardiotoxic chemical such as water.

Prophetic Example: Kidney

In a prophetic example the human kidney cell line HEK 293 were grown to 200 mg or more of cells. Cells were collected by scraping plates with a rubber policeman, and transferred to a conical tube in phosphate buffered saline. Centrifuged, resuspended in saline and centrifuged again to wash. The cells were then suspended in 10 mls of buffered high salt solution (to 100 ml deionized water and 0.14 g Na2HPO4, 0.24 g KH2PO4, 8 g of Sodium chloride to the solution, 1 g of Potassium Chloride 0.14 g of Calcium Chloride, pH to 7.4+/−0.005). After incubation for 30 minutes on ice (to allow cells to take up salt), the cells are centrifuged and resuspended in 10 ls of low salt solution to lyse cells (to 100 ml deionized water and 0.14 g Na2HPO4, 0.24 g KH2PO4, no Sodium chloride to the solution, 0.1 g of Potassium Chloride, no Calcium Chloride, pH to 7.4+/−0.005). After 10 minutes, collect the proteins by adding 1 grams of ammonium sulphate and rotating capped tube for 30 minutes at 4-8 C. Collect pellet by centrifugation. Resuspend pellet in 2 mls of phosphate buffered saline (PBS), and transfer to a dialysis membrane with 10 kd pore size. Dialyze with refrigeration 3 times against 1 liter of PBS. The. resulting solution is a crude cell free enzyme preparation.

Add the unknown material to be tested, known kidney toxins (benzene, organic solvents, degreasing agents, glyphosate, paraquat, 1,2-Dibromo-3-chloropropane, cadmium, uranium, lead, mercury, ethylene glycol, methanol, isopropyl alcohol, cannabinoids, amphetamines, organophosphates), materials known not to be toxic to kidneys to separate tubes of the cell free enzyme material. Include a water control. Incubate for 18 hours at 37 C. Measure the esterase activity transfer an aliquot of each to a 96 well plate that contains 200 ul of a Naphthol AS-D chloroacetate solution. Allow the mixture to incubate for 2 hours. Measure the optical density (OD). Compare the resulting OD of the toxins and unknown with the OD of the negative control and non-toxins. Identify the materials as toxic if the OD is significantly less than the negative control.

Prophetic Example: Liver

Obtain a section of bovine liver. Cut into small pieces, add to a small volume of PBS and homogenize using a Dounce homogenizer. Transfer to centrifuge tube and conduct a slow speed (200 rpm) centrifugation. Remove the upper ½, leaving any solid material in the lower ½. separate into different aliquots, add control, unknowns to be tested, and known hepatotoxins (amoxicillin-clavulanate, flucloxacillin, erythromycin, diclofenac, sulfamethoxazole/trimethoprim, isoniazid, disulfram, ibuprofen, flutamide, vinyl chloride, carbon tetrachloride, paraquat, polychlorinated biphenyls, 2-Nitropropane, 4,4'-Methylenedianiline, 2,4,6-Trinitrotoluene, ethylene dichloride, propylene dichloride, carbon tetrabromide, acetylene tetrabromide, ethylene dibromide, hexachloronaphthalene, octachloronaphthalene, trichloronaphthalene, N-titrosodimethylamine, timethylformamide, tetrahydrofuran, dimethyl acetamide, diphenyl) and known non-hepatotoxins. Incubate for 4 hours. Transfer an aliquot to an alkaline phosphatase substrate (for example 4-Nitrophenyl phosphate disodium salt hexahydrate), incubate 1 hour, measure the OD (405 nm), predict the material is a liver toxin if the unknown or known liver toxins reduce the OD by 50% as compared to the negative control.

Prophetic Example: Eye

In a prophetic example food source bovine corneas are collected; cells are killed by freezing and then thawing 3 times. 5 mm corneal buttons are collected using a biopsy punch. Corneal buttons are placed into a 96 well plate, and 150 ul of a negative control, known ocular irritants and known ocular nonirritants are added to different wells with buttons. After a 10 minute incubation, the buttons are removed, washed 3 time in PBS and transferred to the esterase substrate Naphthol AS-D chloroacetate solution. After 1 hour incubation, buttons are removed and the oD is measured. The materials are identified as irritants or ocular corrosives based on the OD being significantly below the value for the control.

Prophetic Example: Acute Toxicity

In a prophetic example, the bacteria E. coli were used as a source of peroxidase. A culture of E. coli (Escherichia Coli) was grown in Luria-Bertani (LB) broth to late log phase in a 2 liter flask. The cells were collected by centrifugation, washed with PBS and killed and lysed by grinding in a Dounce homogenizer and 3 rounds of freeze to −80 C thaw at 37 C. The resulting lysate was used as is to identify acute toxins. 100 ul of lysate was aliquoted into each well of a 96 well plate. Test materials were diluted as follows: A 10 fold serial dilution (from 1:10 to 1:10 million) of a negative control (water) a positive control (5% Sodium dodecyl sulfate, CASRN 151-21-3), 1 very toxic chemical, 1 mid toxic chemical and 1 low toxic chemical, and 1 essentially not toxic material and 1 unknown. 10 ul of each concentration of each test material was added to a well of the 96 well plate containing the lysate and mixed by pipette re-pipette. The 96 well plate was covered and incubated at 37 C for 1 hour. After incubation, 3, 96 well plates had 200 ul of a solution with the peroxidase substrate 2,2'-Azino-bis(3-ethylbenzothiazoline-6-sulfonic acid) added. Then triplicate 20 ul aliquots of the lysate with serial dilutions of test materials were added to each well and mixed by pipette, re-pipette. The plate was transfer to 37 C from a 1 hour incubation. After incubation the OD at 405 nm was measured using a plate reader or spectrophotometry. The unknown materials was judged to have a similar toxicity to the best OD match for the controls: best OD fit within the range of very toxic, mid-level toxic, mild toxic, essentially nontoxic based on which unknown OD was closed to each of these. In an added step, the mg'kg of each of these required to result in an effective dose (ED) of 20, 50 and 80 or lethal dose (LD) 20, 50, and 80 was calculated by comparing a curve extrapolated using Graphpad's Prism software.

Prophetic Example: Skin Irritation

5-Bromo-4-chloro-3-indolyl β-D-galactopyranoside was diluted in salt water and 200 ul added to each well of a 96 well plate. Serial dilutions of known dermal irritants, known nonirritants and water control and unknown chemicals. A 20 ul aliquot of galactosidase substrate was added to each well and the unknowns were judged to be irritants if the OD was lower than the known irritant positive controls.

Prophetic Example: Skin Corrosion

Prepare reaction reagents (enzyme in buffered saline and ethanol) using the chosen enzyme substrate system such as 4-Nitrophenyl phosphate disodium salt hexahydrate (phosphatase), 3,3'-Diaminobenzidine tetrahydrochloride (peroxidase), o-Phenylenediamine dihydrochloride (peroxidase), o-Phenylenediamine (peroxidase), o-Dianisidine (peroxidase), 3,3',5,5'-Tetramethylbenzidine dihydrochloride (peroxidase), 4-Chloro-1-naphthol (peroxidase), 3-Amino-9-ethylcarbazole; (peroxidase). To 0.5 mL microcentrifuge tubes, add 180 µL of each corresponding reaction reagent. Then add 20 µL of the test material and mix by pipette and re-pipette. Incubate at room temperature for 1-minute, 1 hour, and 4 hours. After each timepoint, add L to 200 µL of the chosen substrate solution and read results at the corresponding wavelength. The results from the different timepoints will be indicative of the different Category 1 subcategories (Category 1A, Category 1B, and Category 1C).

Enzyme activity results after toxin exposure will be averaged to form a toxic activity class, and results from enzyme activity after exposure to nontoxic exposure will be averaged to form a nontoxic activity class. The results are then used to define an activity cutoff value that separates the toxic activity class from the nontoxic activity class, and this value is used to define a prediction model. Substances with reference or benchmark data are then tested and results are applied to the prediction model. This data is analyzed to determine test predictivity including accuracy. It is generally accepted the tests with an accuracy of 80% or better are useful.

Summary It was discovered that tissue toxicity for a broad range of diverse, generalized, toxic chemicals can be identified by measuring the inactivation of a representative enzyme(s). While the proposed generalized toxins are highly reactive, this reactivity is not specific to a single molecule or enzyme or enzyme active or regulatory site, and is not specific to the enzyme used to evaluate the generalized loss of function and subsequent toxicity.

The invention easily identifies generalized loss-of-function toxins by measuring a decrease in enzyme activity resulting from exposure to the test material or substance and the change in enzyme activity serves only as a functional marker or representative of the generalized toxicity of the test material or substance.

Purified or semipurified enzymes can be stored as lyophilized powders or stabilized (for example, frozen). As such, a product based on the technology will have a shelf life of months to years, which is a clear advantage compared with many toxicology tests that require live cells or organisms.

Identification of relevant, generalized, chemical toxic reactivity would be complex without an enzyme marker to gauge functional status. Simply measuring generalized denaturation without a defined enzyme marker or measuring toxin binding to specific protein sequences requires complex assay design and analytical methods and are not as simple, rapid, and useful as measuring a reduction in enzyme activity. In addition, while measuring toxin binding to specific peptides may indicate specific endpoints such as allergic response or sensitization potential, this will not evaluate a generalized loss of functionality and resulting toxicity for a broad range of toxic chemicals as described for this invention. Likewise, measurement of turbidity related to protein denaturation may be relevant to a specific endpoint in ocular toxicity: opacity of the cornea. However, corneal opacity can be transient or permanent and is distinct from other ocular toxicity endpoints including redness, swelling, pain, discharge, and lesions. Opacity of the cornea is a narrow and tissue-specific toxic endpoint that does not reflect the overall activity status of the ocular tissue. Hence, we teach away from measuring toxin binding to peptides, small molecules, and nonenzyme macromolecules since this would be analytically complex and not amenable to the type of simple and easy-to-use test described here. Besides being complex, measuring "protein denaturation" or specific binding reactions does not indicate general functional status. Use of an enzyme marker provides a direct and easy-to-perform evaluation of generalized functional status.

For this invention, many different enzymes can be used to gauge the functional status that, when activity declines to predefined levels, indicates generalized toxicity. Because the effects are not specific to a single enzyme, the choice of which enzyme(s) to use can be based on the availability of the enzyme, required analytical methods and characteristics including methods of quantification of activity and robustness of methods of quantification, the range and clarity of measurable activities, potential for cut-off values that result in high accuracy and repeatability, reliability, cost, ease of use, and the practicality of the assay system used to measure changes in representative enzymatic activity.

We propose that generalized toxins reduce the function of the tissue, and nonspecific enzyme inactivation is one of the many outcomes of chemical toxin exposure. As disclosed in the examples, the concentration or ratio of test material to the amount of enzyme used as the marker for toxicity exceeds by orders of magnitude the ratio used for drug screening or therapeutic use; even if such drug screening tests incidentally uses dead, inactivated, or purified cell free systems for "high throughput screening," the screening assays to identify drugs or small molecules that specifically change enzyme activity are conducted at concentrations orders of magnitude below what is required for the generalized toxicity test of this invention. For example, the in chemico test is conducted at mg/mL (toxin/enzyme solution) concentrations versus drug screening or therapeutic use where the drug to body ratios will be in the pg/g or fg/g range or even more dilute than fg/g.

In certain embodiments, the invention will use cells or tissues, but these cells or tissues cannot be viable because cells may produce the enzyme, thereby confounding the interpretation of the reduction of enzymatic activity as a measure of toxicity. We recognize that this is unexpected because existing enzymatic measures of toxicity use regulation by the cell as a measure of toxicity, and the invention uses the opposite of the standard: dead or inactivated cells or a cell-free system.

While standardized diagnostic tests widely measure biological fluid enzyme levels, these tests measure the dynamic changes of enzyme levels produced by cells, tissues, or the body; these tests compare enzyme levels with reference levels of biological fluids to determine if more or less of a given enzyme is produced. Such diagnostic techniques are inconsistent with the method proposed here because for the disclosed invention, it is essential that the mass of the enzyme or activity is standardized, and there be no active live cell-related increase or decrease in the mass or activity of enzymes. The invention requires an acellular or nonviable cell test procedure to allow measurement of activity changes as a result of direct toxin interaction with a defined mass or activity of enzyme. For these reasons, we teach away from in vivo and live cells.

While various aspects and embodiments have been disclosed herein, other aspects and embodiments will be apparent to those skilled in the art.

The various aspects and embodiments disclosed herein are for purposes of illustration and are not intended to be limiting, with the true scope and spirit being indicated by the following claims.

One skilled in the art will appreciate that this and other processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed:

1. A method for predicting the living dermal or ocular tissue irritancy, corrosiveness or toxicity of a test substance, the method comprising:
applying the test substance to a predefined enzyme or enzyme mixture to effect an in chemico reaction, wherein the test substance does not preferentially or specifically bind to an active or regulatory site of the predefined enzyme or enzyme mixture, wherein the enzyme or enzyme mixture comprises a phosphatase and/or an esterase;

measuring any reduction in enzymatic activity of the predefined enzyme or enzyme mixture on a predefined substrate; and, comparing the measured reduction in enzymatic activity to a control activity value or previously established activity value, and predicting the extent of, or classification of, living tissue toxicity of the test substance based on the compared measured reduction in enzymatic activity, wherein a reduction in enzymatic activity to 40% or less of control activity value or previously established value by said test substance indicates the test substance is corrosive or toxic to living dermal or ocular tissue, and wherein a reduction in enzymatic activity to a level which is more than 40% of control activity value or previously established value but equal to 60% or less of control activity value or previously established value indicates the test substance is an irritant to living dermal or ocular tissue.

2. The method of claim 1, where the enzyme is purified or semipurified or is in a mixture composed of nonviable cells and/or nonviable tissue.

3. The method of claim 1, wherein the test substance irreversibly reduces the enzyme activity and/or noncompetitively reduces the enzyme activity.

4. The method of claim 1, wherein the test substance reduces enzyme activity by chemically destroying or denaturing the enzyme.

5. The method of claim 1, wherein the test substance is applied at concentrations that are toxic and not therapeutic.

6. The method of claim 1, where the mass of test substance is applied to the enzyme at a ratio of 1:1-1:100 parts test substance to enzyme solution volume.

7. The method of claim 1, where the mass of test substance is applied to the enzyme at a ratio of 1:10-1:1,000 parts test substance to enzyme solution volume.

8. The method of claim 1, wherein the test substance is applied at concentrations of mg/mL and not at μg/mL-fg/mL.

9. The method of claim 1, wherein the test substances are a diverse group of toxins without having specific binding affinity or binding to the enzyme regulatory or active sites.

10. The method of claim 1, wherein the test predicts toxicity to living skin, and the accuracy of prediction is 85% or greater.

11. The method of claim 1, wherein the enzyme is a phosphatase.

12. The method of claim 1, wherein the toxicity is corrosiveness, and the method predicts the corrosiveness or not of the test substance with an accuracy of at least 85%.

13. The method of claim 12, wherein noncorrosiveness is predicted if remaining enzyme activity is greater than 40% of the control or previously established value by said test substance.

14. The method of claim 12, in which the accuracy to predict if the test substance is a dermal corrosive is 90% or greater.

15. The method of claim 1, wherein the predefined enzyme or enzyme mixture is sequentially exposed to each of at least known 10 toxins and sequentially exposed to each of at least known 10 nontoxins, and results for the enzyme activity after toxin exposure are averaged to form an activity class, and results from enzyme activity after exposure to nontoxin exposure is averaged to form an activity class, and the activity class measurement for the toxin class is significantly reduced enzyme activity compared with activity for the nontoxin activity class, and there is a statistically significant separation of the toxin class activity values from the nontoxin class activity P values <0.01, and these results are then used to construct a prediction model that identifies toxins based on a specific reduction of enzyme activity with intended use of a prediction model for the identification and classification of the toxicity of unknown materials and when used to test unknowns for toxicity, and an accuracy of prediction of at least 85%.

16. The method of claim 1, in which lack of active site binding specificity is verified using a chemical analytical technique.

17. The method of claim 1, wherein the tissue to be evaluated comprises an ocular tissue, and the accuracy of prediction is at least 85%.

18. The method of claim 1, wherein the enzyme is an esterase.

19. The method of claim 1, wherein the toxicity is irritancy, and the method predicts the test substance as an irritant or nonirritant with an accuracy of at least 85%.

* * * * *